(12) United States Patent
Ciulli et al.

(10) Patent No.: US 11,261,179 B2
(45) Date of Patent: Mar. 1, 2022

(54) SMALL MOLECULES

(71) Applicant: University of Dundee, Dundee (GB)

(72) Inventors: Alessio Ciulli, Dundee (GB); Chiara Maniaci, Dundee (GB); Scott J. Hughes, Dundee (GB); Andrea Testa, Dundee (GB)

(73) Assignee: University of Dundee, Dundee (GB)

( * ) Notice: Subject to any disclaimer, the term of this patent is extended or adjusted under 35 U.S.C. 154(b) by 78 days.

(21) Appl. No.: 16/604,737

(22) PCT Filed: Apr. 13, 2018

(86) PCT No.: PCT/GB2018/050987
§ 371 (c)(1),
(2) Date: Oct. 11, 2019

(87) PCT Pub. No.: WO2018/189554
PCT Pub. Date: Oct. 18, 2018

(65) Prior Publication Data
US 2021/0163469 A1 Jun. 3, 2021

(30) Foreign Application Priority Data

Apr. 14, 2017 (GB) ..................................... 1706042
Apr. 14, 2017 (GB) ..................................... 1706043

(51) Int. Cl.
*C07D 417/14* (2006.01)
(52) U.S. Cl.
CPC ................................ *C07D 417/14* (2013.01)
(58) Field of Classification Search
CPC .................................................. C07D 417/14
USPC ....................................................... 514/365
See application file for complete search history.

(56) References Cited

FOREIGN PATENT DOCUMENTS

| JP | 2015508414 A | 3/2015 |
|---|---|---|
| WO | 2013106643 A2 | 7/2013 |
| WO | 2015160845 A2 | 10/2015 |
| WO | 2016105518 A1 | 6/2016 |
| WO | 2016146985 | 9/2016 |
| WO | 2016149668 A1 | 9/2016 |

OTHER PUBLICATIONS

Accurso et al. "Improved Metal-Adhesive Polymers from Copper(I)-Catalyzed Azide-Alkyne Cycloaddition" Chemistry: A European Journal, 20:10710-10719 (2014).
Arrowsmith et al. "The promise and peril of chemical probes" Nature Chemical Biology, 11:536-541 (2015).
Bondeson et al. "Catalytic in vivo protein knockdown by small-molecule PROTACs" Nature Chemical Biology, 11(8):611-617 (2015).
Bonnet et al. "Ionic strength mediated hydrophobic force switching of CF3-terminated ethylene glycol self-assembled monolayers (SAMs) on gold" Chemical Communications, 47:5066-5068 (2007).
Botusan et al. "Stabilization of HIF-1alpha is critical to improve wound healing in diabetic mice" Proceedings of the National Academy of Sciences, 105(49):19426-19431 (2008).
Bouzide et al. "Silver(I) oxide-mediated facile and practical sulfonylation of alcohols" Tetrahedron Letters, 42:8781-8783 (2001).
Buckley et al. "Targeting the von Hippel-Lindau E3 Ubiquitin Ligase Using Small Molecules To Disrupt the VHL/HIF-1alpha Interaction" Journal of the American Chemical Society, 134:4465-4468 (2012).
Buckley et al. "HaloPROTACS: Use of Small Molecule PROTACs to Induce Degradation of HaloTag Fusion Proteins" ACS Chemical Biology, 10(8):1831-1837 (2015).
Chamberlain et al. "Structure of the human Cereblon-DDB1-lenalidomide complex reveals basis for responsiveness to thalidomide analogs" Nature Structural & Molecular Biology, 21(9):803-810 (2014).
Crew et al. "Identification and Characterization of Von Hippel-Lindau-Recruiting Proteolysis Targeting Chimeras (PROTACs) of TANK-Binding Kinase 1" Journal of Medicinal Chemistry, 61(2):583-598 (2018).
Eckle et al. "HIF1A Reduces Acute Lung Injury by Optimizing Carbohydrate Metabolism in the Alveolar Epithelium" PLoS Biology, 11(9):e1001665 (2013).
Erb et al. "Transcription control by the ENL YEATS domain in acute leukaemia" Nature, 543(7644):270-274 (2017).
Fischer et al. "Structure of the DDB1-CRBN E3 ubiquitin ligase in complex with thalidomide" Nature, 512(7512):49-53 (2014).
Frost et al. "Potent and selective chemical probe of hypoxic signalling downstream of HIF-alpha hydroxylation via VHL inhibition" Nature Communications, 7(13312):1-12 (2016).
Gadd et al. "Structural basis of PROTAC cooperative recognition for selective protein degradation" Nature Chemical Biology, 13:514-521 (2017).
Galdeano et al. "Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities" Journal of Medicinal Chemistry, 57:8657-8663 (2014).
Hill et al. "Inhibition of Hypoxia Inducible Factor Hydroxylases Protects Against Renal Ischemia-Reperfusion Injury" Journal of the American Society of Nephrology, 19(1):39-46 (2008).
International Search Report and the Written Opinion of the International Searching Authority corresponding to International Patent Application No. PCT/GB2018/050987 (15 pages) (dated Jun. 7, 2018).
Ito et al. "Identification of a Primary Target of Thalidomide Teratogenicity" Science, 327:1345-1350 (2010).

(Continued)

*Primary Examiner* — Kahsay Habte
(74) *Attorney, Agent, or Firm* — Myers Bigel, P.A.

(57) ABSTRACT

Compounds having the general structure A-L-B are presented wherein A and B are independently an E3 ubiquitin ligase protein binding ligand compound of formula 1A or 1B. Pharmaceutical compositions comprising these compounds and methods of use are also presented.

17 Claims, 34 Drawing Sheets

(56) References Cited

OTHER PUBLICATIONS

Itoh et al. "Protein Knockdown Using Methyl Bestatin-Ligand Hybrid Molecules: Design and Synthesis of Inducers of Ubiquitination-Mediated Degradation of Cellular Retinoic Acid-Binding Proteins" Journal of the American Chemical Society, 132:5820-5826 (2010).
Jain et al. "Hypoxia as a therapy for mitochondrial disease" Science, 352(6281):54-61 (2016).
Karuppagounder et al. "Hypoxia-inducible factor prolyl hydroxylase inhibition: robust new target or another big bust for stroke therapeutics?" Journal of Cerebral Blood Flow & Metabolism, 32:1347-1361 (2012).
Knuf et al. "Preparation of Discrete Oligoethers: Synthesis of Pentabutylene Glycol and Hexapropylene Glycol by Two Complementary Methods" The Journal of Organic Chemistry, 68(23):9166-9169 (2003).
Kronke et al. "Lenalidomide Causes Selective Degradation of IKZF1 and IKZF3 in Multiple Myeloma Cells" Science, 343:301-305 (2014).
Lai et al. "Modular PROTAC Design for the Degradation of Oncogenic BCRABL" Angewandte Chemie, 55(2):807-810 (2016).
Lebraud et al. "Protein Degradation by In-Cell Self-Assembly of Proteolysis Targeting Chimeras" ACS Central Science, 2(12):927-934 (2016).
Loenarz et al. "Evidence for a Stereoelectronic Effect in Human Oxygen Sensing" Angewandte Chemie, 48:1784-1787 (2009).
Lu et al. "The Myeloma Drug Lenalidomide Promotes the Cereblon-Dependent Destruction of Ikaros Proteins" Science, 343:305-309 (2014).
Lu et al. "Hijacking the E3 Ubiquitin Ligase Cereblon to Efficiently Target BRD4" Chemistry & Biology, 22:1-9 (2015).
MacDougall, Iain C. "Novel Erythropoiesis-Stimulating Agents: A New Era in Anemia Management" Clinical Journal of the American Society of Nephrology, 3:200-207 (2008).
Maniaci et al. "Homo-PROTACs: bivalent small-molecule dimerizers of the VHL E3 ubiquitin ligase to induce self-degradation" Nature Communications, 8:1-14 (2017).
Matyskiela et al. "A novel cereblon modulator recruits GSPT1 to the CRL4CRBN ubiquitin ligase" Nature, 535(7611):252-257 (2016).
Ohoka et al. "In Vivo Knockdown of Pathogenic Proteins via Specific and Nongenetic Inhibitor of Apoptosis Protein (IAP)-dependent Protein Erasers (SNIPERs)" The Journal of Biological Chemistry, 292(11):4556-4570 (2017).
Petzold et al. "Structural basis of lenalidomide-induced CK1alpha degradation by the CRL4CRBN ubiquitin ligase" Nature, 532(7597):127-130 (2016).
Provenzano et al. "Oral Hypoxia-Inducible Factor Prolyl Hydroxylase Inhibitor Roxadustat (FG-4592) for the Treatment of Anemia in Patients with CKD" Clinical Journal of the American Society of Nephrology, 11:982-991 (2016).
Raina et al. "PROTAC-induced BET protein degradation as a therapy for castration-resistant prostate cancer" Proceedings of the National Academy of Sciences, 113(26):7124-7129 (2016).
Ramsay et al. "Environmental and metabolic sensors that control T cell biology" Frontiers in Immunology, 6(99):1-8 (2015).
Rapisarda et al. "Identification of Small Molecule Inhibitors of Hypoxia-inducible Factor 1 Transcriptional Activation Pathway" Cancer Research, 62:4316-4324 (2002).
Rey et al. "Synergistic effect of HIF-1 gene therapy and HIF-1-activated bone marrow-derived angiogenic cells in a mouse model of limb ischemia" Proceedings of the National Academy of Sciences, 106(48):20399-20404 (2009).
Robinson et al. "Mucosal Protection by Hypoxia-Inducible Factor Prolyl Hydroxylase Inhibition" Gastroenterology, 134:145-155 (2008).
Ruthenborg et al. "Regulation of Wound Healing and Fibrosis by Hypoxia and Hypoxia-Inducible Factor-1" Molecules and Cells, 37(9):637-643 (2014).
Sun, Yi "Targeting E3 Ubiquitin Ligases for Cancer Therapy" Cancer Biology & Therapy, 2(6):623-629 (2003).
Toure et al. "Small-Molecule PROTACS: New Approaches to Protein Degradation" Angewandte Chemie, 55:2-10 (2016).
Winter et al. "Phthalimide conjugation as a strategy for in vivo target protein degradation" Science, 348(6241):1376-1381 (2015).
Wittmann et al. "Ligand Recognition by E- and P-Selectin: Chemoenzymatic Synthesis and Inhibitory Activity of Bivalent Sialyl Lewis x Derivatives and Sialyl Lewis x Carboxylic Acids" The Journal of Organic Chemistry, 63:5137-5143 (1998).
Young et al. "Total Synthesis of (+)-Nakadomarin A" Journal of the American Chemical Society, 129:1465-1469 (2007).
Zengerle et al. "Selective Small Molecule Induced Degradation of the BET Bromodomain Protein BRD4" ACS Chemical Biology, 10:1770-1777 (2015).
Zhou et al. "Discovery of a Small-Molecule Degrader of Bromodomain and Extra-Terminal (BET) Proteins with Picomolar Cellular Potencies and Capable of Achieving Tumor Regression" Journal of Medicinal Chemistry, 61(2):462-481 (2018); Epub Mar. 24, 2017.
Office action with English translation corresponding to Japanese Application No. 2019-555894 (9 pages) (dated Dec. 20, 2021).

SMALL MOLECULES

FIELD OF THE INVENTION

This invention relates to small molecule E3 ubiquitin ligase protein binding ligand compounds, and to their utility in PROteolysis Targeted Chimeras (PROTACs), as well as processes for the preparation thereof, and use in medicine. This invention particularly relates to PROTACs capable of inducing auto-ubiquitination of E3 ubiquitin ligases and triggering their subsequent proteasomal degradation.

BACKGROUND OF THE INVENTION

E3 ubiquitin ligases are emerging as attractive targets for small-molecule modulation and drug discovery. E3s bring a substrate protein and ubiquitin in close proximity to each other to catalyze the transfer of a ubiquitin molecule to the substrate. Substrate ubiquitination can trigger different cellular outcomes, of which one of the best characterized is poly-ubiquitination and subsequent proteasomal degradation. The human genome comprises >600 predicted E3 ligases that play important roles in normal cellular physiology and disease states, making them attractive targets for inhibitor discovery. However, E3 ligases do not comprise deep and "druggable" active sites for binding to small molecules. Blockade of E3 ligase activity therefore requires targeting of protein-protein interactions (PPIs), and the often extended, flat and solvent-exposed PPI surfaces make it a challenge for drug design. Only a few potent inhibitors have been developed to date, mostly compounds that bind to the E3 substrate recognition site, for example MDM2, inhibitor of apoptosis proteins (IAPs), the von Hippel-Lindau (VHL) ligase,[1-3] and KEAP1. Inhibitors of E3:substrate interaction can exhibit a discrepancy in effective concentrations between biophysical binding and cellular efficacy,[3] due to competition from high-affinity endogenous substrates that markedly increase their cellular concentration as a consequence of the inhibition. This poses limitations, such as the need to use high inhibitor concentrations, which can lead to off-target effects and cytotoxicity, and incomplete blockade of enzyme activity. Moreover, E3 ligases are multi-domain and multi-subunit enzymes, and targeting an individual binding site leaves other scaffold scaffolding regions untouched and other interactions functional. As a result, E3 ligase inhibition may be ineffective or fail to recapitulate genetic knockout or knockdown. New chemical modalities to target E3 ligases are therefore demanded.

E3 ligases are not merely targets for inhibition. Compounds of natural or synthetic origin have been discovered that bind to E3 ligases and promote the recruitment of new proteins. These interfacial compounds induce de novo formation of ligase-target PPIs effectively hijacking E3 ubiquitination activity towards the neo-substrates, for targeted protein degradation. One class of small molecule hijackers of E3 ligase activity comprises monovalent compounds. These so-called "molecular glues" include the plant hormone auxin, which binds to the Cullin RING ligase (CRL) CRL1-TIR1 to target transcriptional repressor proteins of the Aux/IAA family, and the immunomodulatory drugs (IMiDs) thalidomide, lenalidomide, pomalidomide and analogue CC-885, that all bind to cereblon (CRBN), a subunit of the CRL4-CRBN ligase, and redirect CRBN activity to different substrates.[4-10] More recently, the sulfonamide anticancer drug indisulam was found to induce degradation of the splicing factor RBM39 via recruiting CRL4-DCAF15 activity. A distinct class of compounds that display a similar mechanism of action are bivalent molecules called Proteolysis-Targeting Chimeras (PROTACs). PROTACs comprise of a first warhead moiety for a ligase, and a second warhead for a target protein, joined by a linker.[11] Formation of a ternary complex between the PROTAC, the ligase and the target triggers proximity-induced target ubiquitination and degradation. Warhead ligands have been used to develop potent and cell-active PROTACs recruiting different ligases, including CRL2-VHL,[12-15] CRL4-CRBN,[16-20] and IAPs.[21-22] Amongst the targets successfully degraded by PROTACs are BET proteins Brd2, Brd3, and Brd4,[12,14-17] FKBP,[16,20] protein kinases,[13,18] amongst others[13,21] An attractive feature of PROTACs is their sub-stoichiometric catalytic activity,[13] which does not require full occupancy of the target-binding site as with conventional inhibitors, leading to degrading concentrations that can be orders of magnitude lower than the inhibitory concentrations of their constitutive parts alone. Furthermore, induced target depletion can have a more sustained cellular effect compared to target inhibition, and can overcome compensatory cellular feedback mechanisms, such as increase in target levels. Crucially, it has been shown that PROTAC molecules can exhibit an added layer of selectivity for protein degradation beyond the intrinsic binding selectivity of the warhead ligand[12,15,18] Our recent structural work with Brd4-selective PROTACs targeting CRL2-VHL revealed that the importance of specific ligand-induced PPIs between the ligase and the target, which contribute to cooperative formation of stable and highly populated ternary complexes.[15]

The inventors have now found that it is possible to target E3 ligases themselves for ubiquitination and proteasomal degradation, using a suitably designed PROTAC. For at least some aspects the inventors have found that a PROTAC comprising two instances of an E3 binding moiety may be capable of forming ternary complexes in which the same E3 functions as both ubiquitinating enzyme and neo-substrate.

SUMMARY OF THE INVENTION

According to a first aspect of the invention there is provided a compound having the structure:

A-L-B wherein A and B are independently an E3 ubiquitin ligase protein binding ligand compound of formula 1A or 1B:

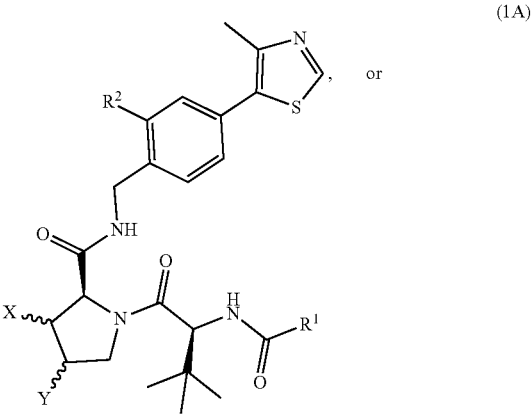

(1A)

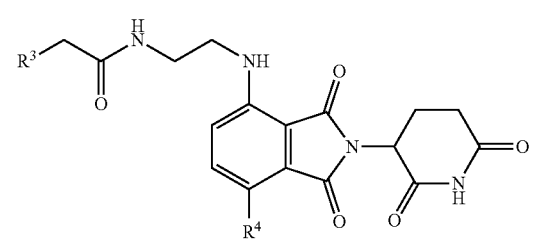

(1B)

wherein L is a linking group which is directly bonded to the compound of formula 1A at $R^1$ or $R^2$, and/or directly bonded to the compound of formula 1B at $R^3$ or $R^4$ and wherein L is $-R^5-[O(CH_2)_m]_n-R^6-$, wherein m and n are independently 0 to 10, and $R^5$ and $R^6$ are independently selected from the group: covalent bond, C1-C10 alkylene, $-OR^7-$, C1-C10 polyether, or $-O-$;

wherein $R^1$ is selected from either the group: (1) a covalent bond, or C1-C5 alkylene when L is bonded to the compound of formula 1A at $R^1$, or the group (2) H, $NH_2$, C1-C5 alkyl, or $C(CN)C_2H_4$ when L is bonded to the compound of formula 1A at $R^2$;

wherein $R^2$, $R^3$, and $R^4$ are independently selected from the group: a covalent bond, H, $NH_2$, C1-C5 alkyl, $C(CN)C_2H_4$;

wherein X and Y are independently selected from the group: H, OH or halogen;

and wherein $R^7$ is C1-C5 alkylene, or a pharmaceutically acceptable salt, hydrate, solvate or polymorph thereof.

Accordingly, the compound of formula A-L-B may comprise a compound of either formula 1A or 1B connected via the linker L to a compound of either formula 1A or 1B. In embodiments where A and/or B is a compound of formula 1A, the compound of formula 1A may be connected to the linker L via $R^1$ or $R^2$. In embodiments where A and/or B is a compound of formula 1B, the compound of formula 1B may be connected to the linker L via $R^3$ or $R^4$.

Compounds having the general formula A-L-B as described herein may be referred to in the description below as "PROTAC-compounds", "HOMO-PROTAC compounds" (wherein the moiety A is the same as the moiety B), "Hetero-PROTAC compounds" (wherein the moiety A is different to moiety B), or simply as "compounds of the invention".

The inventors have surprising found that the compounds having the structure A-L-B as defined above are able to induce degradation of E3 ubiquitin ligase protein within a cell by using the E3 ubiquitination mechanism itself. Accordingly, it suggested that the compounds of structure A-L-B forms a tertiary structure with two E3 ubiquitin ligase proteins such that one E3 ubiquitin ligase protein ubiquitinates another E3 ubiquitin ligase protein to which it is joined by the compound of structure A-L-B. It is further suggested that this ubiquitination is induced due to the enforced close proximity of the two E3 ubiquitin ligase proteins in the tertiary structure formed by binding of the E3 ubiquitin ligase proteins with the compounds of formula 1A or 1B.

Furthermore, it has been found that the compounds of the invention are able to initiate the degradation at sub-stoichiometric concentrations, thereby indicating that the compounds are at least partially catalysing the degradation.

In some embodiments X may be H or halogen.

In embodiments where X is a halogen, X may be selected from F, Cl, Br, or I. For example, X may be selected from F or Cl. X may be F.

In some embodiments, Y may be OH. Typically, Y is in the "down" position as illustrated in formula 1C below.

In embodiments where either A or B is a compound according to formula 1A, A or B may have the formula 1C:

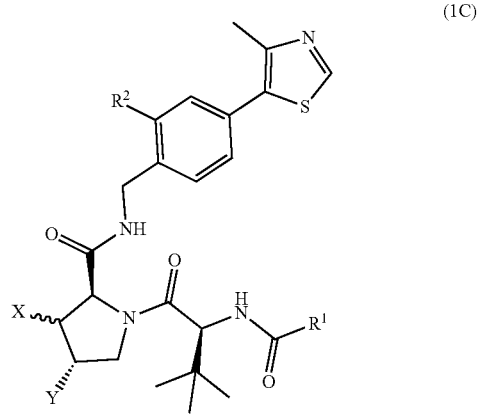

(1C)

In some embodiments, A may be a compound of formula 1A and B may be a compound of formula 1A.

L may be connected to A via $R^1$ of formula 1A. L may be connected to B via $R^1$ of formula 1A.

Alternatively, L may be connected to A via $R^2$ of formula 1A and L may be connected In some embodiments, $R^5$ may be a chemical bond, $R^6$ may be a chemical bond, m may be 2 and n may be 3, 4 or 5.

In some preferred embodiments, n is 5.

The compound of some embodiments may have formula 2, 3 or 4:

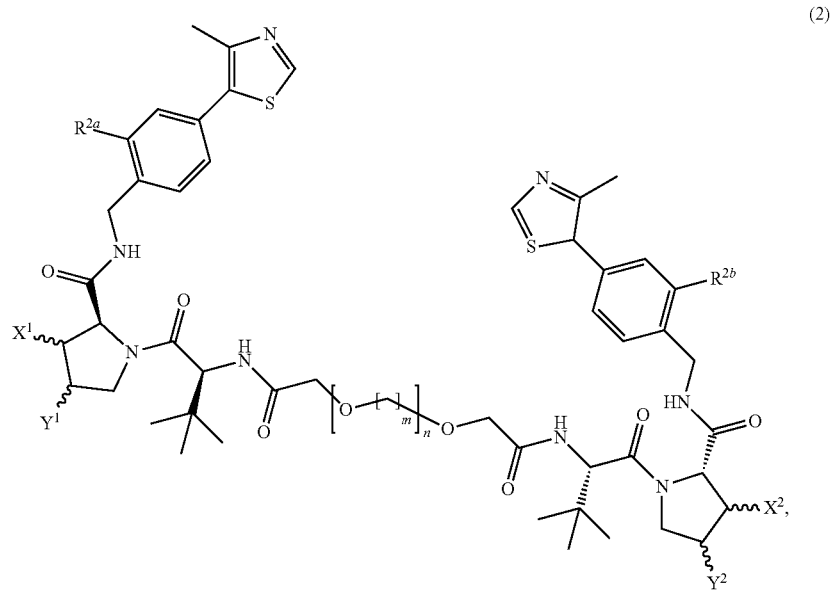

(2)

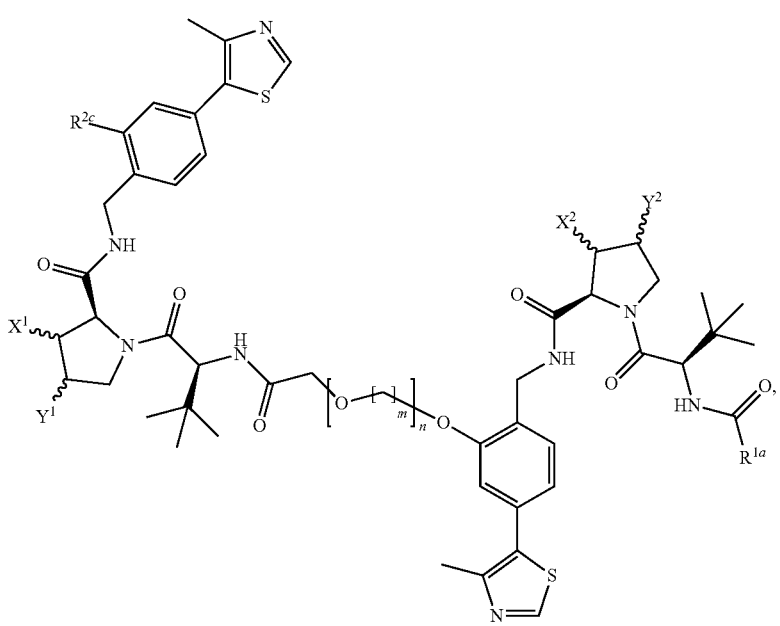

(3)

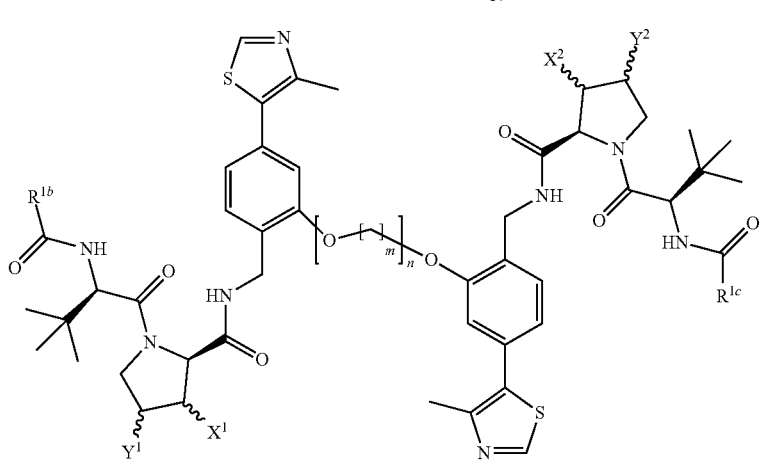

(4)

wherein $R^{2a}$, $R^{2b}$ and $R^{2c}$ are independently selected from H, $NH_2$, C1-C5 alkyl, and $C(CN)C_2H_4$;
$R^{1a}$, $R^{1b}$ and $R^{1c}$ are independently selected from H, $NH_2$, C1-C5 alkyl, and $C(CN)C_2H_4$;
$X^1$ and $X^2$ are independently selected from H, OH, halogen;
$Y^1$ and $Y^2$ are independently selected from H, OH, halogen; and
m and n are independently 0 to 10.

Preferably for compounds of formula 2, 3 or 4, n is 3-5. Typically, m is 1-4. Preferably, m is 2 such that the linker is formed of polyethylene glycol subunits.

In embodiments, $R^1$, $R^{1b}$ and $R^{1c}$ may be independently selected from C1-C5 alkyl or $C(CN)C_2H_4$. In further embodiments, $R^{1a}$, $R^{1b}$ and $R^{1c}$ may be independently selected from C1 alkyl (i.e. methyl or Me) and $C(CN)C_2H_4$.

In some embodiments $R^{2a}$, $R^{2b}$ and $R^{2c}$ may be H.

In some embodiments, $Y^1$ and $Y^2$ may be OH, $X^1$ and $X^2$ may be H, $R^{1a}$, $R^{1b}$ and $R^{1c}$ may independently be Me or $C(CN)C_2H_4$ and $R^{2a}$, $R^{2b}$ and $R^{2c}$ may be H.

In preferred embodiments the linker L is a linear chain of 12-20 atoms in length. The compounds of the invention have been found to be most useful to induce degradation of target proteins when the groups A and B are spaced apart. Accordingly, without wishing to be bound by theory, it has been found that a linker L being a linear chain of 12-20 atoms in length spaces the groups A and B apart a sufficient distance to allow them to bind to their target binding sites without interfering with one another, whilst at the same time ensuring that the target proteins are held in sufficient proximity that the E3 ubiquitin ligase protein bound to either or both A and B can ubiquitinate the target protein, thereby marking that protein for subsequent degradation by the cell's machinery.

L may be a linear chain of 15-18 atoms in length. For example, L may be a linear chain of 15, 16, 17 or 18 atoms in length.

Typically, the linker chain may comprise carbon and/or oxygen atoms. For example, the linker chain may comprise alkylene groups and/or ether groups and/or polyether groups.

Alternatively, the linker chain may be a peptide chain, or nucleotide chain, for example.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Examples of pharmaceutically acceptable salts suitable for use herein include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange.

Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulphonate.

In a preferred aspect herein the compounds of formula I for use in the PROTAC compounds of structure A-L-B— as defined herein are represented as a defined stereoisomer. The absolute configuration of such compounds can be determined using art-known methods such as, for example, X-ray diffraction or NMR and/or implication from starting materials of known stereochemistry.

Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers which are substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates as detailed herein may be obtained by the application of art-known procedures. For instance, enantiomers may be separated from each other by the selective crystallization of their diastereomeric salts with optically active acids or bases. Examples thereof are tartaric acid, dibenzoyl, tartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo-specifically. Preferably, if a specific stereoisomer is desired, said compound is synthesized by stereospecific methods of preparation. These methods will advantageously employ enantiomerically pure starting materials.

The diastereomeric racemates of the compounds of formula 1A or 1B for use in the PROTAC compounds of structure A-L-B as defined herein can be obtained separately by conventional methods. Appropriate physical separation methods that may advantageously be employed are, for example, selective crystallization and chromatography, e.g. column chromatography.

According to a second aspect of the invention there is provided a compound selected from the following group:

(5)

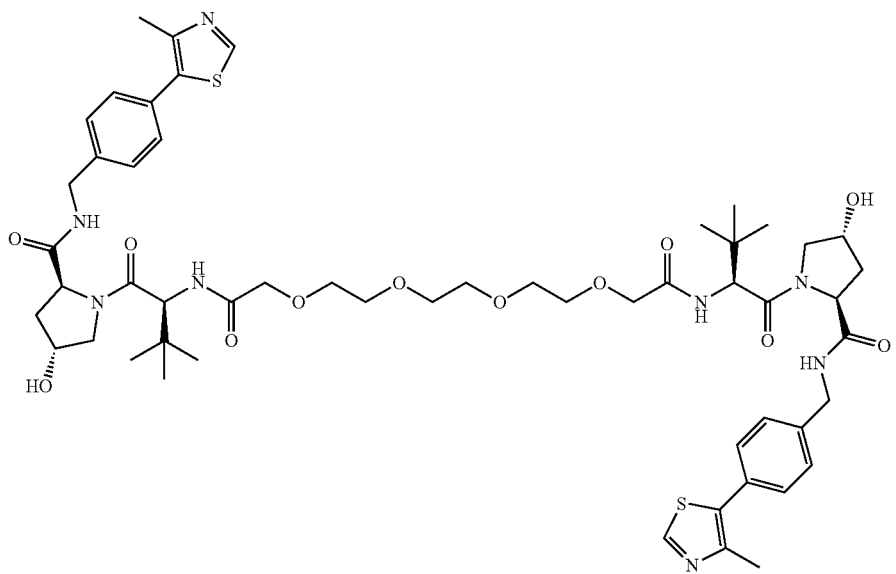

CM09

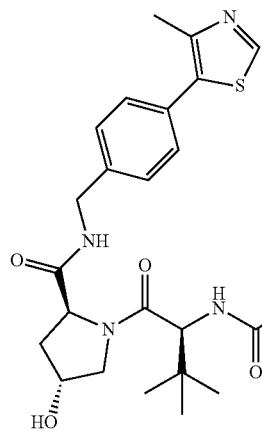
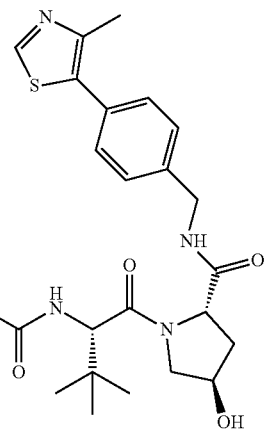
(6)
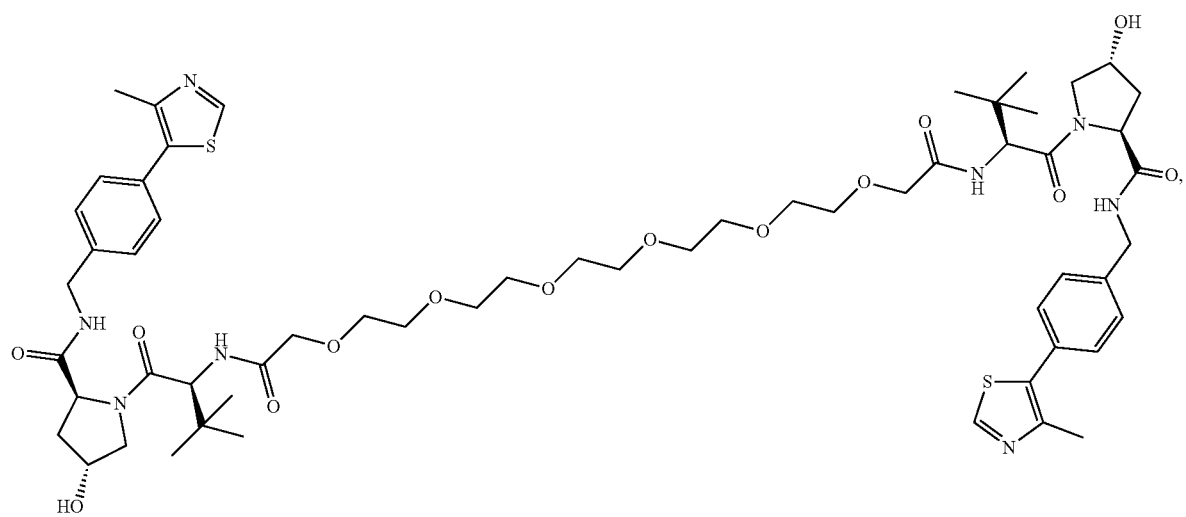
CM10
(7)
CM11
(8)
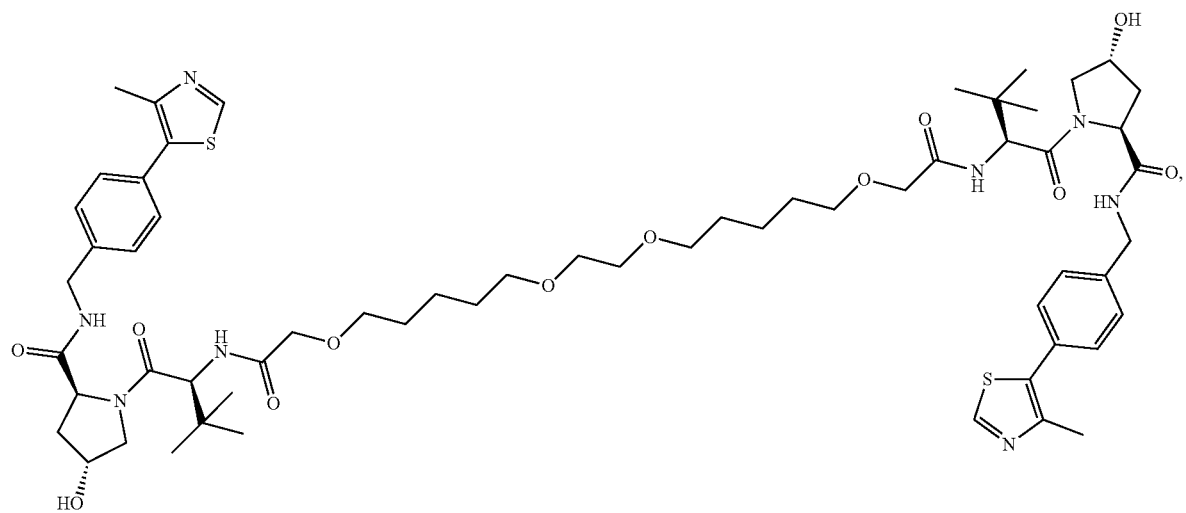

-continued
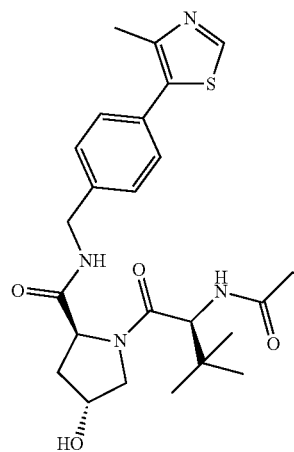 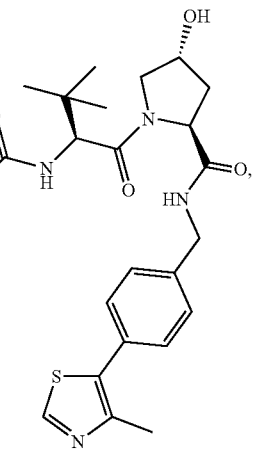
(9)
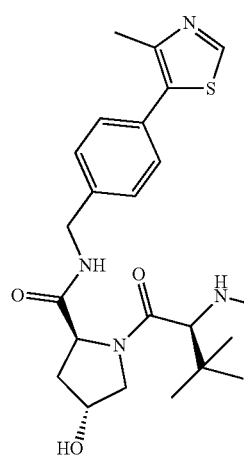 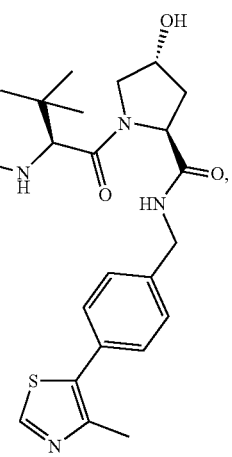
(10)
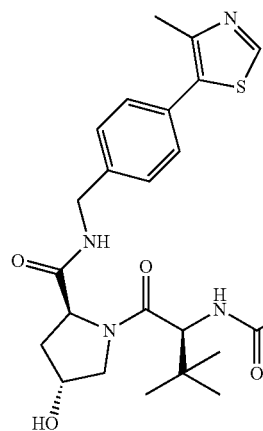 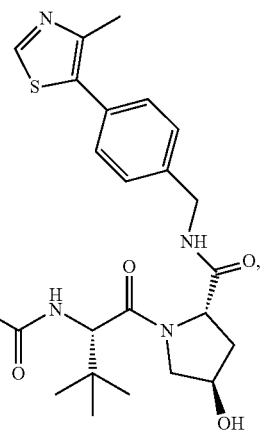
(11)

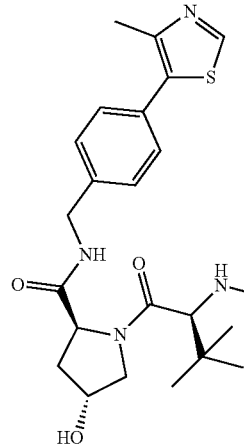
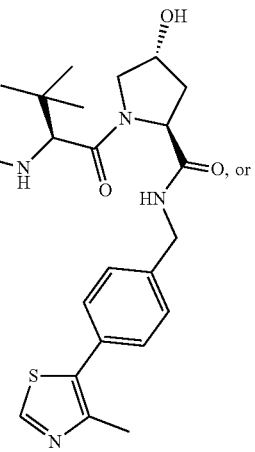

(12)

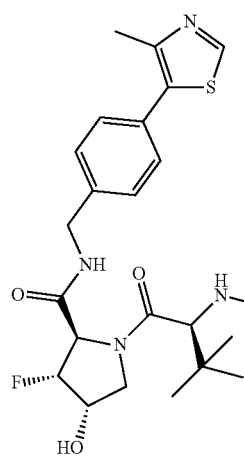
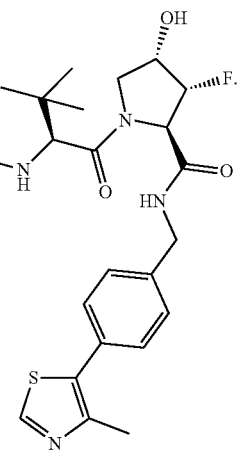

(13)

In a preferred embodiment, the compound is selected from the group of compounds (7) to (13). For example, the compound may be compound (7).

The invention extends in a third aspect to a pharmaceutical composition comprising one or more compounds according to the first or second aspect and a pharmaceutically acceptable vehicle or diluent therefor.

PROTAC compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a PROTAC compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a PROTAC compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present invention comprise a therapeutically effective amount of a PROTAC compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type.

The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Compositions for rectal or vaginal administration are preferably suppositories which can be prepared by mixing the PROTAC compounds of the invention with suitable non-irritating excipients or carriers such as cocoa butter, polyethylene glycol or a suppository wax which are solid at ambient temperature but liquid at body temperature and therefore melt in the rectum or vaginal cavity and release the active compound. Solid compositions of a similar type may also be employed as fillers in soft and hard-filled gelatine capsules using such excipients as lactose or milk sugar as well as high molecular weight polyethylene glycols and the like.

The PROTAC compounds can also be provided in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the PROTAC compounds of this invention, excipients such as lactose, talc, silicic acid, aluminium hydroxide, calcium silicates and polyamide powder, or mixtures of these substances. Sprays can additionally contain customary propellants such as chlorofluorohydrocarbons. Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In a fourth aspect, the invention provides a PROTAC compound of structure A-L-B as defined herein for use as a medicament.

In a fifth aspect of the invention there is provided a method of use of a compound according to any of the first or second aspect or a pharmaceutical composition according to the third aspect for the treatment of at least one of anaemia due to chronic kidney disease[23], anaemia due to cancer chemotherapy[24], ischemia[25], ischemic reperfusion injuries[26], myocardial infarction[27], stroke[27], acute lung injury[28], intestinal inflammation[29], wound healing[30] and post-transplantation complications[31], mitochondrial respiratory chain dysfunctions[32] and oncological conditions treatable by enhancing T-cell responses[33].

According to a sixth aspect of the invention there is provided a method of regulating activity of a target protein in a subject comprising administering to said subject a therapeutically effective amount of a compound according to the first or second aspect, or a pharmaceutical composition according to the third aspect.

The term "subject" as used herein refers to a mammal. A subject therefore refers to, for example, dogs, cats, horses, cows, pigs, guinea pigs, and the like. Preferably the subject is a human. When the subject is a human, the subject may also be referred to herein as a patient.

The term "therapeutically effective amount" means an amount effective to treat, cure or ameliorate a disease, condition illness or sickness.

Preferably, the target protein is an E3 ubiquitin ligase protein. Typically the E3 ubiquitin ligase protein is selected from CRL2-VHL, CRL4-CRBN. The E3 ubiquitin ligase protein may be selected from any of the >230 cullin RING ligases, for example CRL1-Skp2, CRL1-bTrCP, CRL1-Fbw, CRL1-Fbxo, CRL1-Fbxl, CRL2-LRR1, CRL2-FEM1, CRL3-Keap1, CRL3-KLHL, CRL3-SPOP, CRL4-DDB2, CRL4-DCAF, CRL4-CSA, CRL4-CDT2, CRL5-SOCS, CRL5-ASB. Other E3 ubiquitin ligase proteins may be selected from MDM2, c-Cbl, APC-C, FANCL, UBE3A, UBE3B, UBE3C, UBE3D, Parkin, SIAH, XIAP, UHRF1, TRAF6, PELI2, RNF2, RNF4 amongst others.

Preferred and optional features of the first to sixth aspects may be preferred and optional features of the other of the first to sixth aspects as appropriate.

BRIEF DESCRIPTION OF THE FIGURES

Embodiments of the present invention will now be described, by way of non-limiting example, with reference to the accompanying drawings.

DETAILED DESCRIPTION

Figure 1:
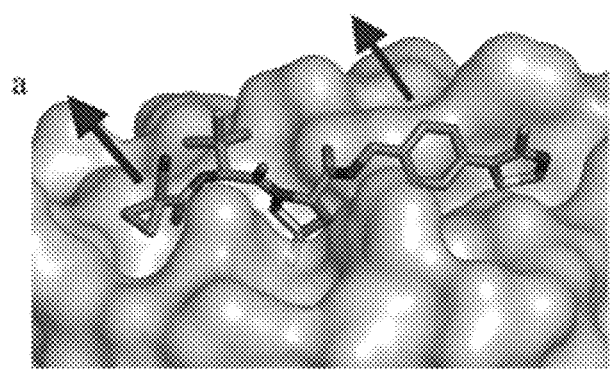
FIG. 1: (a) Crystal structures of VHL in complex with VH298 (PDB code 5LLI). VHL is shown in surface representation and the bound ligand as sticks representation. (b) Chemical structure of VHL inhibitors VH032 and VH298.
Figure 1:
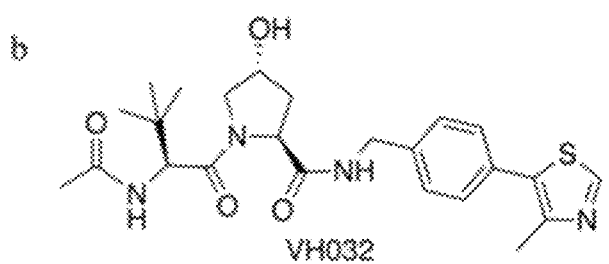
Figure 1:
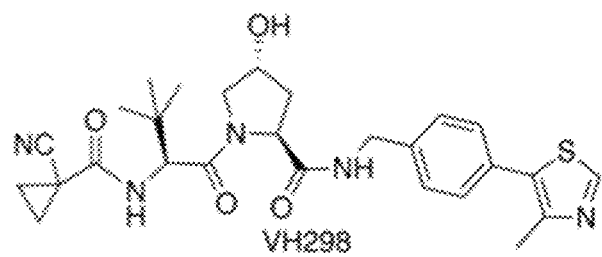

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Biology

Human cell lines HeLa, U2OS and HEK 293, purchased from ATCC, were propagated in DMEM supplemented with 10% fetal bovine serum (FBS), L-glutamine, 100 μg ml$^{-1}$ of penicillin/streptomycin at 37° C. and 5% $CO_2$. Cells were maintained for no more than 30 passages. All cell lines were routinely tested for *mycoplasma* contamination using MycoAlert kit from Lonza.

Small Interfering RNA.

For siRNA inhibition studies, $3\times10^5$ cells were seeded into each well of a 6-well plate in order to achieve 70% of confluence on the day of transfection. siRNA (SMARTpool: ON-TARGETplus VHL siRNA L-003936-00-0005) was prepared as a 20 μM solution in RNase-free 1× siRNA buffer. Negative control siRNA (siRNA from Life Technologies, cat. #4390843) was used as negative control. On the day of transfection, old medium was replaced with fresh one. siRNA solution (5 μL) of both VHL targeting siRNA and negative control were added to 250 μL of Opti-mem in 1.5 mL tube. This solution was prepared in duplicate. The content in each tube was mixed by pipetting. Lipofectamine RNAiMax (5 μL) was added to 250 μL of Opti-mem in another 1.5 mL tube. The solution was prepared in duplicate. The content in each tube was mixed by pipetting. The solution from step 2 was added to the tube in step 3. The solution was mixed by brief vortex ad incubated at r.t. for 20 min. The tubes were centrifuged briefly. The whole volume of transfection mix was added to the 6-well plate. Plate was swirled gently back and forth to mix the content. Plates were incubated at 37° C. and 5% $CO_2$ for 48 h before harvesting.

Single Point Treatment.

For single time point treatment experiments, cells were transferred in 6-well plates with $5\times10^5$ cells per well in 2 ml media in order to achieve 80% confluence the following day. Stock concentrations of compounds were prepared by solubilizing the powder in 100% v/v DMSO to the final desired stock concentration.

On the day of treatment, all compound samples were prepared as 100-fold concentrated compound solution using DMEM just before treatment. The experiment samples (20 μL) were added to the 6 well plate containing 2 ml of media. The final DMSO concentration was 0.1% v/v. Cells were incubated at 37° C. and 5% $CO_2$ for the desired time before harvesting.

Time Course Experiments.

For time dependent treatment, cells were transferred in 6-well plates with $3\times10^5$ cells per well in 2 ml media. Samples were prepared as detailed above or the single time point experiments. Treatment was conducted at given time points prior to harvest.

ML4924 and MG132 Treatment.

Cells were transferred in 6-well plates with $5\times10^5$ cells per well in 2 ml media in order to achieve 80% confluence the day after. At t=0, MLN4924 was added into the desired wells at 3 μM final concentration and 0.1% v/v of DMSO. DMSO (0.1% v/v final conc.) was added to the remaining wells in order to match identical conc. of vehicle in all wells. At t=3 h, MG 132 was added into the desired wells at 50 μM final conc. and 0.1% v/v of DMSO. DMSO (0.1% v/v final conc.) was added to the remaining wells in order to achieve the same conc. of vehicle in all the wells. At t=3.5 h, the desired wells were treated with 1 μM of CM11 in 0.1% v/v DMSO final concentration. DMSO (0.1% v/v final conc.) was added to the remaining wells in order to obtain the same conc. of vehicle in all the wells. The total final concentration of DMSO was therefore 0.3% v/v. Plates were incubated for 4 h at 37° C. and 5% $CO_2$ before harvesting.

Competition Experiments with VH032.

Cells were transferred in 6-well plates with $5\times10^5$ cells per well in 2 ml media in order to achieve 80% confluence the day after. On the day of experiment, cells were treated with VH032 at the final conc. of 150 μM for 30 min prior to treatment with CM11 at 1 μM final concentration for 4 h. Plates were incubated for the desired time at 37° C. and 5% $CO_2$ before harvesting.

Co-Treatment with IOX4 and CM11 to Investigate Upstream Effect Experiment.

For this experiments, cells were transferred in 6-well plates with $5\times10^5$ cells per well in 2 ml media in order to achieve 80% confluence the day after. On the day of experiment, cells were treated with IOX4 at the final concentration of 50 μM for 30 min prior to treatment with CM11 at 1 μM final concentration for 4 h. Plates were incubated for the desired time at 37° C. and 5% $CO_2$ before harvesting.

Immunoblotting.

Cells were lysed in lysis buffer (20 mM Tris pH 8, 150 mM NaCl, 1% Triton x100) and a protease inhibitor cocktail (Roche) per 10 ml buffer. For protein extracts, the dishes were placed on ice. The media was aspirated and the tissue layer washed twice with ice-cold phosphate buffer saline (PBS). Lysis buffer (120 μl) was added and the cells detached from the surface with a cell scraper. After removal of the insoluble fraction by centrifugation, the protein concentration of the supernatant was determined by Pierce™ Coomassie (Bradford) Protein Assay Kit. Protein extracts were fractionated by SDS-PAGE on 4-12% Tris-Acetate NuPage® Novex® (Life Technologies) polyacrylamide gels and transferred to a nitrocellulose membrane using wet transfer. The membrane was then blocked with 5% w/v Bovine serum albumin (BSA) in Tris-buffered saline (TBS) with 0.1% w/v Tween-20. For detecting proteins the following primary antibodies in the given concentrations were used: anti-β-Actin (Cell Signaling Technology, 4970S, 13E5) 1:2000, anti-VHL (Cell Signaling Technology, #68547) 1:1000, anti-Hif-1α (BD Biosciences, 610959, clone 54) 1:1000, anti-hydroxy-HIF-1α (Hyp564) (Cell Signaling Techonology; #3434) 1:1000, anti-PHD2 (Bethyl Laboratories; A300-322A) 1:1000, anti-PHD3 (Bethyl Laboratories; A300-327A) 1:1000, anti-CRBN (Proteintech; 11435-1-AP) 1:1000.

Following incubation with a horseradish peroxidase-conjugated secondary antibody (Cell Signaling Technology), the signal was developed using enhanced chemiluminescence (ECL) Western Blotting Detection Kit (Amersham) on Amersham Hyperfilm ECL film (Amersham).

Band quantification was performed using ImageJ software and reported as relative amount as ratio of the each protein band relative to the lane's loading control. The values obtained were then normalized to 0.1% DMSO vehicle control.

Luciferase Assay.

It was performed essentially as described by Frost et al.[34] Briefly, cells (HeLa and U2OS) stably expressing an HRE-luciferase reporter were treated for the indicated times with compounds. Cells were harvested in passive lysis buffer (Promega) and subjected to three freeze-thaw cycles. The soluble lysate fraction was used for assays, performed according to the manufacturer's instructions (Promega) using a Berthold Lumat LB 9507 Luminometer. Results were normalized for protein concentration, and reported as mean±s.e.m. from three biological replicates.

Quantitative Real-Time PCR.

It was performed essentially as described by Frost et al.[34] Briefly, RNA was extracted from HeLa cell lysates using the RNeasy Mini Kit (Qiagen) and reverse transcribed using the iScript cDNA Synthesis kit (Bio-Rad). Real-time PCR was performed using PerfeCTa SYBR Green FastMix (Quanta Biosciences) in C1000 Touch Thermal Cycler (Bio-Rad). mRNA levels were calculated based on averaged Ct values from two technical replicates, normalized to mRNA levels of β-actin, and reported as mean±s.e.m. from three biological replicates.

Biophysical Assays

Isothermal Titration Calorimetry (ITC).

Titrations were performed on an ITC200 micro-calorimeter (GE Healthcare). PROTACs (CM11, CMP98 or CMP99) were diluted from a 100 mM DMSO stock solution to 150 μM in a buffer containing 20 mM Bis-tris propane, 150 mM NaCl, 1 mM tris(2-carboxyethyl)phosphine (TCEP), pH 7.4. The final DMSO concentration was 0.15% v/v. VBC protein experiments were carried out in a buffer containing 20 mM Bis-tris propane, 150 mM NaCl, 1 mM TCEP, 0.15% v/v DMSO, pH 7.4. The titrations consisted of 19 injections of 2 μL compounds solution (150 μM, in the syringe) at a rate of 2 s/μL at 120 s time intervals into the VCB protein solution (20 μM, in the cell). An initial injection of compound solution (0.4 μL) was made and discarded during data analysis. All experiments were performed at 25° C., whilst stirring the syringe at 600 rpm. The data were fitted to a single binding site model to obtain the stoichiometry n, the dissociation constant $K_d$ and the enthalpy of binding ΔH using the Microcal LLC ITC200 Origin software provided by the manufacturer.

Size Exclusion Chromatography (SEC).

SEC experiments were carried out in a AKTA pure system (GE Healthcare) at room temperature. The oligomeric state of the VCB complex in solution was analyzed by gel filtration in a buffer containing 20 mM Bis-Tris (pH 7), 150 mM NaCl and 1 mM 1,4-dithiothreitol (DTT) using a Superdex 200 Increase 10/300 GL column (GE Healthcare) calibrated with globular proteins of known molecular weight (GE Healthcare, 28-4038-41/42). VBC protein (50 μM) was incubated with CM11 (30 μM), CMP98 (30 μM), CMP99 (30 μ£M), VH032 (30 μM) or DMSO (0.5%) for 20 min at room temperature prior to injection. Sample volume for each injection was 200 μL, and the flow rate was 0.5 mL/min. Peak elution was monitored using ultraviolet absorbance at 280 nm.

Biotinylation of VCB.

The VCB complex was mixed with EZ-link NHS-PEG$_4$-biotin (Thermo Scientific) in a 1:1 molar ratio and incubated at room temperature for 1 h. The reaction was quenched using 1 M Tris-HCl, pH 7.5, and unreacted NHS-biotin was removed with a PD-10 MiniTrap desalting column (GE Healthcare) equilibrated with 20 mM HEPES, pH 7.5, 150 mM NaCl and 1 mM DTT.

AlphaLISA assay.

All assays were performed at room temperature in 384-well plates with a final assay volume of 25 μL per well; plates were sealed with transparent film between addition of reagents. All reagents were prepared as 5× stocks diluted in 50 mM HEPES, pH 7.5, 100 mM NaCl, 0.1% (w/v) bovine serum albumin and 0.02% (w/v) 3-[(cholamidopropyl)dimethylammonio]-1-propanesulfonate (CHAPS). Biotinylated VCB (20 nM final) and Hiss-VCB (20 nM final) were incubated with a range of Homo-PROTAC concentrations (0.5 to 200 nM; three-in-five serial dilution) for 1 h. Anti-His acceptor beads (PerkinElmer, 10 μg/mL final) were added and plates were incubated for another hour. Streptavidin-coated donor beads (PerkinElmer, 10 μg/mL final) were added and plates were incubated for a final 1 h. Plates were read on a PHERAstar FS (BMG Labtech) using an optic module with an excitation wavelength of 680 nm and emission wavelength of 615 nm. Intensity values were plotted against PROTAC concentration on a logo scale.

Rational Design

Figure 2:
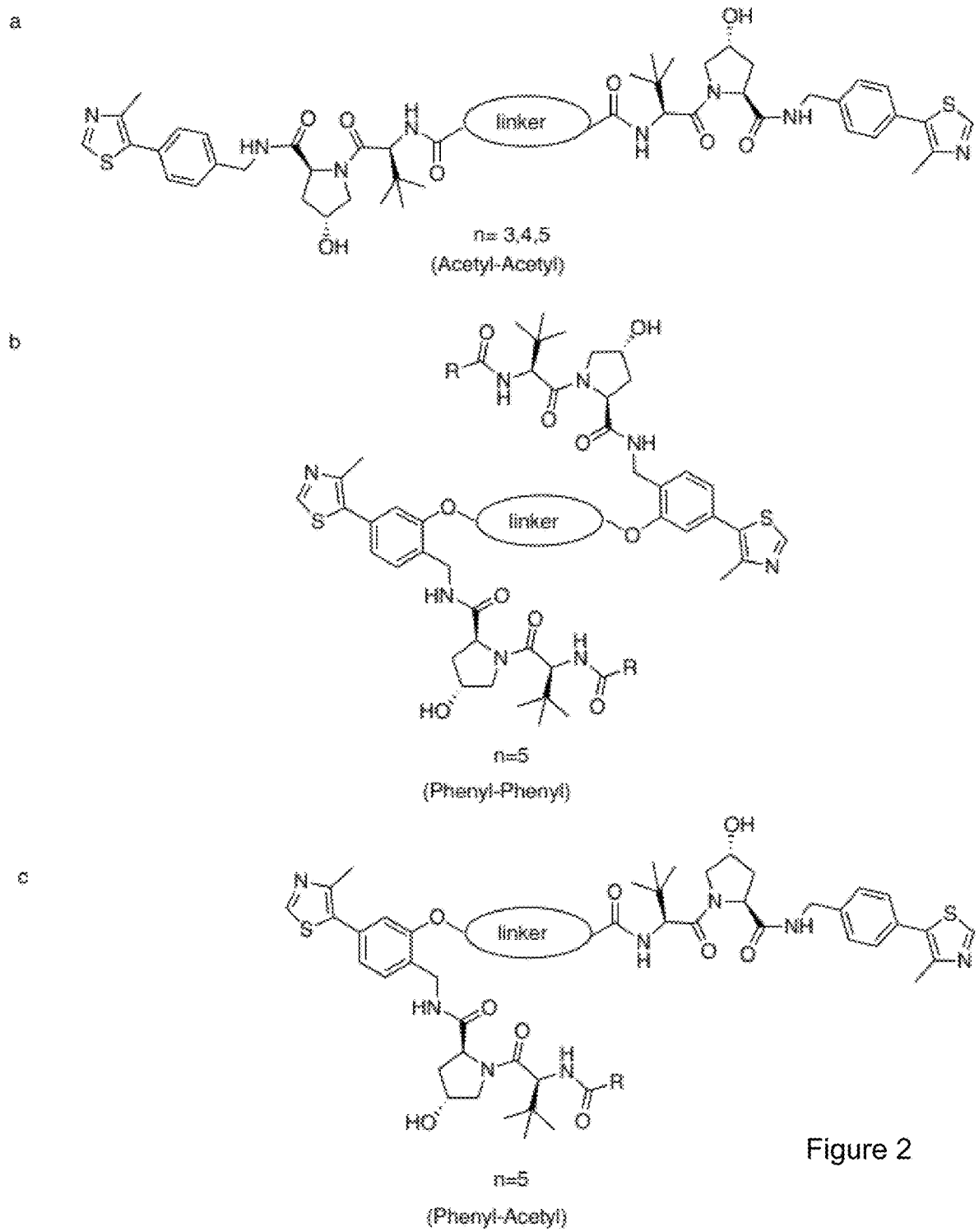
FIG. 2: General chemical structure and design of Homo-PROTACs compounds. Linkage sites at acetyl and phenyl group are indicated.
Figure 2:
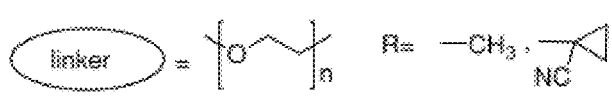

Design of VHL Homo-PROTACs began with careful consideration of the position of derivatization on two potent VHL ligands recently characterized by our group, VH032 and VH298 (FIG. 1b).[2,3] To retain the strong binding affinity that characterizes the ligand, co-crystal structures were analyzed to identify solvent exposed regions from where the ligands could be derivatized without perturbing their binding modes (FIG. 1a). This analysis and consideration of previous VHL-targeting PROTACs pointed to the methyl group of the left-hand side (LHS) terminal acetyl group of VH032 as a suitable point of connection for a linker.[12,13] A second solvent-exposed position available for derivatization was the phenyl group on the right-hand side (RHS), as previously employed with PROTACs targeting the Halotag.[35] To investigate the impact of derivatization, we designed three classes of Homo-PROTACS: a) symmetric via the LHS acetyl group of each ligand (FIG. 2a); b) symmetric via the RHS phenyl group (FIG. 2b); and c) asymmetric via the acetyl group in one warhead and the phenyl in the other (FIG. 2c). In the cases b and c, at the underivatized terminal LHS we decided to retain either an acetyl (as in VH032) or a cyano-cyclopropyl moiety (as in VH298), a modification that led to increased binding affinities, cell permeability and cellular activities in the context of the VHL inhibitor alone.[3] To evaluate the potential impact of linker length, linkers comprised of polyethylene glycol chains with either three, four or five ethylene glycol units were chosen to connect the two VHL ligands.

It is known that the trans epimer of Hyp is an absolute requirement for VHL binding, and that the corresponding cis epimer abrogates binding to VHL, both within the context of a native HIF substrate peptide,[36] and VHL ligands.[3,13] We therefore designed two different PROTACs based on the structure of the first series (FIG. 2a), with the aim to use them as controls: a cis-cis epimer, expected to be completely inactive, and a cis-trans epimer compound, expected to retain binding to a single VHL molecule in a 1:1 fashion, thus potentially acting as inhibitor but not as degrader.

Synthesis.

Figure 3:
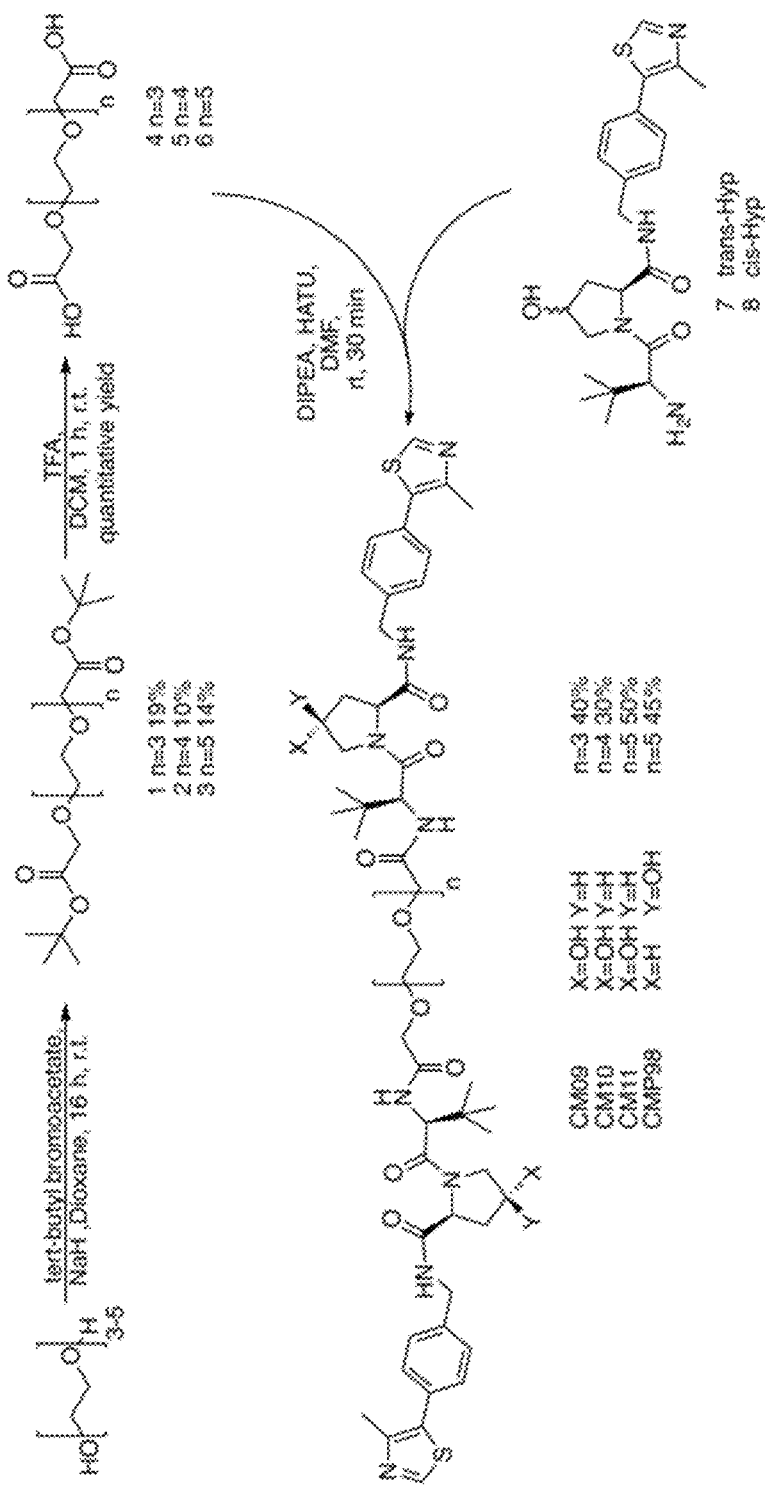
FIG. 3: Synthesis of Homo-PROTACs compounds symmetric from acetyl group CM09, CM10, CM11 and negative control compound CMP98.

For the synthesis of the first class of Homo-PROTACs (FIG. 2a), symmetric PEG linkers 4, and 6 bearing free carboxylate groups at either ends were obtained by reaction of tert-butyl bromoacetate with tri-, tetra- and penta-ethylene glycol in the presence of NaH in dioxane and followed, after purification, by treatment with 50% TFA in DCM (FIG. 3). The final compounds CM9, CM10 and CM11 were obtained by amide coupling of the VHL ligand 7 (prepared as previously described)[38] with linkers 4, 5 and 6, in a 2:1 ratio, respectively, in the presence of HATU as the coupling agent and DIPEA as the base (FIG. 3). For the synthesis of the symmetric cis-cis compound CMP98, compound 8 (ref. 38) was coupled with linker 6 to afford the desired product (FIG. 3).

Figure 4:
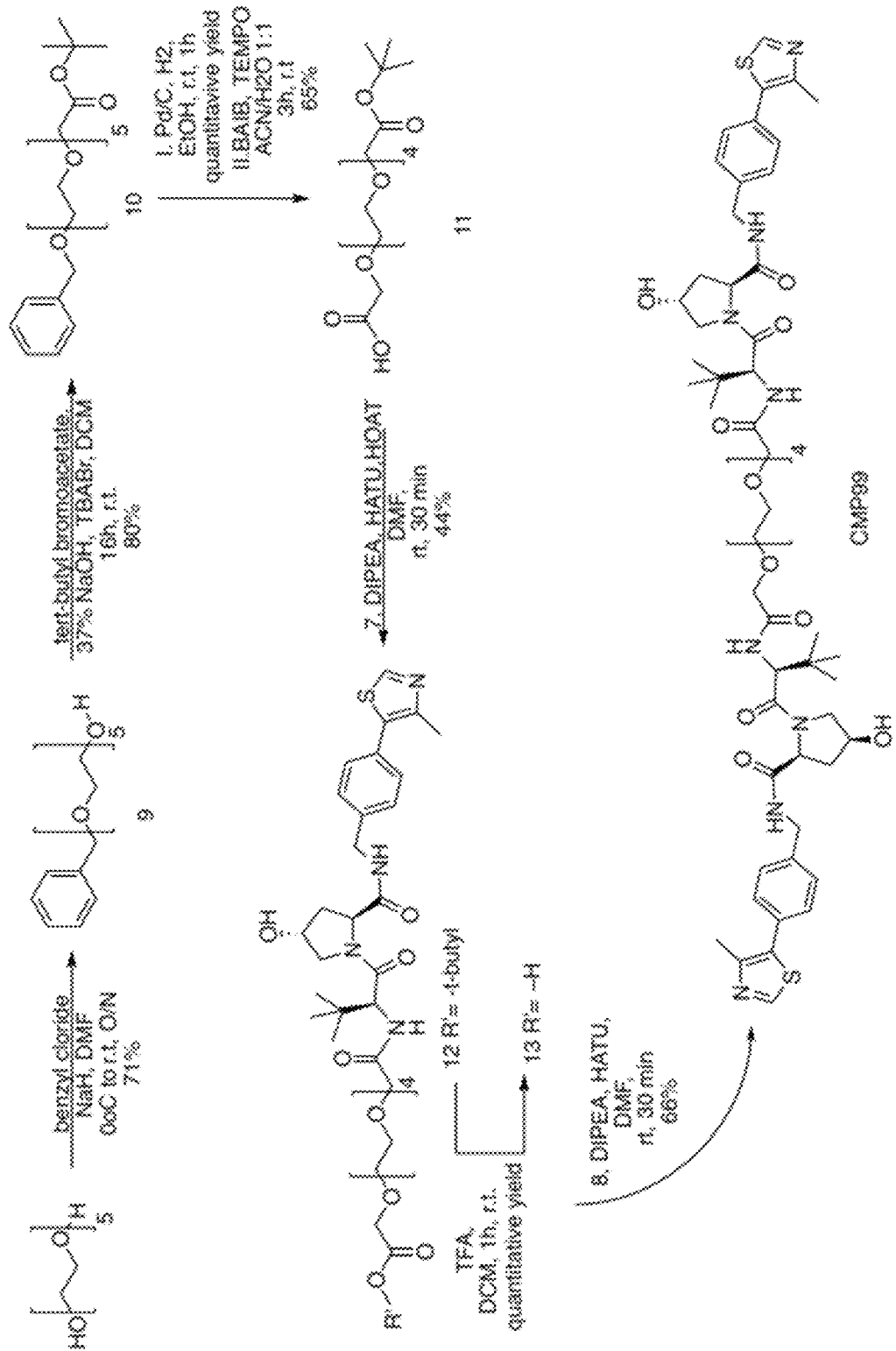
FIG. 4: Synthesis of negative control Homo-PROTAC compound CMP99 with cis-trans configuration.

For the preparation of the asymmetric cis-trans compound CMP99, a synthetic route toward the synthesis of the mono-protected di-carboxylate linker was established. Pentaethylene glycol was the linker of choice because of ease of purification compared to longer PEGs, and at the same time yielding a control compound of average linker length (PEG-4 in this case). Pentaethylene glycol was converted into monobenzyl ether 9 in 71% yield, which was reacted with tert-butyl bromoacetic acid under biphasic conditions (DCM/37% aq. NaOH and stoichiometric tetrabutyl ammonium bromide). After deprotection of the benzyl group by catalytic hydrogenation, formation of the carboxylic acid moiety was achieved by oxidation with TEMPO and bis-acetoxy iodobenzene (BAIB), delivering compound 11 in 65% yield (FIG. 4). Compound 7 was then coupled with linker 11 using the condition described above, affording compound 12. Deprotection of the tert-butyl group using TFA and subsequently coupling with 8 afforded CMP99 in 66% yield (FIG. 4).

Figure 5:
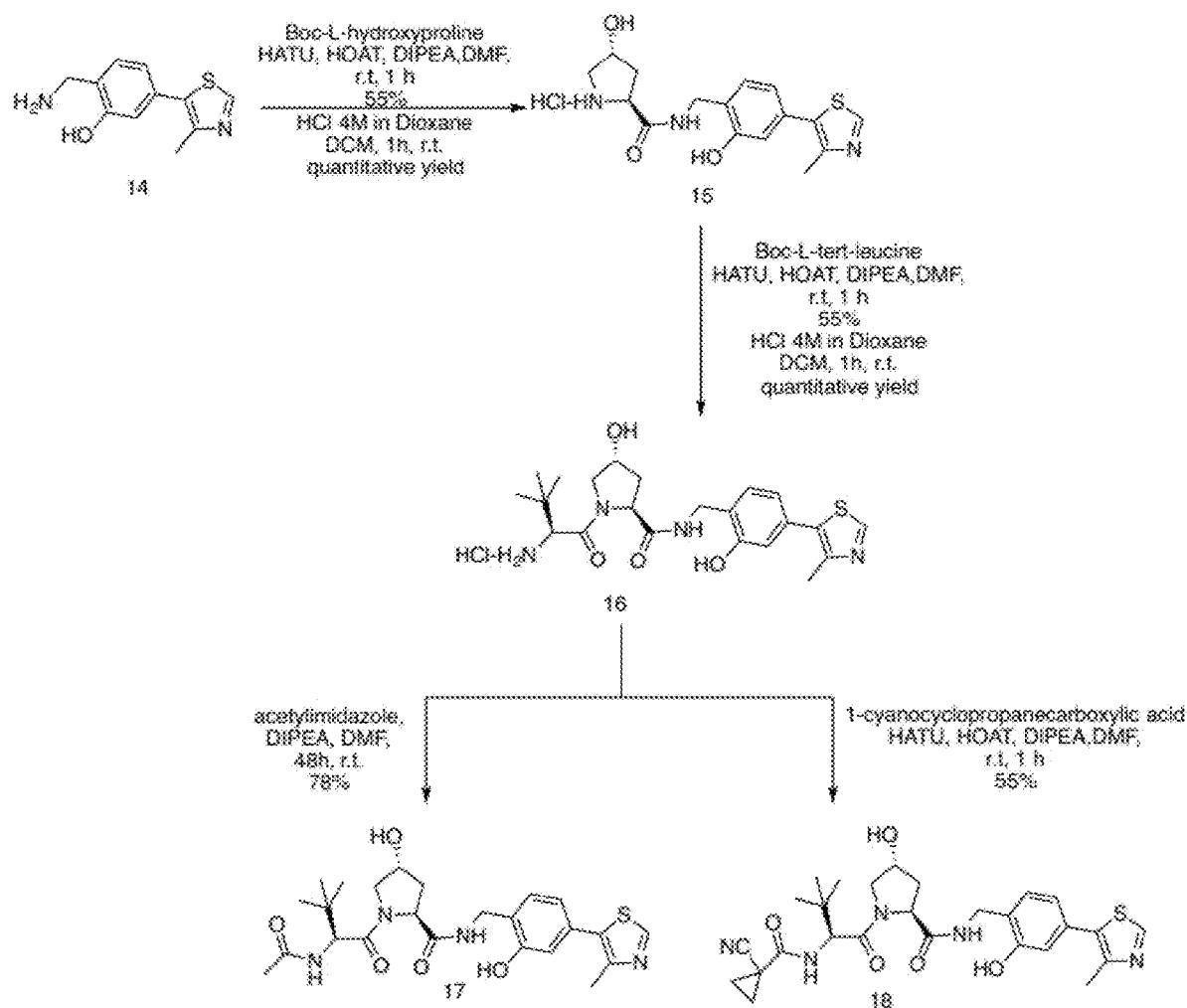
FIG. 5: Synthesis of VHL binding moieties 17 and 18

For the synthesis of the second class of symmetric Homo-PROTACs (FIG. 2b), it was decided to utilize compounds 17 and 18 as VHL warheads. Common precursor 16 was synthesized following a previously reported procedure,[35] with minor modification that led to yield and purity improvements (FIG. 5). Indeed, we observed that the use of HATU in combination with HOAT for the coupling steps of both Boc-L-Hyp and Boc-tert-leucine led to the formation of only the desired products, avoiding the formation of a bis-acylate secondary product,[54] instead prominent when HATU was used alone. Compound 17 or 18 were obtained by treatment of compound 16 with 1-cyanocyclopropanecarboxylic acid in presence of HATU, HOAT and DIPEA or acetylimidazole and TEA (FIG. 5). Synthesis of 17 was also performed using acetic anhydride, but during this reaction it was observed the formation of a secondary product di-acetylated, not only at the desired position but also at the hydroxyl group of the phenyl ring, which could however be separated.

Figure 6:
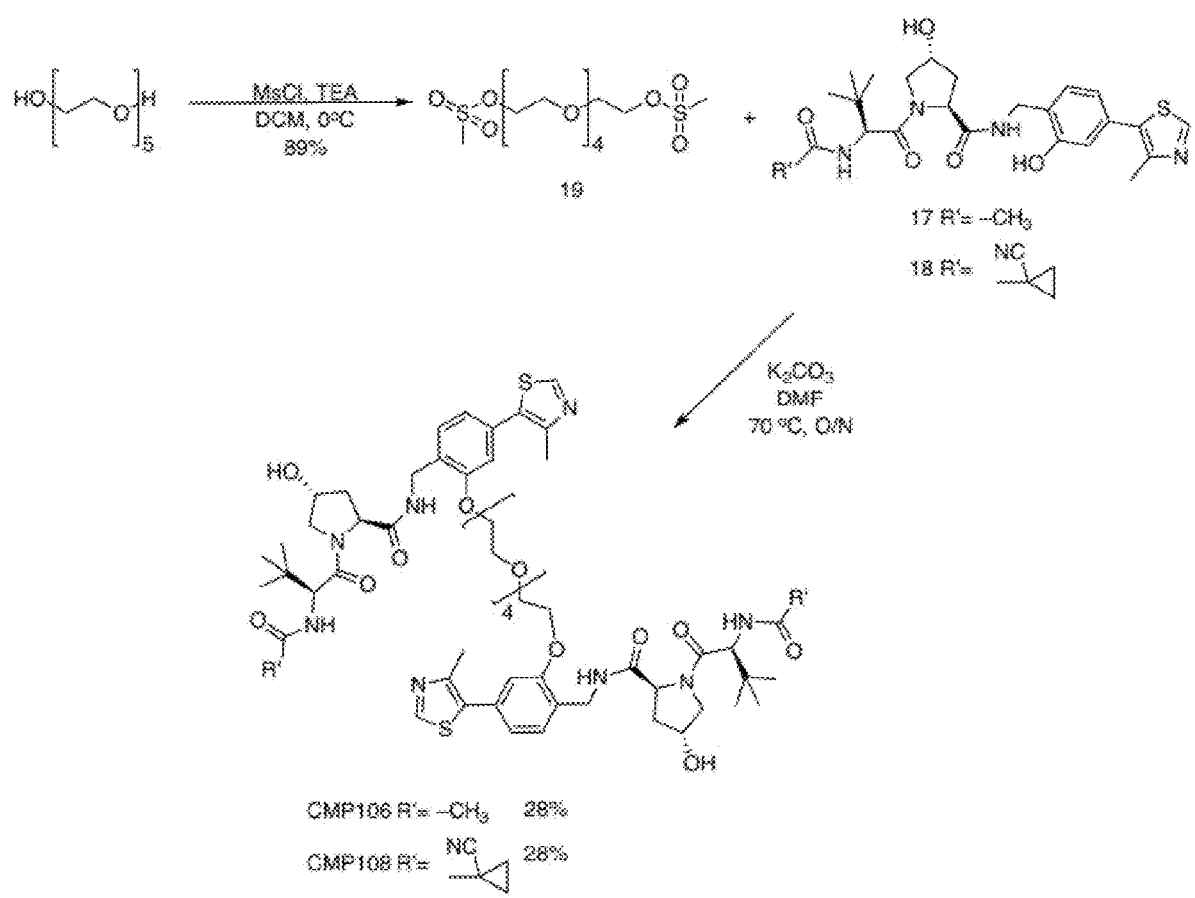
FIG. 6: Synthesis of Homo-PROTACs CMP106 and CMP108 symmetrically derivatized from the phenyl group.

The PEG linkers for this class of compound were designed to contain a methanesulfonate group at either end, which could be coupled in a single step with the phenol of the VHL ligand. Linker 19 was prepared by mesylation of pentaethylene glycol and reacted with either compounds 17 or 18 in a 1:2 ratio in the presence of $K_2CO_3$ to afford CMP106 and CMP108, respectively, in good yield (FIG. 6).

Figure 7:
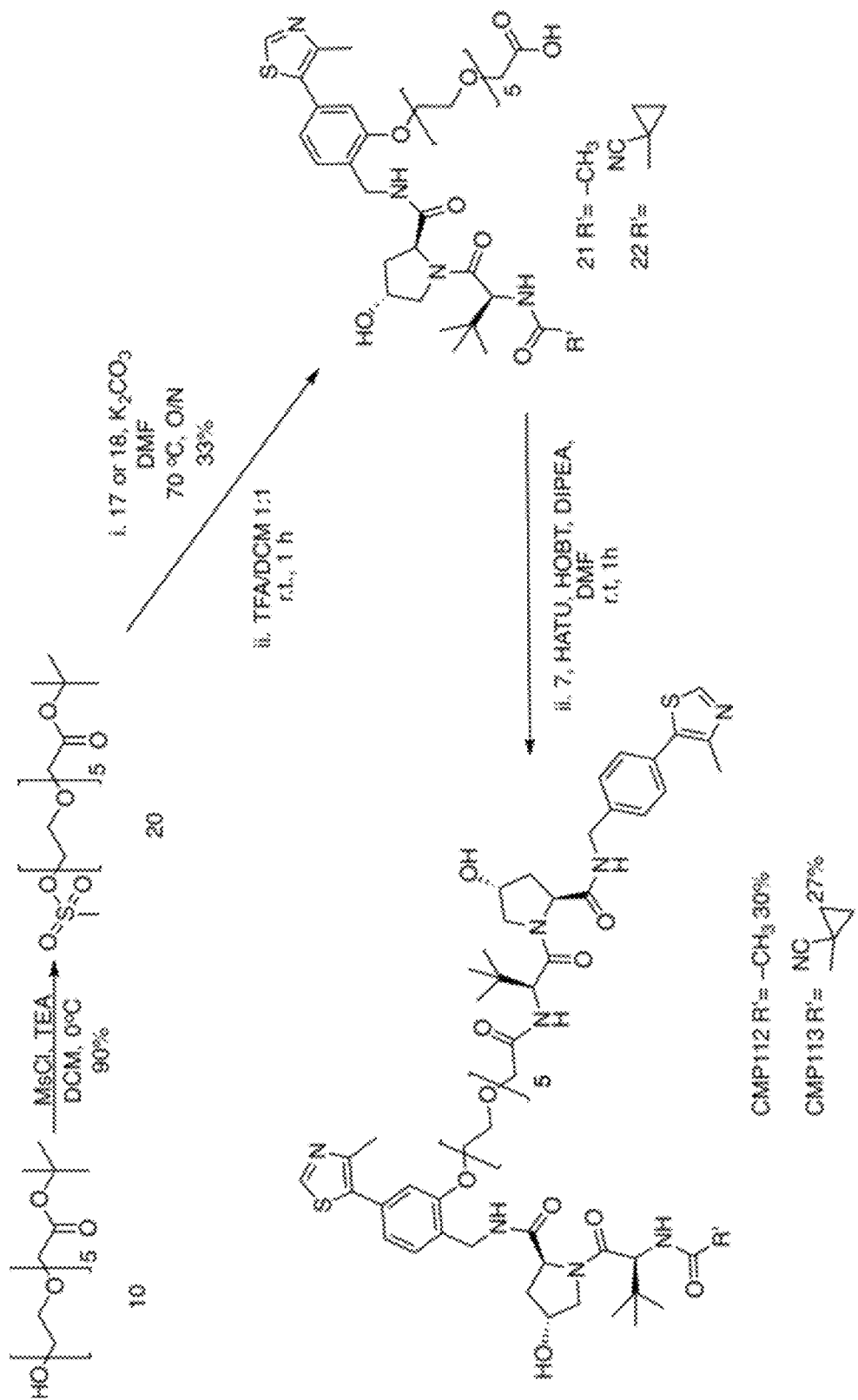
FIG. 7: Synthesis of asymmetric Homo-PROTACs CMP112 and CMP113.

For the synthesis of asymmetric Homo-PROTACs, PEG 10 was converted in to the mesylated derivative 20 and reacted with 17 or 18 to obtain 21 and 22, respectively in good yield (FIG. 7). Final compounds CMP112 and CMP113 were obtained in good yield upon deprotection of the tert-butyl group and amide coupling with compound 7 (FIG. 7).

Biological Evaluation.

We next tested all our Homo-PROTACs in HeLa cells, and monitored protein levels by Western blots after 10 h of compound treatment at 1 µM concentration (FIG. 8a). We observed striking effectiveness of CM09, CM10 and CM11 in inducing VHL depletion in cells (FIG. 8a), and a remarkably selective degradation for the band corresponding to the long isoform of VHL, preferentially over the short isoform. The VHL gene includes three exons and it encodes two major isoforms of VHL: a 213 amino-acid long, 30 kDa form (pVHL30) and a 160 amino-acid long, 19 kDa form (pVHL19). pVHL19 lacks a 53 amino-acid long amino-terminal domain or N-terminal tail (pVHL-N), which is instead present in pVHL30. Although both isoforms are expressed in human cells, pVHL19 is the more prominent form in human tissues.[56] The most active compounds are symmetrically linked from the terminal LHS acetyl group of VH032. Linkage at different positions proved ineffective, suggesting a critical role played by the linking pattern on the VHL ligands. Control compounds CMP98 and CMP99 were unable to induce degradation of VHL (FIG. 8a), demonstrating that Homo-PROTAC activity is dependent on productive bivalent recruitment of VHL by the trans epimer. The length of the linker also seemed to affect cellular potency. Indeed, a decrease in effectiveness was observed at shorter linker lengths, with CM10 and CM11 being the most active compounds achieving total knockdown of pVHL30, followed by CM09 depleting 82% of the target protein. Interestingly, some degradation of the short iso-form pVHL19 was also observed, albeit low (around 10% depletion). Levels of Cullin2, the central subunit of the CRL2-VHL complex,[57] were also reduced upon treatment with CM10 and CM11 by up to 22% (FIG. 8a).

Figure 8:
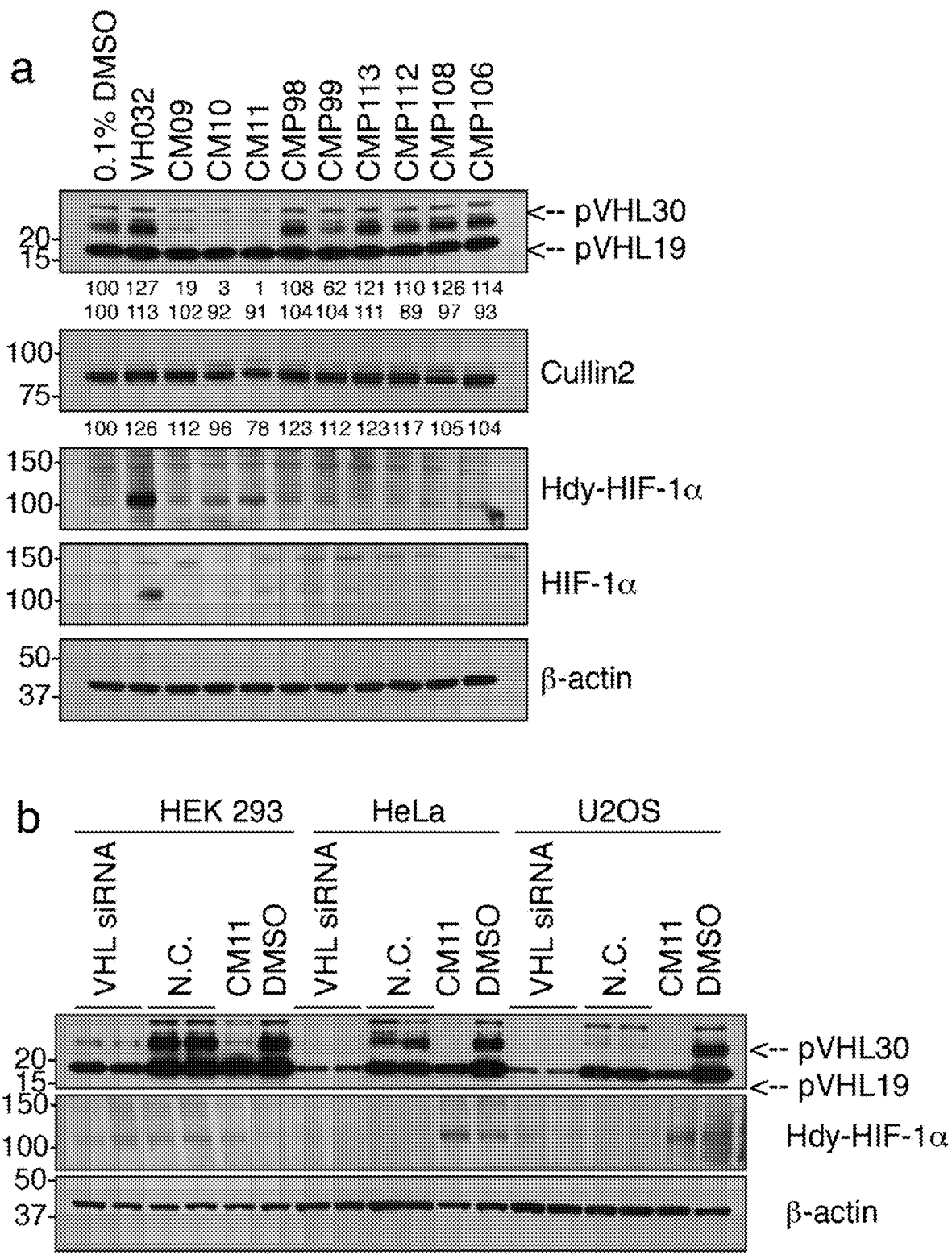
FIG. 8: Biological evaluation of HOMO-PROTACs. (a) HeLa cells were treated with 0.1% DMSO, VH032 (150 µM) and 1 µM of the indicated compounds for 10 h. Abundance of individual proteins was analyzed by Western blotting using corresponding specific antibodies accordingly after SDS-PAGE. (b) Different cells lines were treated with si-RNA targeting VHL proteins or negative control si-RNA (for 48 h), as well as with CM11 (1 µM) or 0.1% v/v DMSO for 10 h.

Treatments with CM10 and CM11 also showed detectable albeit low increase in protein levels of the hydroxylated form of HIF-1α (Hdy-HIF-1α, FIG. 8a). As the parent inhibitor VH032 is completely ineffective at the same concentration of 1 µM (see ref. 3 and vide infra, FIG. 8), this effect cannot be due to VHL inhibition and is therefore thought to be the result of compound-induced protein degradation. Levels of HIF-1α were, however, significantly lower than observed with the parent inhibitors VH032 when used at concentrations>100 µM (FIG. 8a, see also ref.[3]). VHL knockdown by siRNA experiments in three different cell lines was consistent with CM11-induced knockdown, and also insufficient to induce significant HIF stabilization (FIG. 8b). The siRNA result also confirmed that the bands observed to decrease in intensity with compound treatment indeed correspond to VHL.

Figure 14:
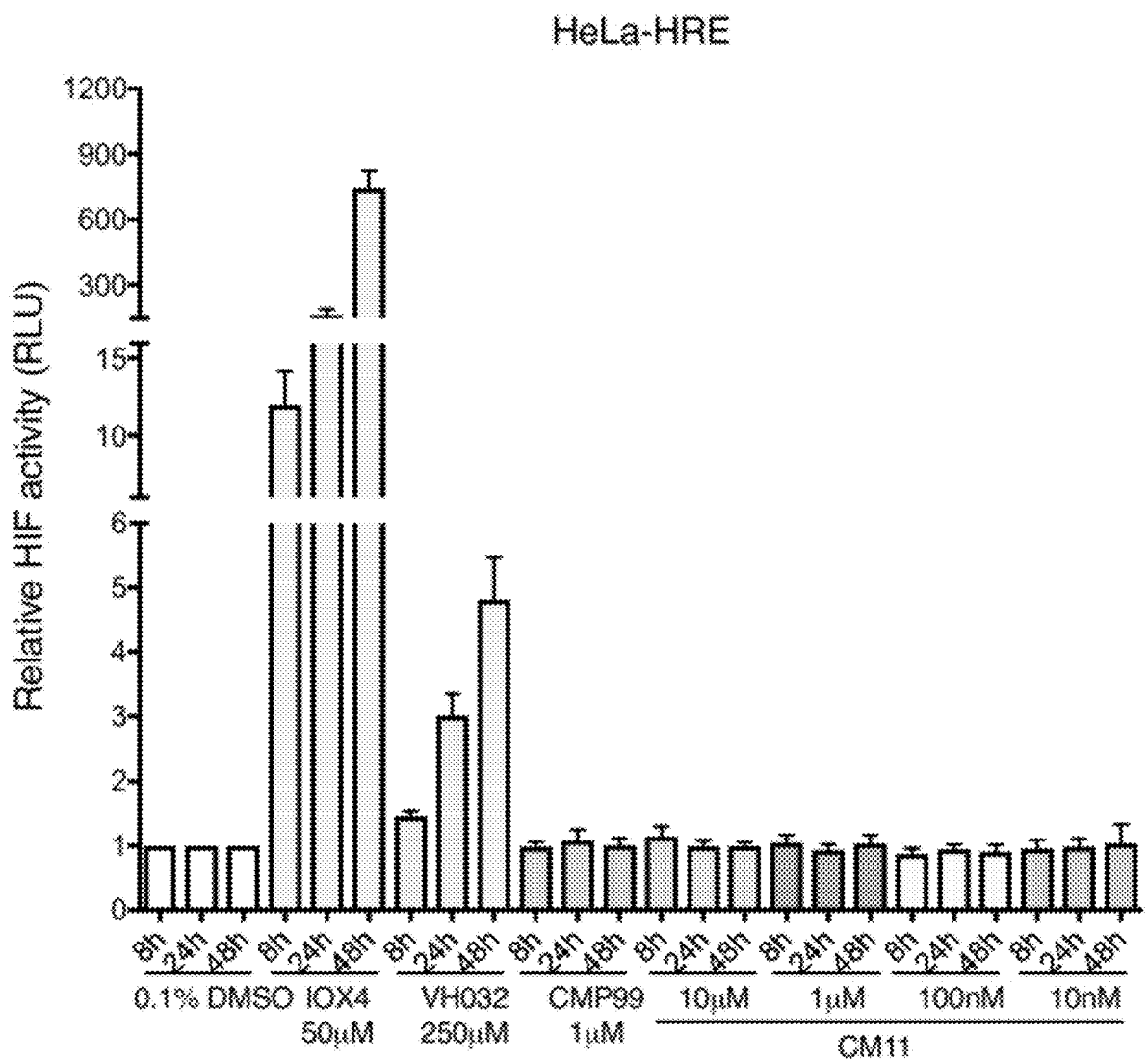
FIG. 14: HeLa or U2OS cells stably expressing HRE-luciferase reporter plasmid were treated with the indicated compounds at the indicated concentrations for the indicated time.
Figure 14:
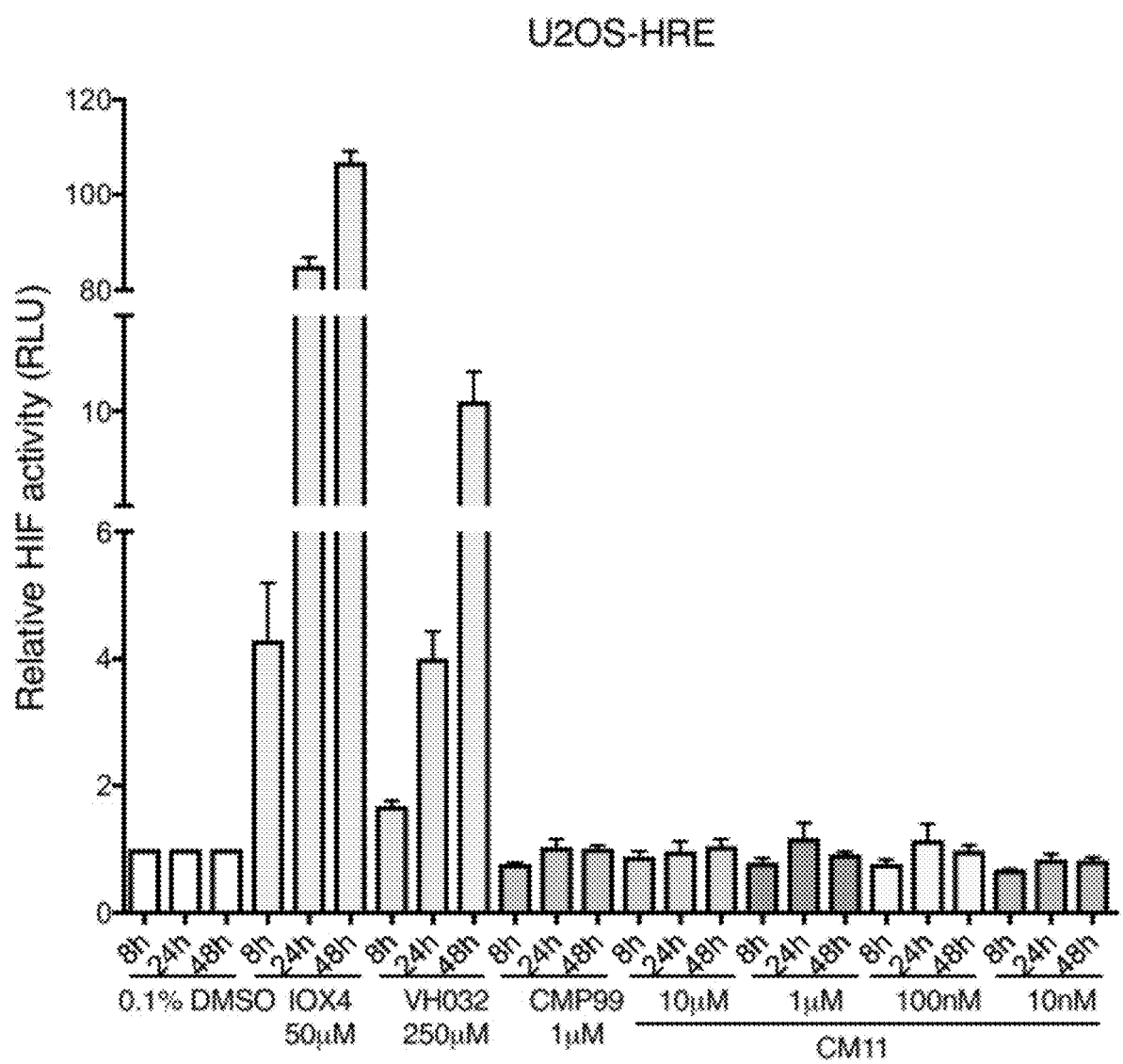
Figure 15:
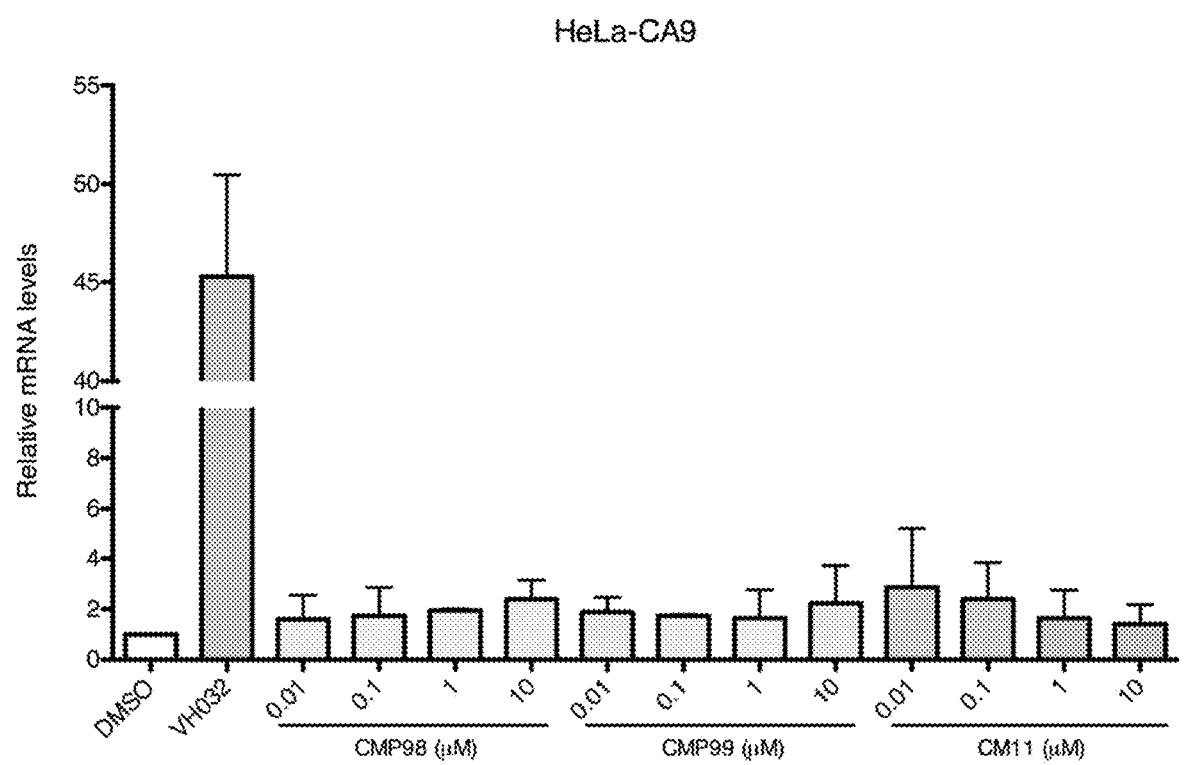
FIG. 15: Dose-response curve of CA9 mRNA expression in HeLa (16 h)

To assess whether selective pVHL19 knockdown by Homo-PROTACs could induce HIF transcriptional activity, we first used a luciferase reporter assay.[37] Hypoxia response element (HRE)-luciferase reporter HeLa-HRE and U2OS-HRE cells were treated with different concentrations of CM11 and at different times, and no increase in HIF-dependent luciferase activity was detected relative to DMSO control treatment (FIG. 14). These results were confirmed in a qRT-PCR assay, where no upregulation of mRNA levels of the known HIF-target genes CA9 was detected (FIG. 15). Together the data suggests that the un-degraded pVHL19 is sufficient to efficiently maintain low levels of HIF-1α, and that complete knockdown of all VHL isoforms is required to achieve effective HIF stabilization in cells, as observed in vhl[−/−] cells such as VHL-deficient renal carcinoma cells.

We next turned our attention to further characterizing the mode of action of the protein degradation induced by the active Homo-PROTACs CM09-11. To interrogate their relative cellular potency, dose-dependent treatments were performed at two different time points, 4 and 24 h prior to harvesting. All compounds confirmed preferential degradation of pVHL30 in a concentration-dependent manner, relative to the corresponding DMSO control (see FIG. 9 for CM11, and FIG. 16 for CM09 and CM10).

Figure 9:
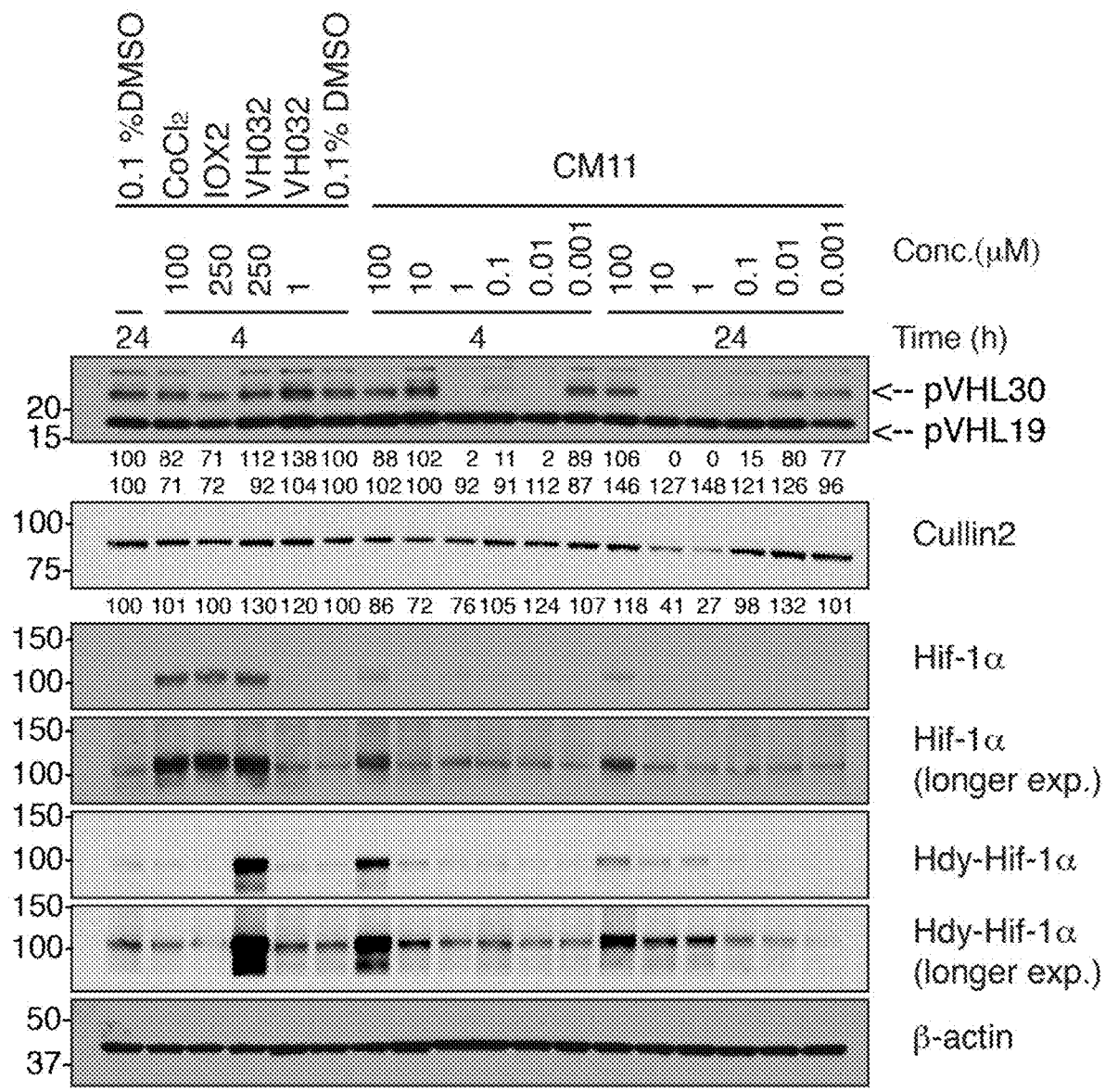
FIG. 9: HeLa cells were treated with increasing concentration of HOMO-PROTAC CM11 for 4 h or 24 h.
Figure 17:
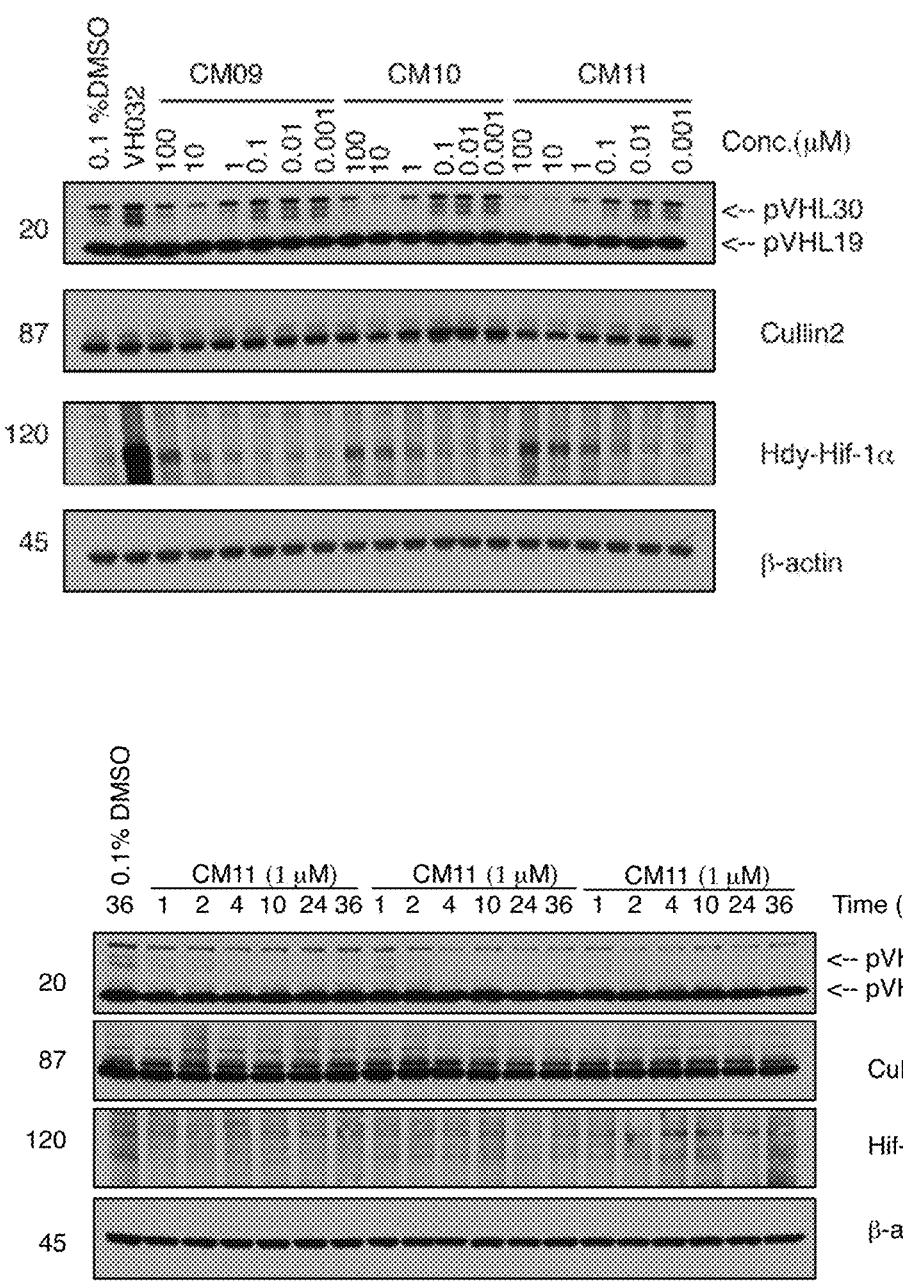
FIG. 17: Concentration dependency experiment in U2OS (10 h treatment)(left) and Time course experiments of lysate from U2OS (right).

CM11 proved the most potent Homo-PROTAC, inducing complete depletion of pVHL30 after 4 h already at 10 nM ($DC_{99}$=10 nM, FIG. 9). Selective pVHL30 knockdown was retained after 24 h, with half-degrading concentration ($DC_{50}$) between 10 and 100 nM. The effective degrading concentrations of CM11 are >3 orders of magnitude lower than the inhibitory concentrations of the constitutive ligand VH032 alone, which is only active in cells at ~100 µM, underscoring the profound difference in cellular efficacy between the two mode of actions. Cellular levels of Cullin2 decreased by up to 73% upon treatment with CM11 (FIG. 9). contrast, both CM10 and CM11 retained their efficacy even at these longer time points (FIG. 17).

TABLE 1

Summary of thermodynamic binding parameters of Homo-PROTACs and comparison with VHL inhibitor VH032 (from 19) measured by ITC, against both short and long VHL isoforms.

| Protein | Compound | n | Kd (nM) | α | ΔG (kcal/mol) | ΔH (kcal/mol) | −TΔS (kcal/mol) |
|---|---|---|---|---|---|---|---|
| pVHL19 | VH032 (ref.[2]) | 1.030 ± 0.001 | 188 ± 6 | — | −9.17 ± 0.02 | −5.53 ± 0.01 | −3.65 ± 0.02 |
|  | CM11 | 0.6 ± 0.01 | 11 ± 2 | 18 | −10.9 ± 0.1 | −12.3 ± 0.7 | 1.4 ± 0.8 |
|  | CMP99 | 0.964 ± 0.005 | 146 ± 2 | — | −9.33 ± 0.06 | −6.23 ± 0.05 | −3.1 ± 0.7 |
|  | CM09 | 0.98 ± 0.09 | 41 ± 15 | 4 | −10.3 ± 0.2 | −6.9 ± 0.3 | −3.5 ± 0.5 |
|  | CM10 | 0.73 ± 0.01 | 32 ± 5 | 6 | −10.2 ± 0.1 | −9.4 ± 0.1 | −0.8 ± 0.2 |
|  | CMP106 | 0.535 ± 0.004 | 111 ± 8 | 1.7 | −9.5 | −12.6 ± 0.1 | 3.1 |
|  | CMP112 | 0.498 ± 0.006 | 235 ± 22 | 0.8 | −9.1 | −14.8 ± 0.2 | 5.8 |
|  | CMP113 | 0.934 ± 0.005 | 117 ± 25 | 1.7 | −9.5 | −6.4 ± 0.2 | −3.1 |
| pVHL30 | CM11 | 0.866 ± 0.003 | 25 ± 3 | 4 | −10.4 ± 0.1 | −11.3 ± 0.1 | −0.9 ± 0.1 |
|  | CMP99 | 1.050 ± 0.004 | 106 ± 10 | — | −9.51 ± 0.05 | −5.19 ± 0.03 | −4.3 ± 0.1 |

Figure 16:
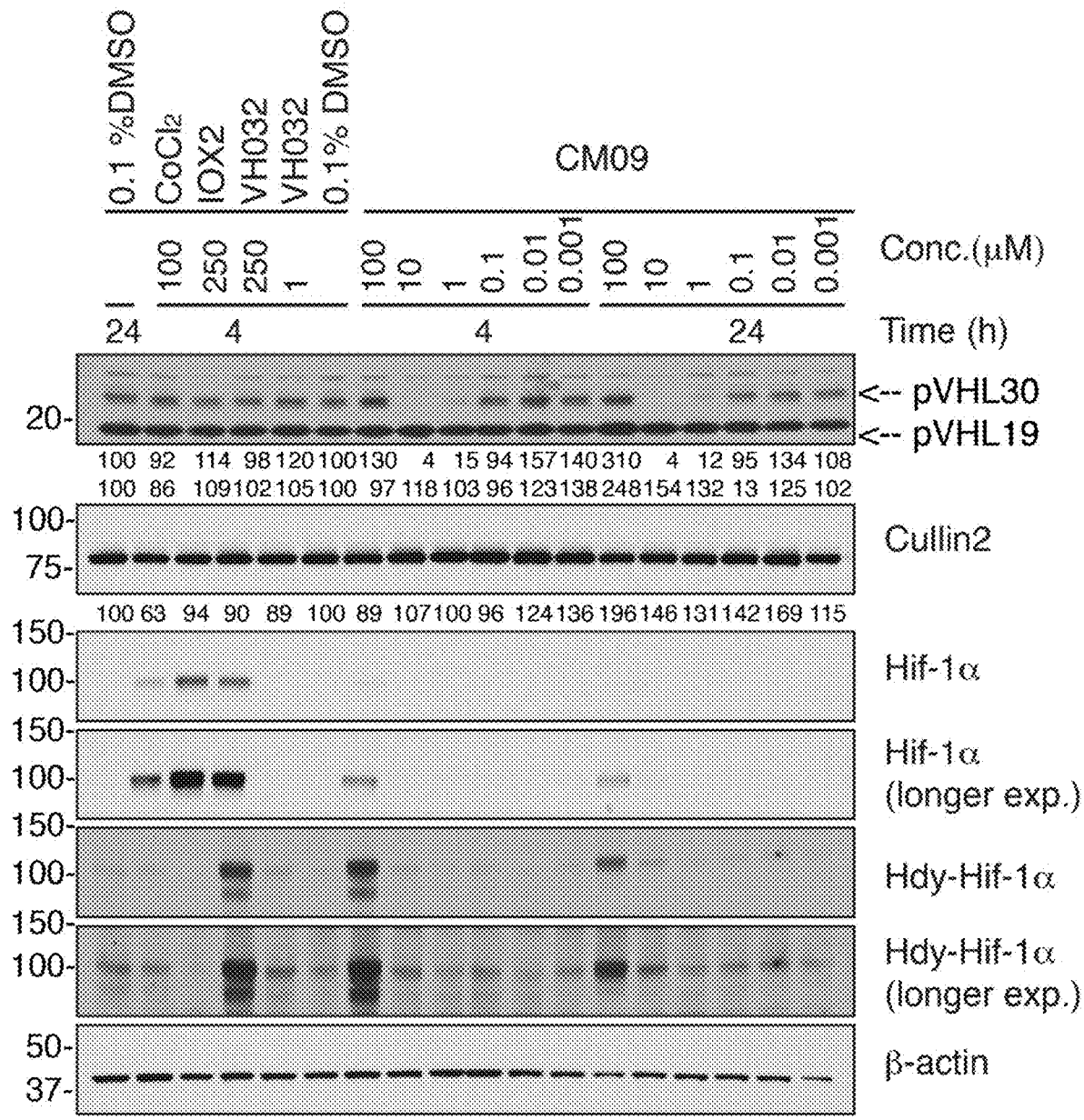
FIG. 16: Hela cells were treated with increasing concentration of indicated compound for 4 h or 24 h.
Figure 16:
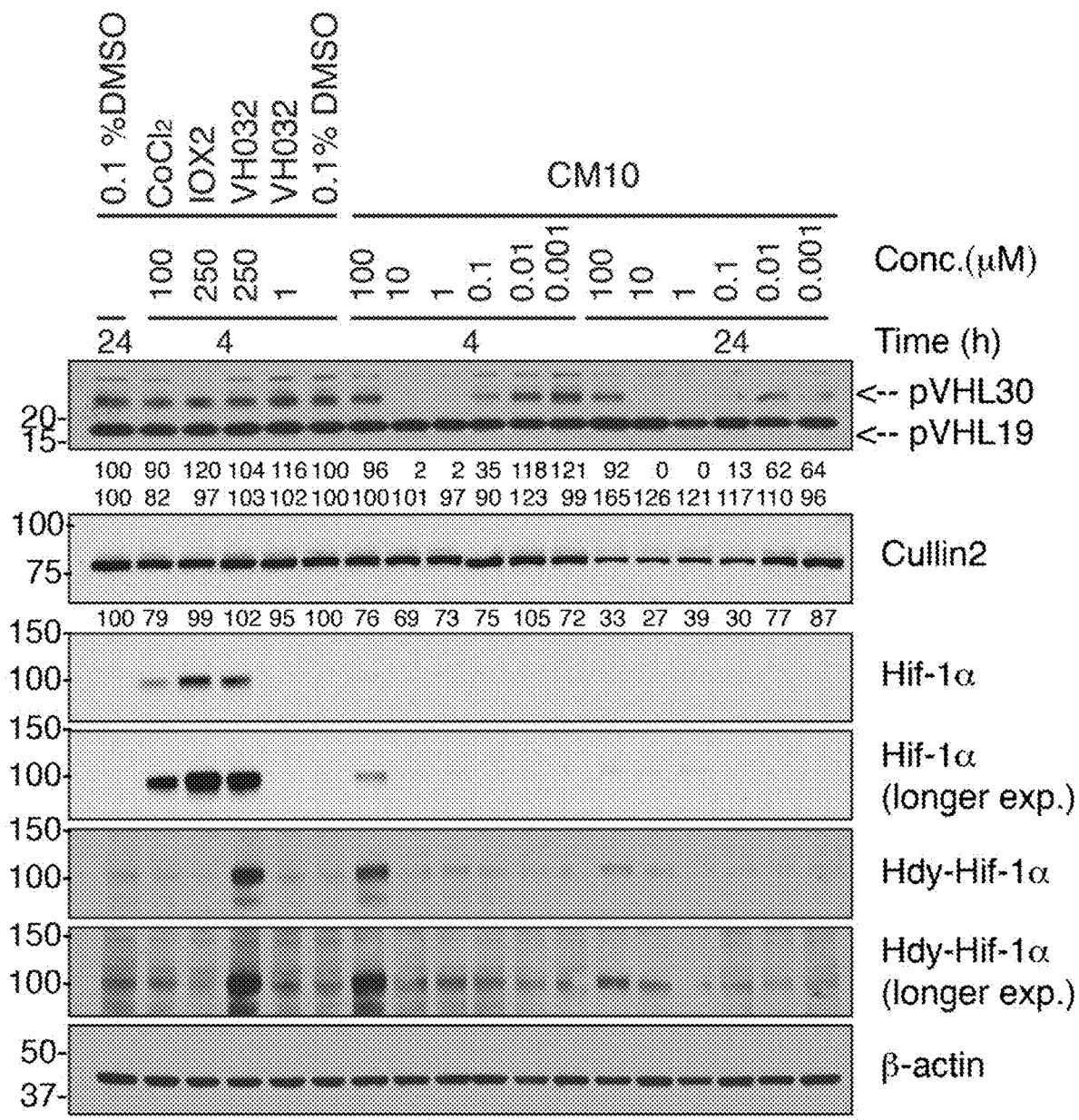

As previously observed, selective pVHL30 knockdown by Homo-PROTACs resulted in only minor increase in levels of HIF-1α, relative to hypoxia-inducing controls $CoCl_2$, PHD inhibitor IOX2, and VH032 (FIG. 9). However, when tested at high micromolar concentrations, Homo-PROTACs acted preferentially as VHL inhibitors over VHL degraders, consistent with the so-called "hook-effect" whereby formation of binary 1:1 complexes competes with and eventually supersedes the formation of the productive catalytic 2:1 complex.[59] Stabilization of Hdy-HIF-1α upon treatment with all three compounds at 100 μM was indeed comparable with the effect obtained with VH032 alone (FIG. 9 for CM11, and FIG. 16 for CM09 and CM10). To confirm the cellular activities of Homo-PROTACs in a different cell line, a similar experiment was performed treating U2OS cells for 10 h with CM09, CM10 and CM11 using the same range of concentrations (1 nM-100 μM). A consistent profile of cellular activity was observed, confirming that the effects observed are independent from cell type (FIG. 17).

Figure 10:
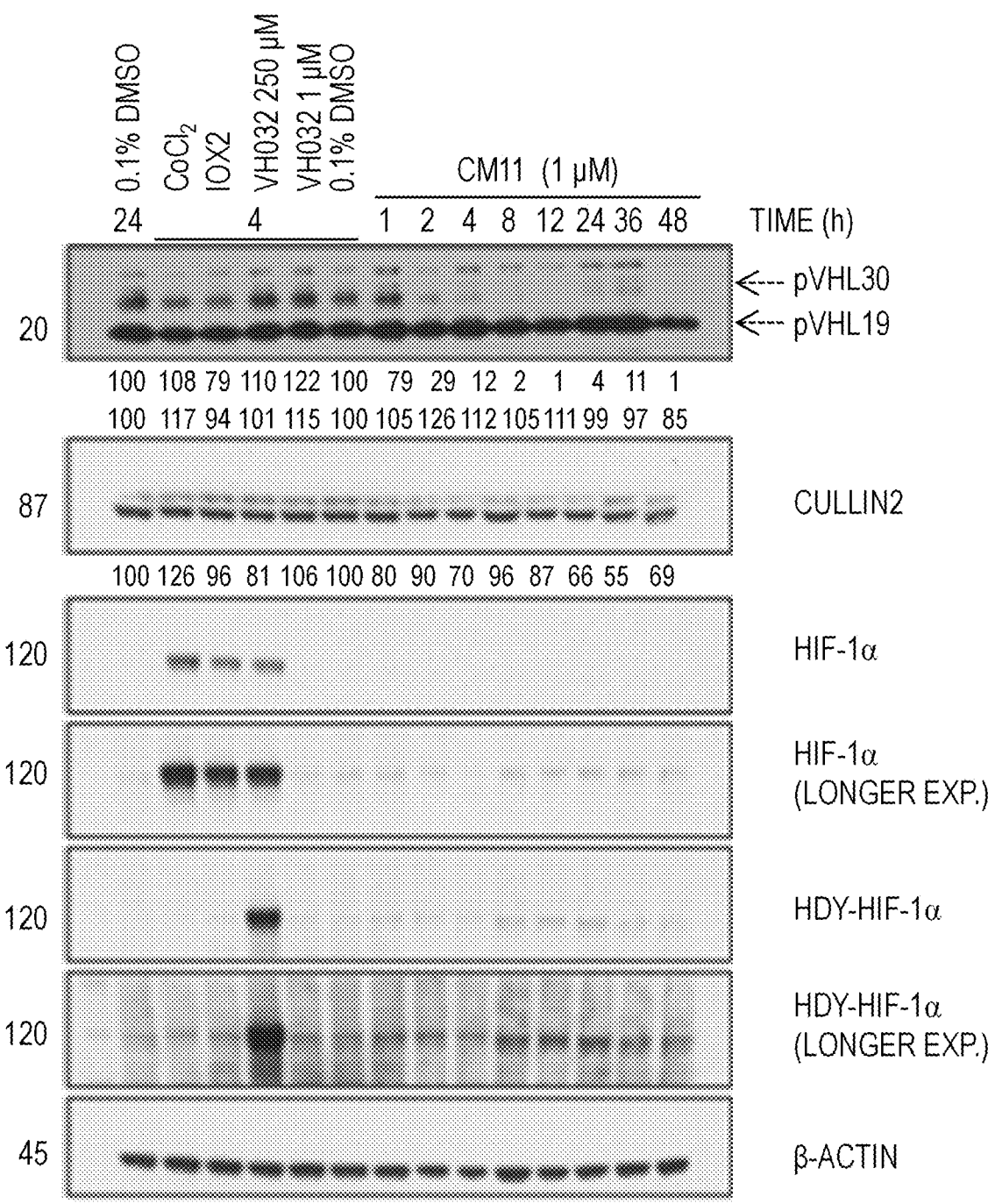
FIG. 10: Time-course immunoblots of lysates from HeLa cells subjected to 0.1% DMSO, CoCl2 (100 mM), IOX2 (150 mM), VH032 (250 mM or 1 mM) or 1 mM of CM11.
Figure 11:
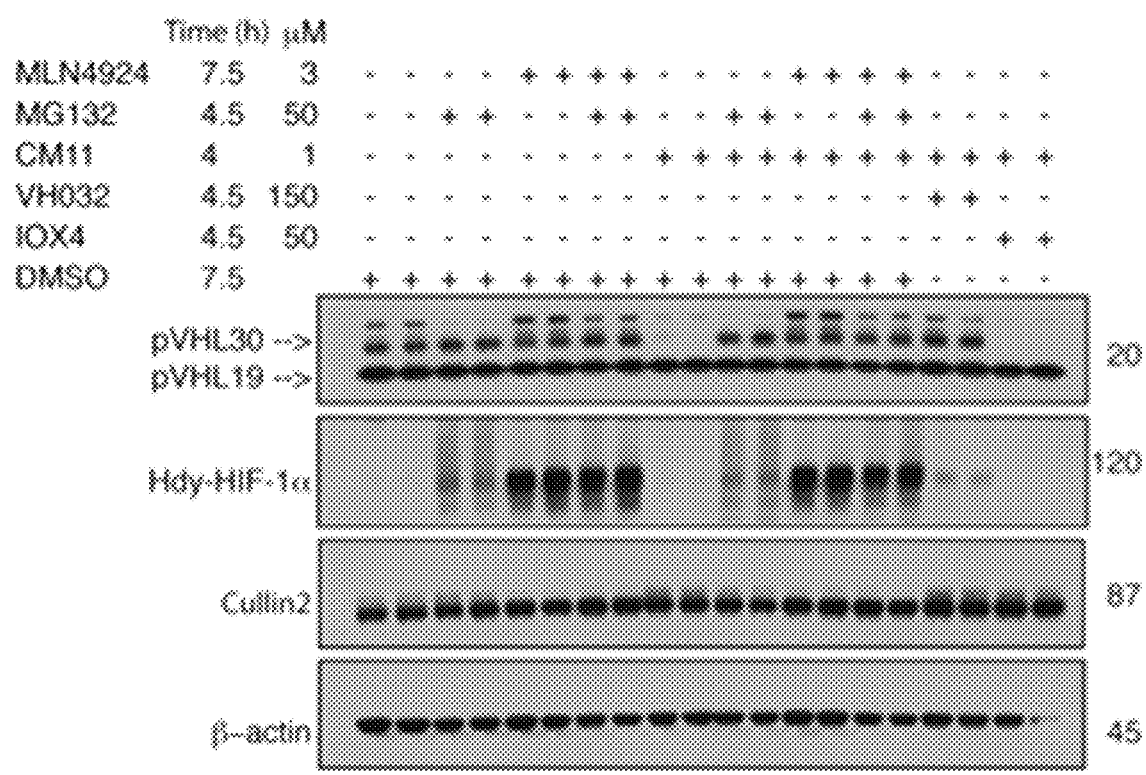
FIG. 11. Compound activity is CRL2VHL and proteasome dependent. HeLa cells treated with CM11 in the absence or presence of proteasome inhibitor MG132, MLN4924, VHL inhibitor VH032 or PHD2 inhibitor IOX4.
Figure 18:
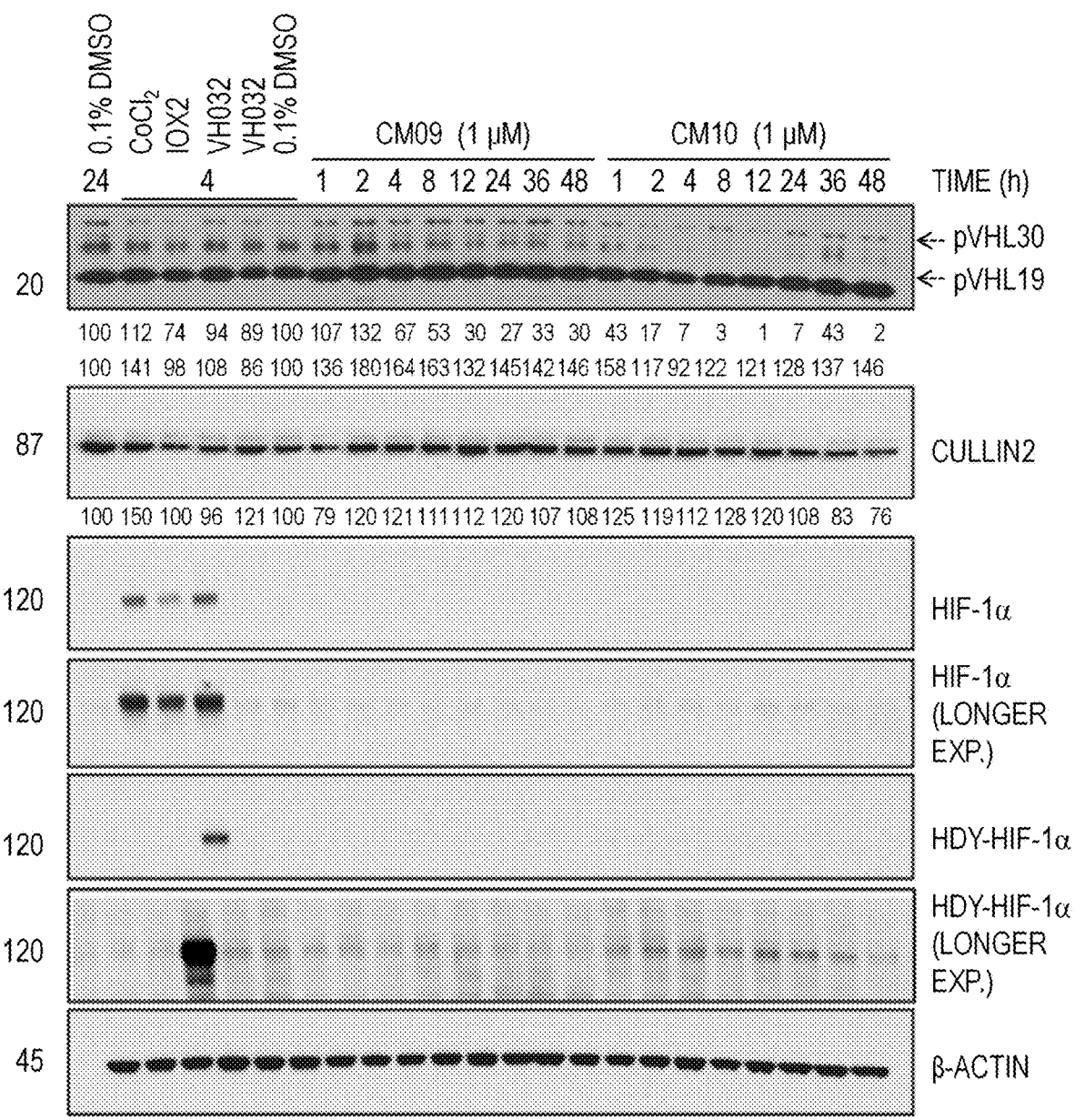
FIG. 18: Time-course immunoblots of lysates from HeLa cells subjected to 0.1% DMSO, CoCl2 (100 µM), IOX2 (150 µM), VH032 (250 µM or 1 µM) or 1 µM of indicated compounds.

We next interrogated the time-dependent activity of Homo-PROTACs. Progressive removal of VHL protein overtime was observed, confirming selective depletion of pVHL30 over the short isoform (FIG. 10 for CM11 and FIG. 18 for CM09 and CM10). In particular, CM11 was confirmed to be the most effective compound, decreasing pVHL30 level by more than 70% already after 2 h of treatment, and essentially to completion after 8 h. The depletion effect was retained up to 12 h; however, interestingly, pVHL30 levels up to 11% were detected after 24-36 h treatment, to then decrease again after 48 h. Incomplete degradation of pVHL was observed upon treatment with CM09, even in the longer time points (FIG. 18). As before, minor stabilization of Hdy-HIF-1α over time was observed for all three compounds, most pronouncedly up-on treatment with CM11. The results obtained treating U2OS cells were consistent with what observed in the previous experiment. However, in this cell line all the three compounds were able to induce complete degradation of pVHL30 over time (FIG. 17). We hypothesize that this could be due to the lower expression level of VHL in U2OS, leading to faster cellular depletion compared to cell lines where VHL level is higher. CM09 and CM10 achieved complete degradation of the target protein after 2 h of treatment. CM11 confirmed to be the most potent compound also in this cell line, achieving complete degradation of pVHL30 already after 1 h. Interestingly CM09 lost its cellular efficacy after 36 h. In To gain mechanistic insights in the cellular activity of Homo-PROTACs, the dependency on CRL2-VHL and proteasome activities was examined. The reliance of the Homo-PROTAC-induced protein degradation on CRL2-VHL was assessed by inhibiting neddylation of Cullin2 using the NAE1 inhibitor MLN4924, which blocks the activity of CRLs, including CRL2-VHL. Proteasome-dependency was interrogated by treating cells with the proteasome inhibitor MG132. To limit the known cytotoxicity of MLN4924 and MG132, HeLa cells were pre-treated with MLN4924 for 3 h followed by MG132 for 30 min before adding CM11 to the media, and cells were incubated for further 4 h before harvesting. Single treatments with DMSO, MLN4924, MG132 and CM11 and combinations thereof were performed to disentangle the individual and combined effects of compound treatments. Degradation of pVHL30 induced by CM11 was completely abrogated when cells were pre-treated with MG132, establishing the expected proteasome-dependence of the chemical intervention (FIG. 11). CM11-induced degradation was also prevented by pre-treatment with MLN4924, confirming the dependency on the activity of CRL2VHL (FIG. 11). The same effect was observed when cells where co-treated with MLN4924 and MG132 prior to CM11 (FIG. 11). Immunoblots of Cullin2 levels confirmed the effective blockade of Cul2 neddylation by MLN4924 (FIG. 11). To assess if CM11 de-grading activity was dependent on VHL binding, a competition experiment was performed using the VHL inhibitor VH032.20 HeLa cells were pre-treated with VH032 at 150 μM for 30 min before adding CM11 into the media. The plates were incubated for further 4 h before harvesting. As expected, VH032 blocked pVHL degradation (FIG. 11) consistent with the hypothesis that VHL induces degradation of itself. In contrast, pre-treatment with IOX4, a PHD2 inhibitor, did not impact the cellular activity of CM11 (FIG. 11).

Biophysical Evaluation

Figure 12:
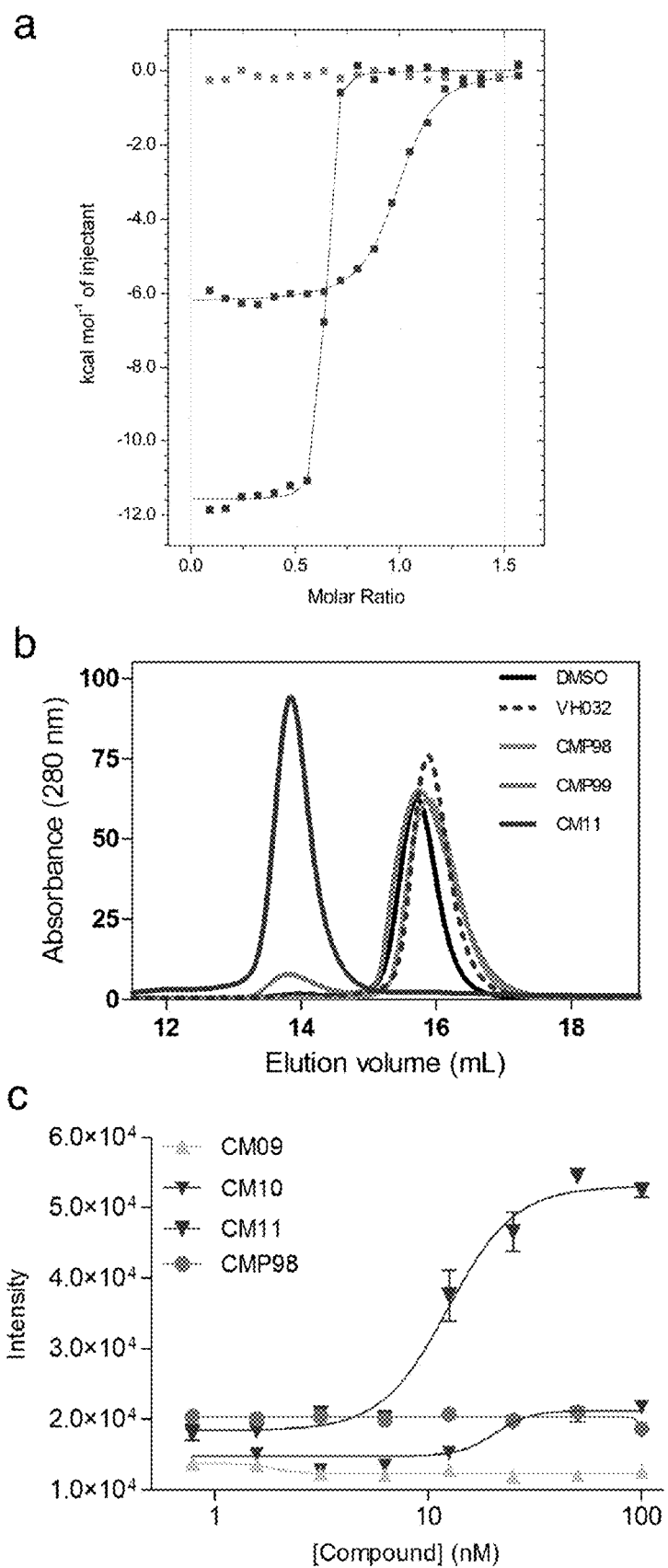
FIG. 12. Biophysical studies of Homo-PROTACs binding to VHL. (a) Superposition of the integrated ITC heat curves of CM11 CMP99 or CMP98 titrations against VCB. (b) SEC assay of complex formation after incubation of CM11, CMP98, CMP99, VH032 or DMSO with VCB. (c) AlphaLISA: intensity values titrating CM09, CM10, CM11 and CMP98 against VCB. Each point is mean (±SEM) intensity of four technical replicates.
Figure 19:
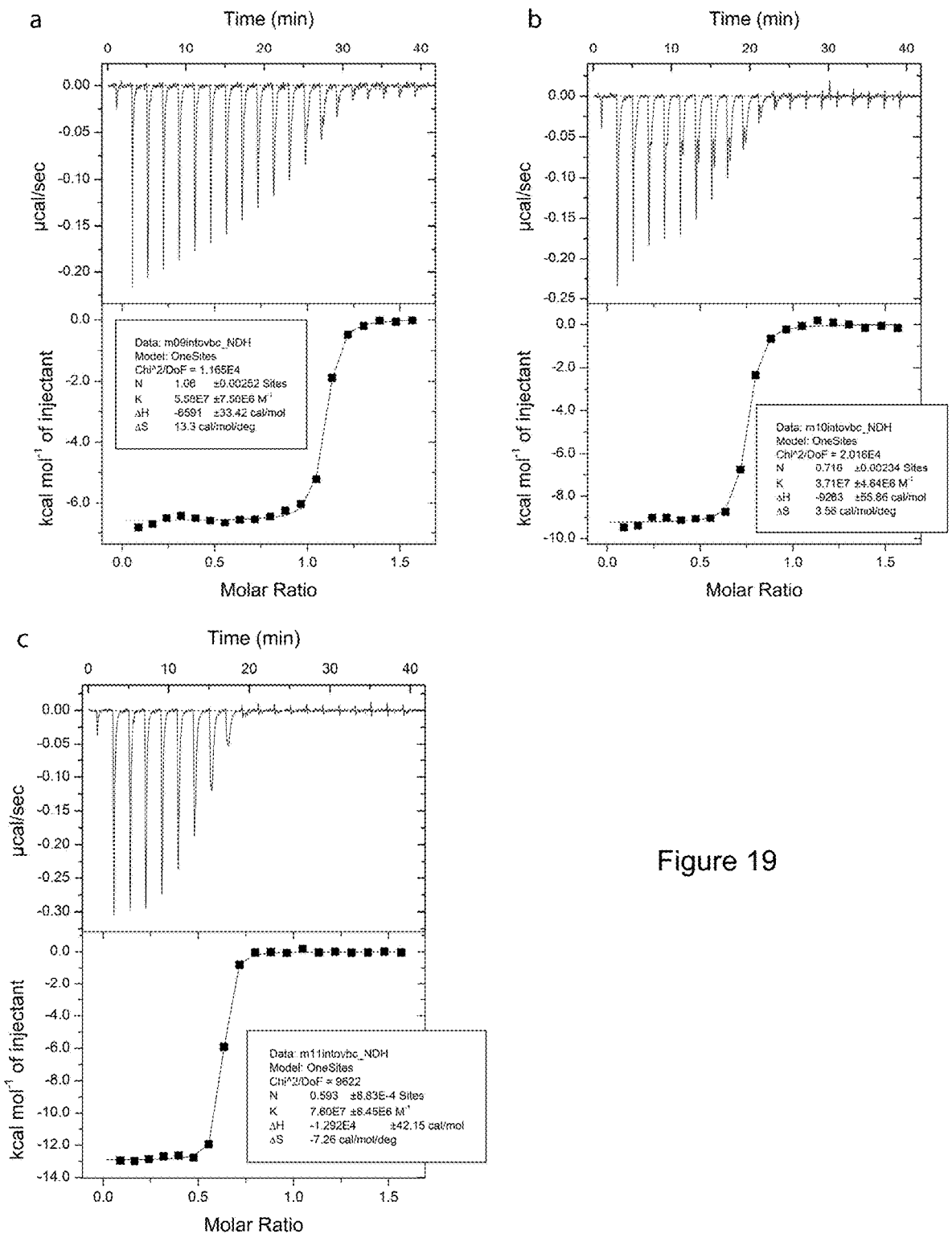
FIG. 19: Integrated ITC heat curves of CM09 (a), CM10 (b), and CM11 (c) against VCB.
Figure 20:
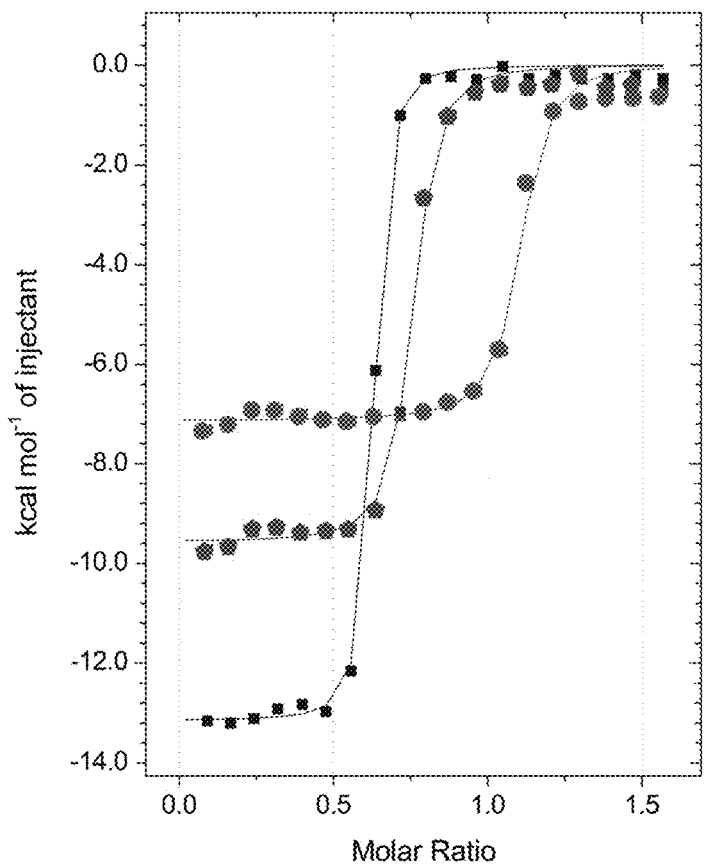
FIG. 20: Superposition of the integrated ITC heat curves of CM11, CM09, or CM10 titrations against VCB.

Key to the catalytic mode of action of PROTACs is the formation of a ternary complex.[13,15] In the case of our Homo-PROTAC compounds, VHL acts as both the E3 ligase and the substrate. Therefore, we next sought to monitor and biophysically characterize the ternary complex VHL:Homo-PROTAC:VHL that is thought to underlie cellular activity. To assess the formation of this ternary complex species in solution, isothermal titration calorimetry (ITC), size exclusion chromatography (SEC) and AlphaLISA proximity assays were performed (FIG. 12). In ITC titration of CM11 against the VCB complex (VHL with Elongin B and Elongin C) the stoichiometry of binding (n value) was found to be 0.6, instead of 1 with VH032 (FIG. 12a, Table 1). This result is consistent with CM11 binding to VHL in a 1:2 molar ratio, in contrast to VH032 that binds to VHL in a 1:1 ratio.[19] Notably, the $K_d$ value measured for CM11 was 11 nM (Table 1). Closer examination of the titration curve revealed that only one point features during the inflection of the curve. Indeed, because the protein concentration used in the experiment was 20 μM, the c value (defined as $[P]_{tot}/K_d$) calculated for this experiment is 2500, which is well above the upper limit of c (around 500-1000) that is a prerequisite for precise measurement of binding affinity. Consequently, this analysis suggests that we may be underestimating the binding affinity of CM11, i.e. we can conclude that $K_d$ is ≤118 nM. This corresponds to an avidity (also known as cooperativity α) of >18-fold when compared to VH032. Such large avidity of homobivalent molecules has been observed previously with other systems, for example the BET inhibitor MT1. The binding interaction between CM11 and VHL was driven by a large apparent binding enthalpy ($\Delta H=-12.3$ kcal mol$^{-1}$), whereas the entropic term was slightly unfavourable ($-T\Delta S=1.4$ kcal mol$^{-1}$). This observation underlines how the thermodynamic signature of CM11 is also very different when compared with that of VH032, in which case the binding ΔH was around half that observed with CM11, and both the enthalpic and entropic term contributed favourably to the ΔG of binding (Table 1). By contrast, the thermodynamic values obtained for CMP99 binding were entirely consistent with the ones of VH032 (Table 1). Specifically, CMP99 bound to VHL in a 1:1 ratio, as expected due to the presence of the cis-Hyp in one of the two moieties, and it exhibited comparable ΔH and $K_d$ values to VH032. As expected, binding was not detected with CMP98, the inactive cis-cis epimer. Superposition of integrated heat curves of CM11, CMP98 and CMP99 is shown in FIG. 12b and visually highlights the different behaviours of the three compounds. CM10 showed similar thermodynamic binding parameters relative to CM11, with n value equal to 0.7 and a low Kd of 32 nM. A stoichiometry close to 1 was instead found for CM09, suggesting that at the end of the titration this system was primarily populated by 1:1 complexes (FIGS. 19 and 20), consistent with its lower avidity (Table 1). ITC experiments were also conducted with compounds CMP106, CMP108, CMP112 and CMP113, and the results are discussed below.

Figure 21:
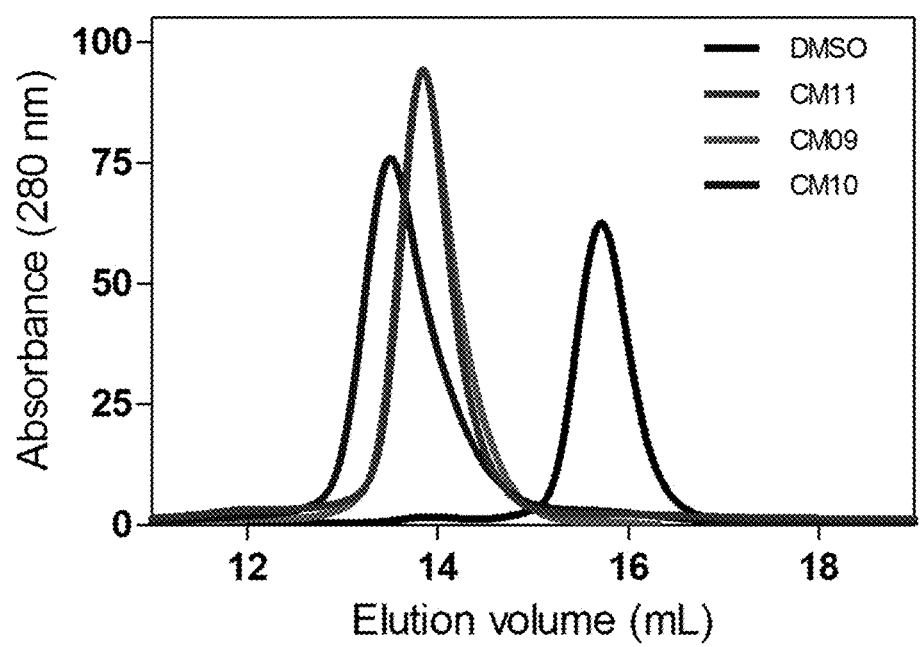
FIG. 21: SEC assay of complex formation after incubation of CM11, CM09, CM10 or DMSO (black) with VCB.
Figure 22:
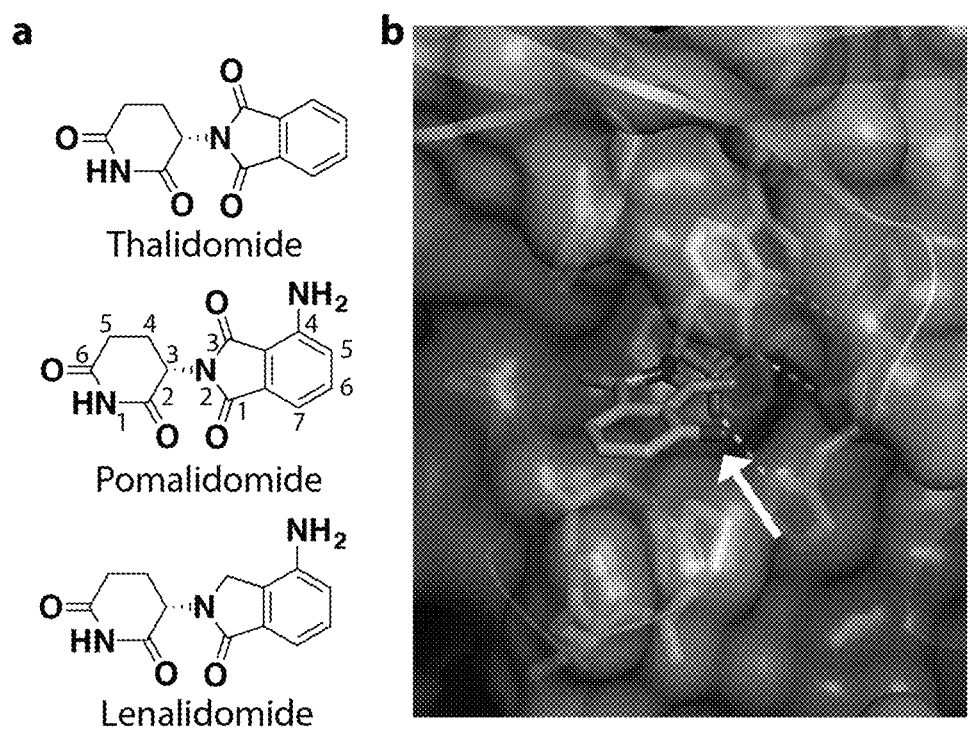
FIG. 22: Immunomodulatory drugs targeting cereblon. (a) Chemical structures. (b) Crystal structure of pomalidomide bound to CRBN (PDB code 4Cl3)[5]

SEC experiments showed that VCB migrates more quickly in the presence of the active compound CM11 (2:1 protein:ligand ratio), relative to the vehicle control (FIG. 12b). The shifted peak eluted at a volume corresponding to a species of ~90 kDa molecular weight, based on a calibration run with globular proteins of known molecular weight (see Methods below), suggesting the peak corresponds to the ternary complex $(VCB)_2$:CM11. In contrast, there is no shift in VCB following incubation with inactive CMP98, CMP99 or ligand VH032. Only in the sample containing CMP99 a small peak eluted at 13.5 ml (FIG. 12b). It is possible that such peak could be due to the formation of a lowly populated ternary complex. It is interesting that Schofield and colleagues observed weak binding of a cis-hydroxyprolyl containing HIF-1α peptide to VHL.[36] This weak binding, potentially enhanced by high avidity in the ternary complex, could be responsible for the small decrease of VHL levels observed during biological tests in cells (FIG. 8a). CM10 and CM09 showed formation of a ternary complex eluting at identical retention volume when compared to CM11 (FIG. 21). No evidence of aggregation was seen with any of the compounds evaluated, as all observed peaks eluted well after the void volume.

Lastly, we employed an AlphaLISA proximity assay to compare ternary complex formation by CM09, CM10 and CM11. The assay showed the highest intensity signal for CM11, whereas negligible levels of complex formation were detected for CM09 and CM10 (FIG. 12c). Since SEC detected ternary species with all three compounds, the minimal intensity detected in the AlphaLISA likely reflects the inability of CM09 and CM10 to yield a significant ternary population at the low concentrations required for the assay. These results indicate that CM11 is the most effective Homo-PROTAC at driving ternary complex formation, consistent with CM11 exhibiting the highest avidity and full 2:1 stoichiometry in ITC. Together, the biophysical data supports CM11 as the most cooperative Homo-PROTAC in vitro, and provide a molecular rationale explaining its potent VHL-degrading activity inside cells.

Discussion

Figure 13:
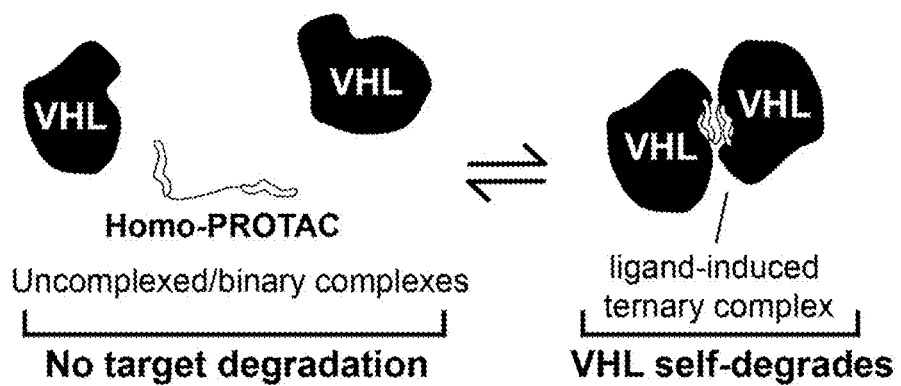
FIG. 13: Proposed model for the mechanism of action of Homo-PROTAC CM11.

In some embodiments, Homo-PROTACs are described, a small-molecule approach to effectively dimerize an E3 ubiquitin ligase to induce its own self-destruction. Using potent ligands for the E3 ligase VHL, a series of symmetric homo-bivalent molecules that induce remarkably rapid, profound and selective degradation of the long isoform of pVHL at nanomolar concentrations were developed. Compound-induced degradation was exquisitely dependent on the linkage pattern on the VHL ligand. The most active Homo-PROTAC, CM11, induces complete depletion of pVHL30 after 4 h already at 10 nM. Potent and selective degradation of pVHL30 was long lasting, with half-degrading concentration ($DC_{50}$) of approximately 100 nM, a remarkable increase in cellular activity of >1000-fold compared to the parent inhibitor VH032. Mechanistically, it has been shown that CM11 activity is strictly dependent on proteasome activity, Cul2 neddylation, and on VHL binding, and specifically on the formation of an avid 2:1 complex with VHL. The data therefore supports a model in which a highly cooperative ternary complex VHL-CM11-VHL functions as the key species responsible for the induced degradation of VHL itself (FIG. 13), which will warrant future structural studies. Interestingly, CM11 also led to a decrease in cellular levels of Cullin2, which we hypothesize to be the result of direct ubiquitination of Cullin2 as part of the $CRL2^{VHL}$ complex. To our knowledge, this is first demonstration that a PROTAC can induce the degradation of a protein forming part of the same complex with the protein targeted directly.

The preferential induced degradation of pVHL30 over the short VHL isoform was unexpected and is an intriguing result of this work. This observation adds to recent evidence from us and others that chemical degraders designed from inhibitors recruiting more than a single protein paralog or isoform can add a layer of target degradation selectivity independently of target engagement.[12,15,18] As the binary engagement of the VHL warhead was found to be similar between the two VHL isoforms (Table 1), the observed selectivity could be due to large differences in cooperativities, which would impact on the relative population of ternary complexes.[15] However, CM11 actually exhibited greater avidity in vitro for the short relative to the long isoform of VHL (Table 1). We therefore view it as unlikely that the remarkable selectivity of VHL degradation is due to large differences in cooperativities of ternary complexes. We also consider unlikely that preferential and more efficient lysine ubiquitination could play a role, because the extra region present in the long isoform (1-53) does not contain a single lysine residue. On the other hand, this region is predicted as intrinsically disordered, and indeed it has been shown that proteins containing disordered N-terminal regions are more prone to proteasomal degradation. It is also known that VHL is resistant to proteasomal degradation when in complex with ElonginB and ElonginC, so the form observed to be preferentially depleted may be free VHL i.e. unbound to Elongins, or other proteasome-sensitive forms. Addressing these questions will be of clear importance for future investigation.

Selective degradation of pVHL30 by CM11 led to minimal stabilization of HIF-a in cells, and as a result did not trigger HIF-dependent activity in cells. This highlights the potential benefit of using CM11 to interrogate the biological function of specific VHL isoforms, without the masking downstream effects of a hypoxic response. Not much is known about the individual roles of VHL isoforms. Studies have highlighted how the 53-residue extra region of pVHL30 is not needed for tumor suppression, and how both isoforms can have HIF-dependent tumor suppressor functions in vivo. Other HIF-independent roles of pVHL have been proposed, including a role for pVHL in collagen assembly. However, the individual roles of the different isoforms in these biological functions remain elusive. Moreover, many HIF-independent roles are thought to be independent upon Hyp recognition, and thus cannot be probed chemically using current Hyp-based VHL inhibitors. Selective and acute knockdown of pVHL30 by CM11 provides therefore a novel chemical tool to address these questions.

In summary, we present CM11, a chemical probe for rapid and selective pVHL30 knockdown. CM11 provides an alternative advantageous chemical tool to conventional knockdown RNAi approaches and gene editing knockout technologies such as CRISPR-Cas9. Relevant information to the use of CM11 will be made available in the newly established "Chemical Probes Portal" (http://www.chemicalprobes.org/).[38] We anticipate CM11 will find wide use amongst chemical and cell biologists alike interested in investigating and dissecting the pleiotropic biological functions of pVHL. More generally, we provide first proof-of-concept that bivalent molecules can be designed to induce an E3 ligase to destroy itself. This strategy could provide a powerful new approach to drugging E3 ligases in ways that may not be possible with inhibitors alone.

Synthesis of PROTACs Recruiting Together CRL4$^{CRBN}$ and CRL2$^{VHL}$.

Figure 23:
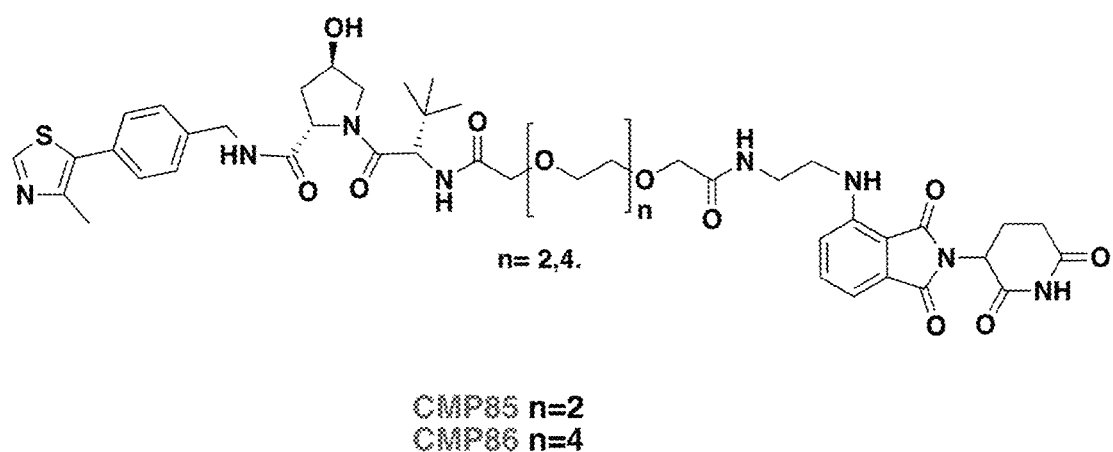
FIG. 23: Structure of Hetero-PROTACs designed to recruit CRL4$^{CRBN}$ at one end and CRL2$^{VHL}$ at the other end.
Figure 24:
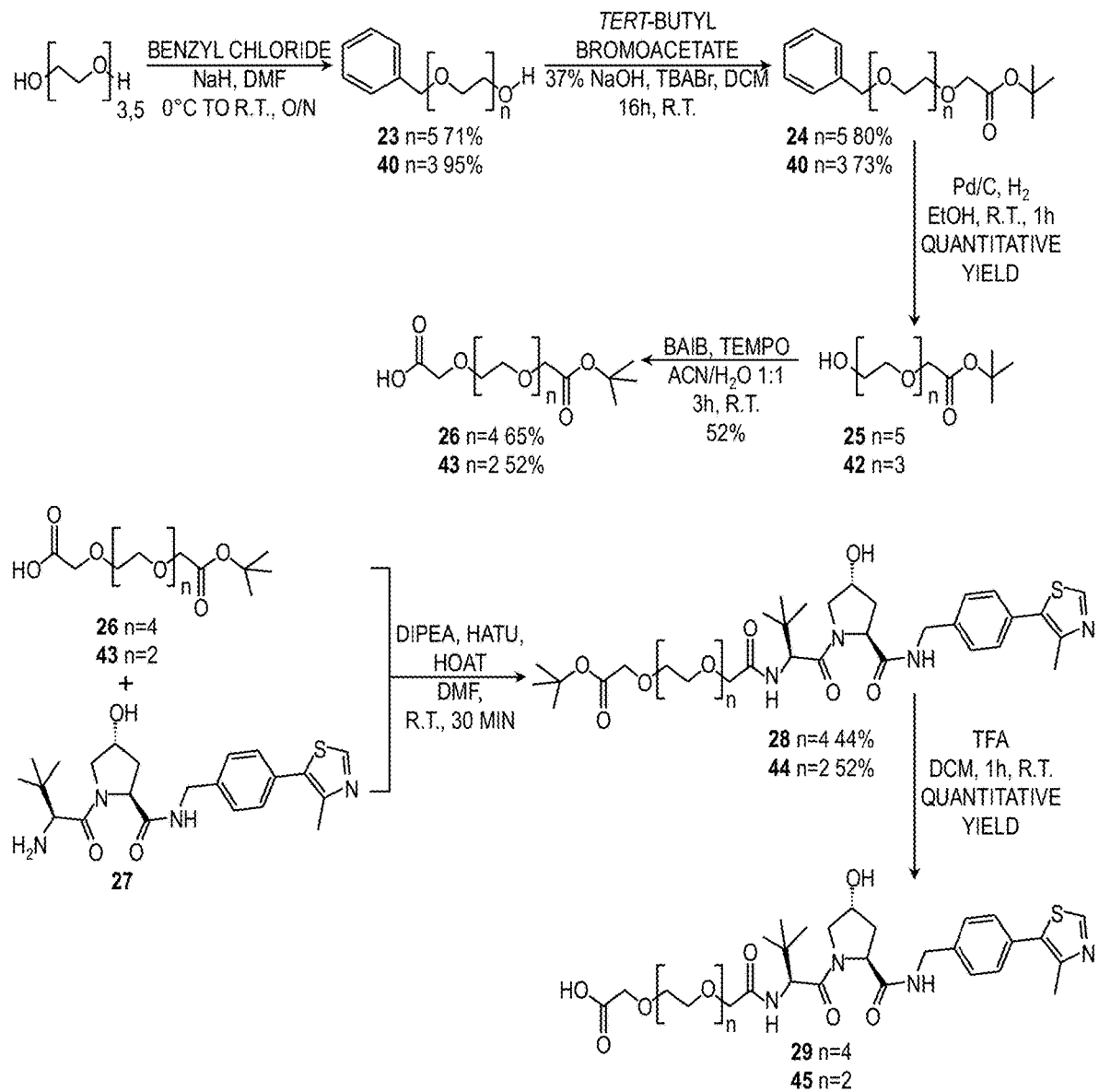
FIG. 24: Synthesis of intermediates 29 and 45.

For the synthesis of compounds CMP85 and CMP86 (structures shown in FIG. 23), the linker 26 and its analogue with two PEG units 43 were synthesized adopting the same route used for 26 (FIG. 24). These linkers were then coupled to compound 27, delivering compounds 28 and 44, respectively. Subsequent deprotection of the tert-butyl group afforded compound 29, with a length of four PEG units, and 45, with two PEG units instead (FIG. 24).

Figure 26:
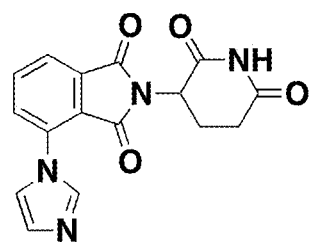
FIG. 26: Side product 53 of cyclization reaction.

Compound 48 (the desired thalidomide derivative, see Figure) was synthesized as previously published by Lu et al.[17] In the first step, 3-fluorophthalic acid was dehydrated with acetic anhydride to obtain compound 46 in good yield. Reaction of compound 46 with L-glutamine and subsequent treatment with HCl 4 M solution led to the formation of compound 47. Cyclization of 47 was performed at reflux in the presence of 1,1'-carbonyldiimidazole (CDI) and DMAP. The recommended time for this step was 5 h. After 2.5 h it was possible to observe the formation of a side product by LC-MS. For this reason, even if the reaction was not completed, the reaction was cooled to r.t. and the resulting solid collected by filtration. During the purification step, performed by column chromatography over silica, compound 48 was isolated in good yield. The side product was isolated as well and analysed by NMR and identified to be compound 53 (FIG. 26). Compound 53 is the product of an aromatic nucleophilic substitution at position 4 of the phthalic anhydride by the nitrogen lone pair of imidazole, which is itself a byproduct of the reaction between 47 and CDI.

Figure 25:
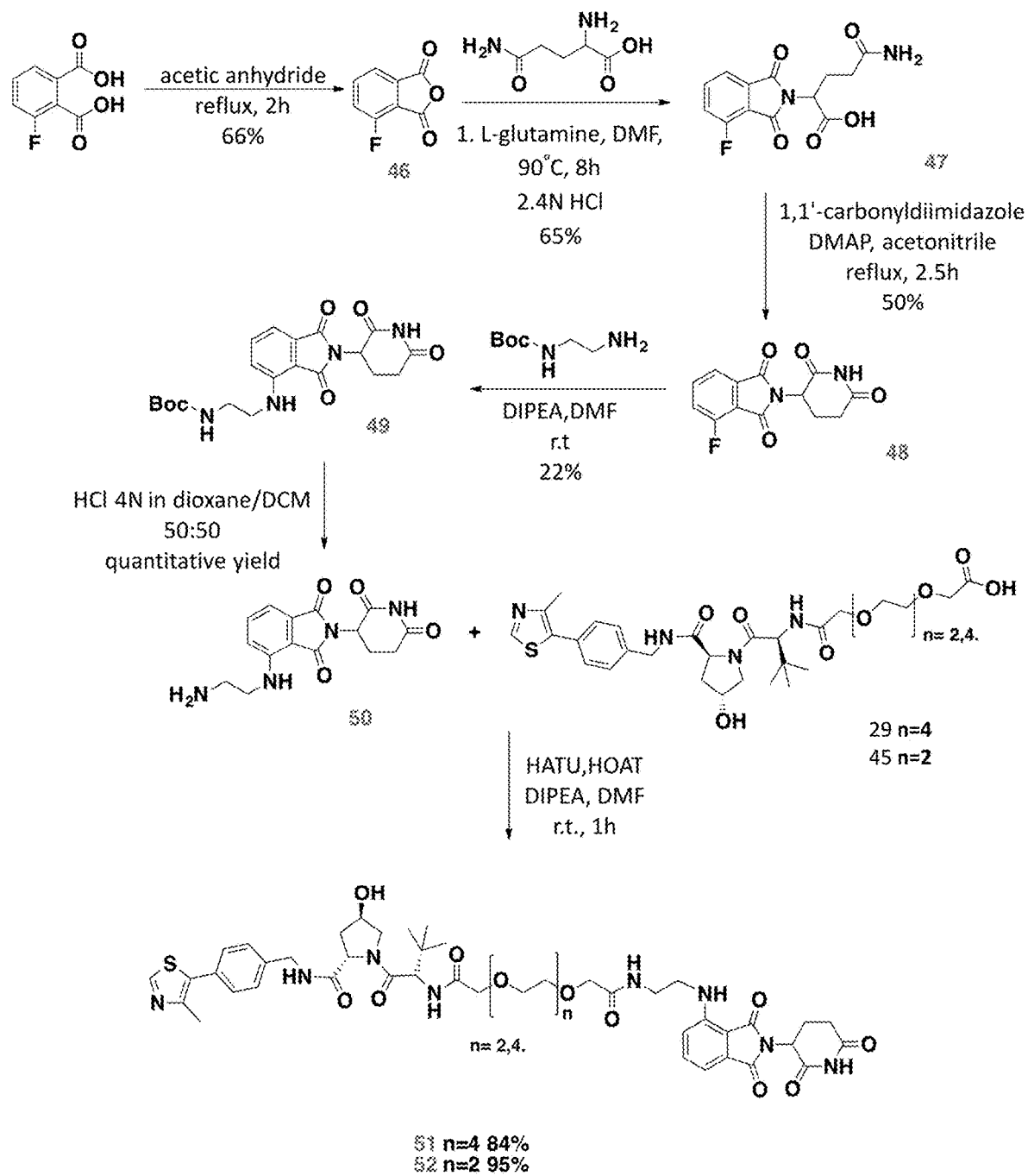
FIG. 25: Synthesis of 52 (CMP85) and 51 (CMP86)

Compound 48 was converted into compound 50 in two steps (FIG. 25), by coupling with N-Boc-ethylenediamine and subsequent Boc deprotection in acidic conditions. Coupling of the latter with 29 or 45 afforded compounds 52 (CMP85) and 51 (CMP86) respectively in good yield.

Biological Evaluation of the VHL-Targeting Compounds

The following section outlines the results of the biological evaluation of PROTAC compounds targeting VHL in cells.

Figure 27:
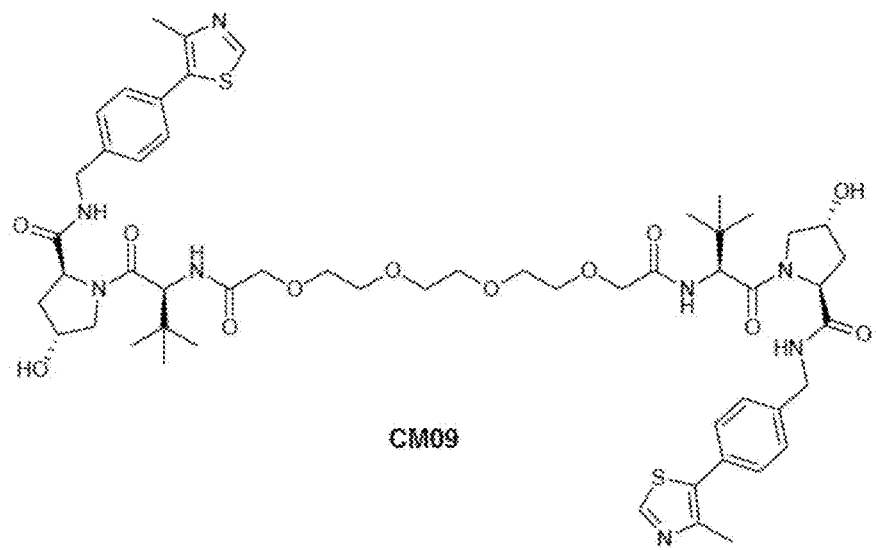
FIG. 27: Chemical structures of CM09, CM10, CM11.
Figure 27:
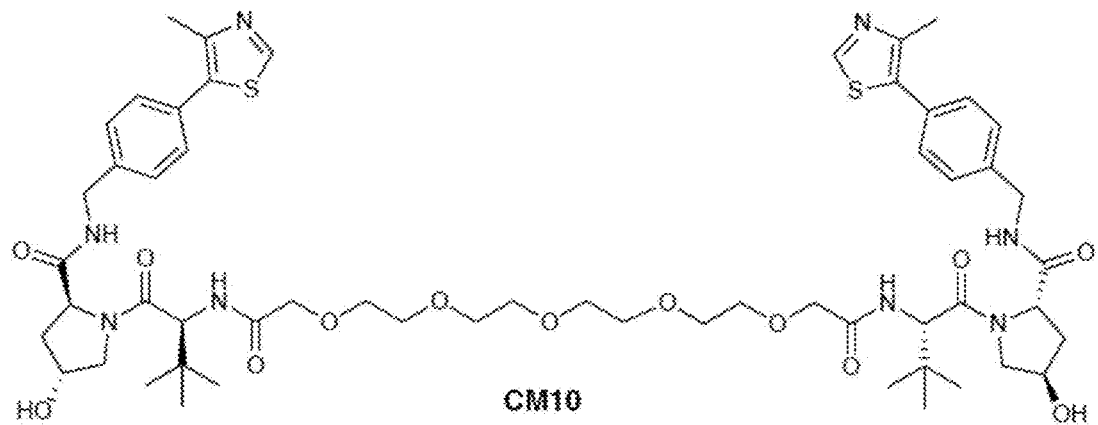
Figure 27:
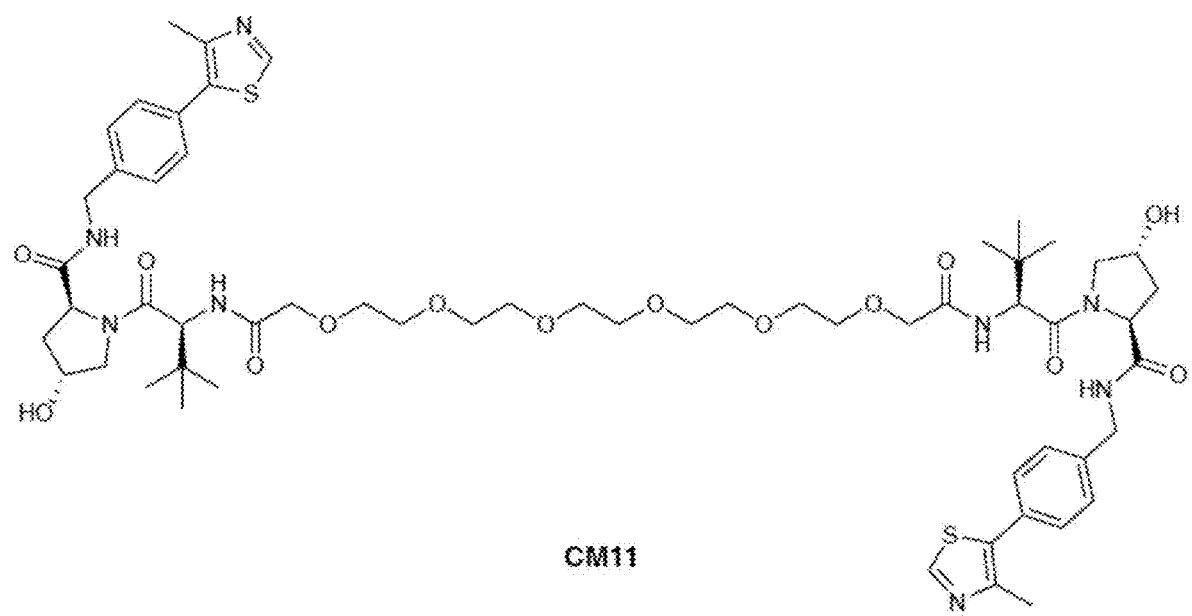

In order to assess the activity of compounds inside cells, HeLa cells were treated with 1 µM of Homo-PROTACs CM09, CM10 and CM11 (FIG. 27) synthesis of which are below, and the above described PROTACs recruiting CRL4$^{CRBN}$ to target VHL, i.e. CMP85 and CMP86. Dimethylsulfoxide (DMSO vehicle, 0.1% v/v), COCl$_2$ (chemical inducer of HIF-1α), IOX2 and IOX4 (selective inhibitor of PHD2), VH032 (selective VHL inhibitor) were used as controls. The samples, obtained after 10 h of treatment and cell lysis, were resolved by SDS-PAGE followed by Western blot using the corresponding specific antibodies to probe for the following proteins (FIG. 28):

VHL: CM09, CM10 and CM11 demonstrated complete depletion of VHL levels, which featured as a preferential or selective degradation of the long isoform pVHL30. However, some degradation of the short isoform pVHL19 was also observed, albeit only around 20%. None of the other compounds were able to induce degradation of VHL.

Cullin2: To assess if treatment with the series of compounds could have any effect on other subunits of the CLR2$^{VHL}$, protein levels of Cullin2 were evaluated. CM10 and CM11 showed to affect Cullin2 levels by inducing a reduction of approximately 20%.

CRBN: No detectable effect was observed on CRBN levels upon treatment with CMP85 and CMP86.

HIF-1α and Hdy-HIF-1α. To evaluate if VHL degraders could induce accumulation of HIF-la, and specifically of its hydroxylated form (Hdy-HIF-1α), levels of these proteins were evaluated. It was observed during siRNA experiments that VHL knockdown does not lead to HIF-1α depletion. Indeed, even very low levels of VHL are capable of highly efficient catalysis on HIF-1α, leading to subsequent effective HIF-1α degradation. As expected, VHL depletion did not impact significantly on HIF-1α level (compare the detected HIF-1α band with vehicle control DMSO). Nevertheless, a slight increase of HIF-1α level was induced by the active VHL degraders CM09, CM10 and CM11 (see HIF-1α band with longer exposure). This effect was even more pronounced on Hdy-HIF-1α, consistent with the stabilized HIF being in the hydroxylated form as expected from VHL knockdown.

PHD2 and PHD3: to study potential hypoxic response of cells due to treatment with the compounds, levels of PHD2 and PHD3 were considered. No effect on the levels of these proteins was observed at this concentration.

Figure 28:
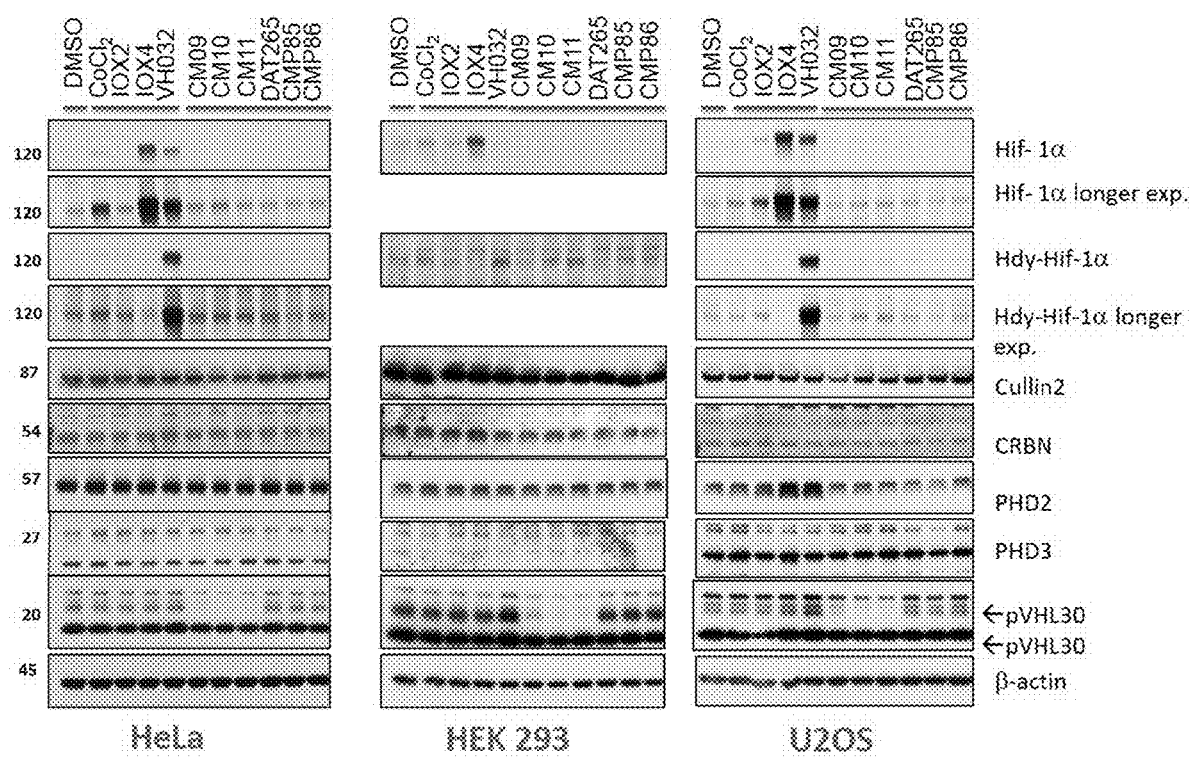
FIG. 28: HeLa, Hek293 and U2OS cells were treated with 1 µM of CM09, CM10, CM11, DAT265, CMP85 or CMP86, 0.1% DMSO, CoCl$_2$ (10 µM), IOX2 (5 µM), IOX4 (5 µM)
Figure 29:
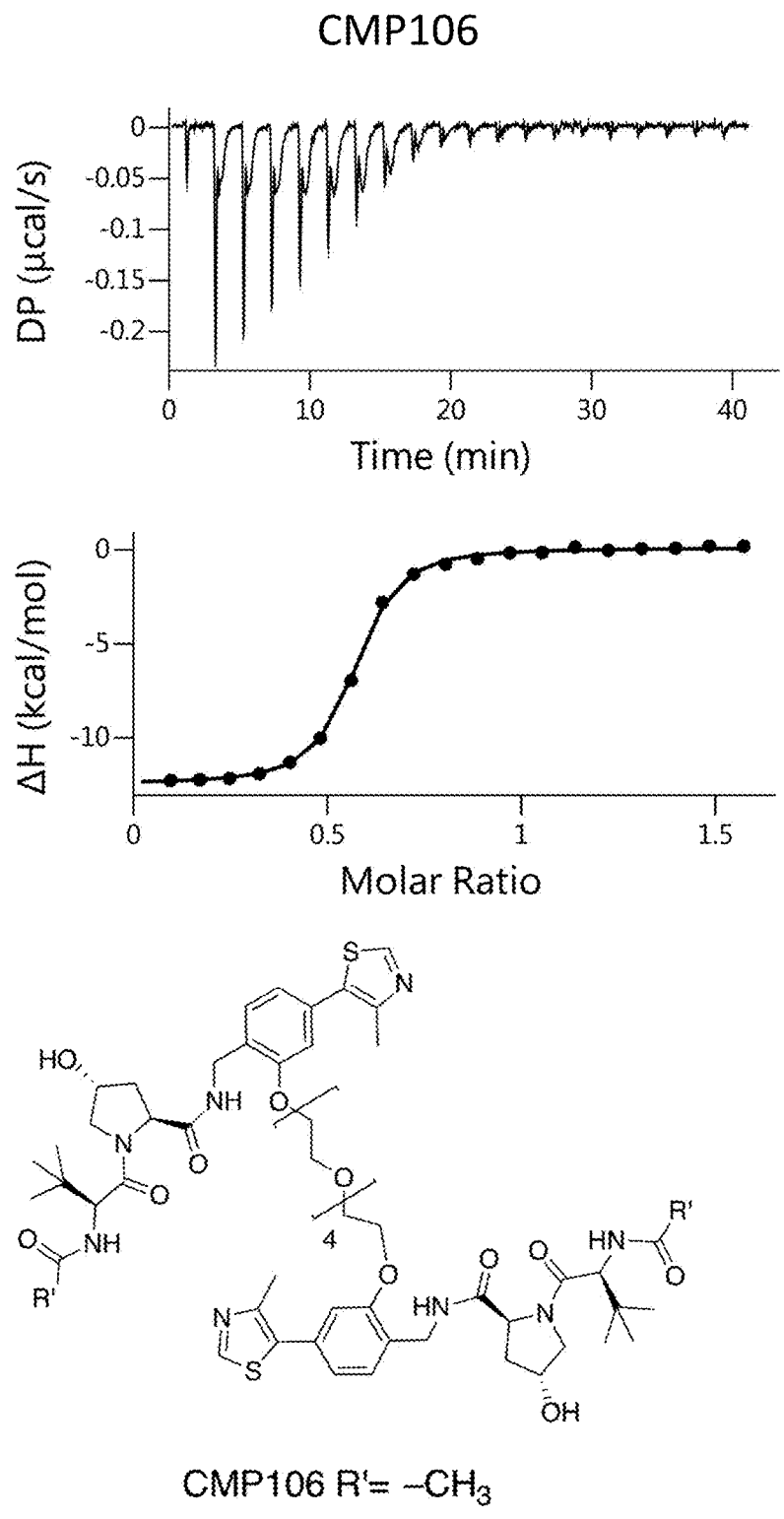
FIG. 29: Integrated ITC heat curve for CMP106 against VCB.
Figure 30:
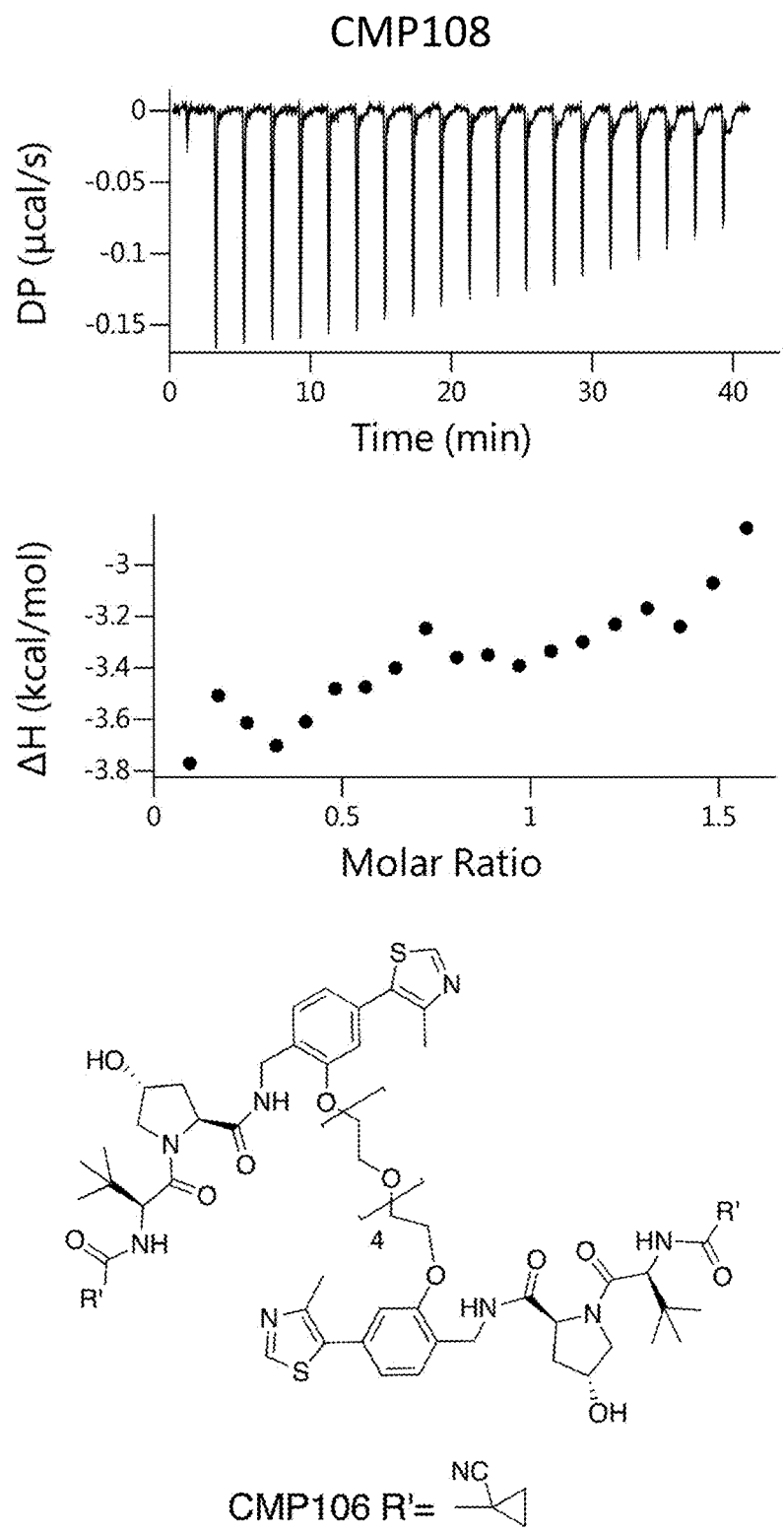
FIG. 30: Integrated ITC heat curve for CMP108 against VCB.
Figure 31:
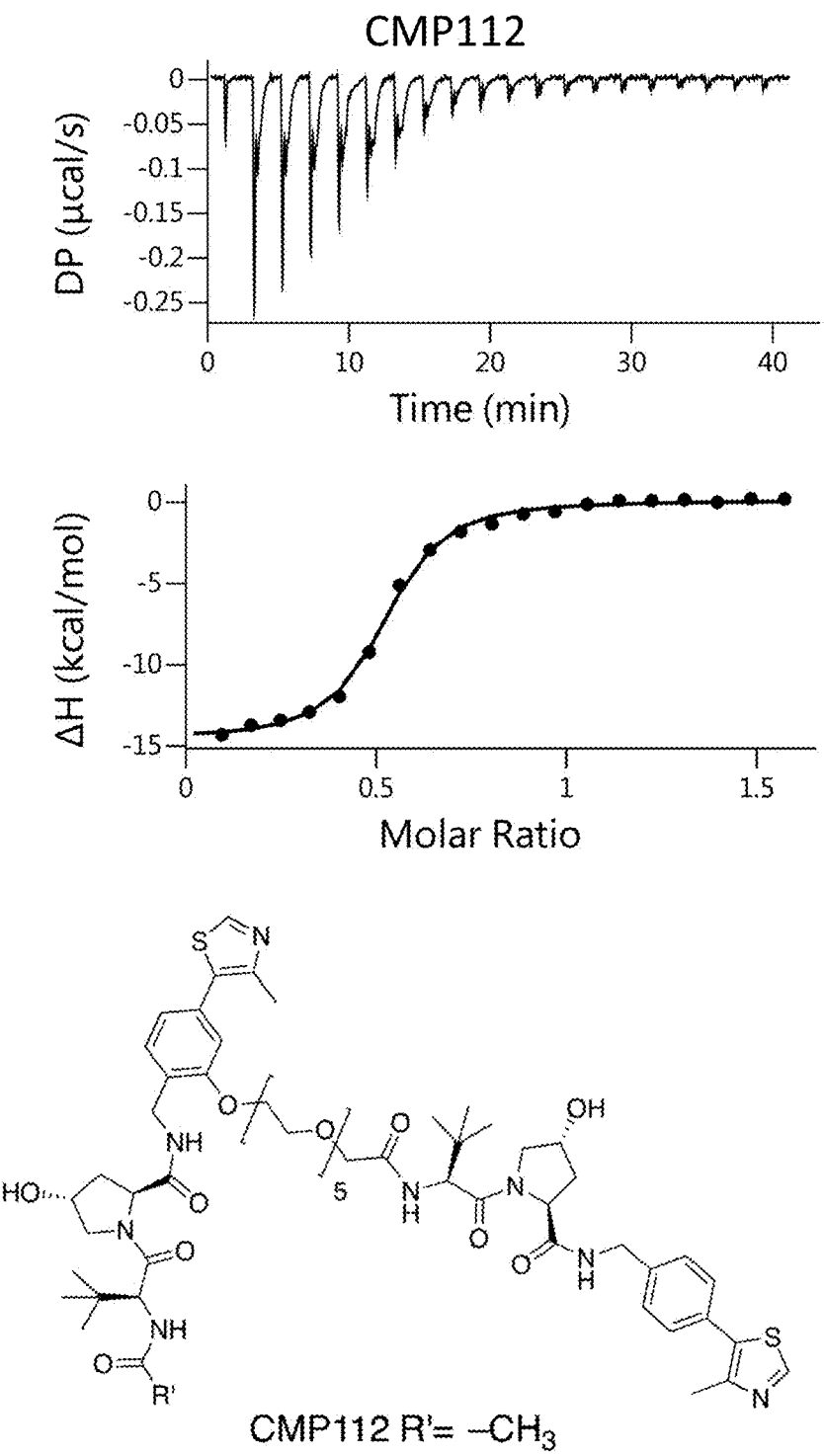
FIG. 31 Integrated ITC heat curve for CMP112 against VCB.
Figure 32:
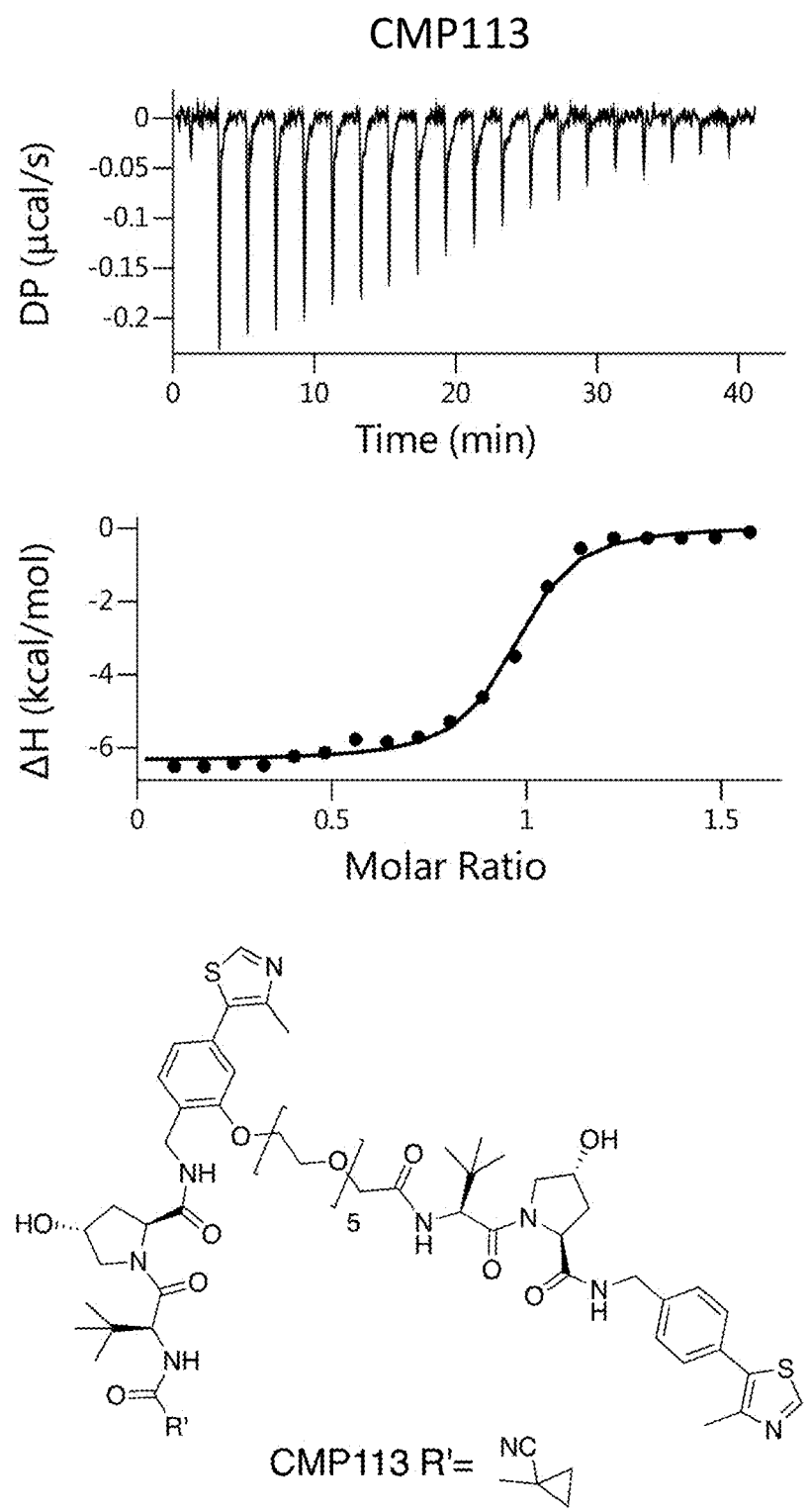
FIG. 32: Integrated ITC heat curve for CMP113 against VCB.

The same experiments were performed in other cells lines to further assess the consistency of the cellular effects of our compounds, as different cell lines can have different expression levels of different proteins. For example, HEK293 are known to have higher expression levels of total VHL, which we confirmed by Western blot (FIG. 28). The same activity profile in decreasing preferentially pVHL30 levels by CM09-11 was observed in HEK 293 (FIG. 28). No major effects were observed on levels of the other proteins. Experiments conducted in U2OS cells showed the same results, confirming that the effect observed upon treatment with CM09, CM10 and CM11 is independent from cell type and it is consistent in all tested cell lines (FIG. 28).

Figure 33:
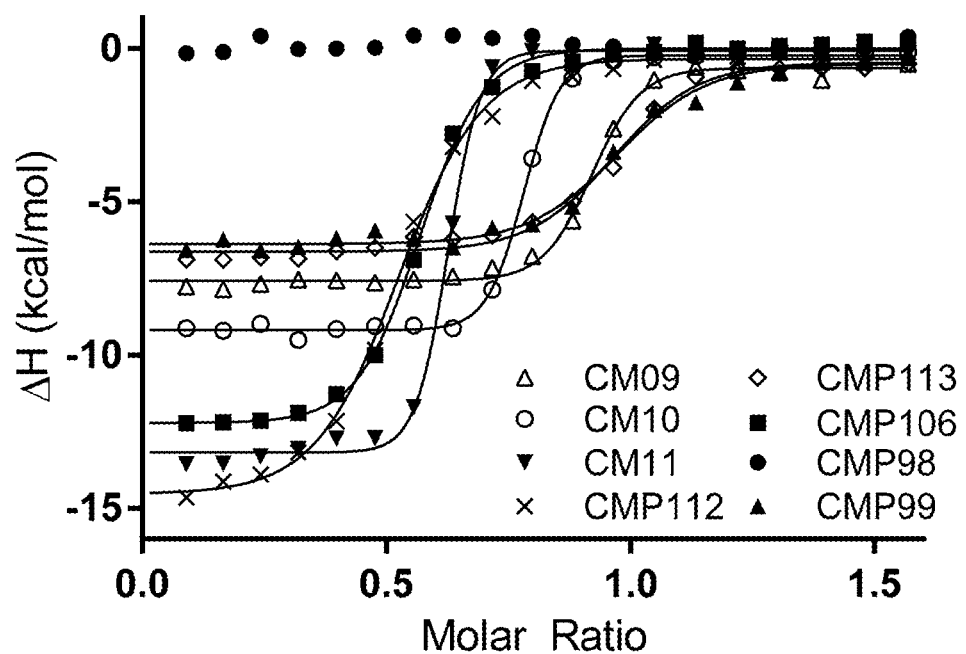
FIG. 33: Superposition of the integrated ITC heat curves for CM09, CM10, CM11, CMP112, CMP113, CMP106, CMP98 and CMP99 against VCB

ITC experiments were also conducted with compounds CMP106, CMP108, CMP112 and CMP113 (data shown in FIGS. 29-32). With the exception of compound CMP108 for which data could not be fitted to a binding curve, all of the other compounds exhibited very similar binding affinity as the individual warhead ligand (cooperativity around 1), suggesting they are much less cooperative than CM11, which is consistent with their lack of activity in cells. This conclusion is illustrated in FIG. 33, where the ITC titrations for compounds CM09-11, CMP112-113, CMP106 as well as control compounds CMP98 and CMP99 are all superposed together in a single Figure, highlighting the remarkable potency and cooperativity of CM11.

Materials and Methods

All chemicals were purchased from commercial vendors and used without further purification, unless indicated otherwise. Reactions were magnetically stirred; commercially available anhydrous solvents were used. All reactions requiring anhydrous conditions were carried out under argon or nitrogen atmosphere using oven-dried glassware. HPLC-grade solvents were used for all reactions. Flash column chromatography was carried out using silica gel (Merck 60 F254 nm). Normal phase TLC was carried out on pre-coated silica plates (Kieselgel 60 F254, BDH) with visualization via UV light (UV 254/365 nm) and/or basic potassium permanganate solution or other suitable stains. Flash column chromatography (FCC) was performed using a Teledyne Isco Combiflash Rf or Rf200i, prepacked columns RediSep Rf Normal Phase Disposable Columns were used. NMR spectra were recorded on a Bruker Ascend 400 or 500. Chemical shifts are reported in parts per million referenced to residual solvent peaks (CDCl$_3$=7.26 ppm). The following abbreviations were used in reporting spectra, s (singlet), d (doublet), t (triplet), q (quartet), m (multiplet), dd (doublet of doublets). Only major rotamer NMR spectra are reported. High Resolution Mass Spectra (HRMS) were recorded on a Bruker microTOF. Low resolution MS and analytical HPLC traces were recorded on an Agilent Technologies 1200 series HPLC connected to an Agilent Technologies 6130 quadrupole LC/MS, connected to an Agilent diode array detector. The column used was a Waters XBridge column (50 mm×2.1 mm, 3.5 µm particle size). The flow rate was 0.6 mL/min. Preparative HPLC was performed on a Gilson Preparative HPLC System with a Waters XBridge C18 column (100 mm×19 mm; 5 µm particle size).

General method A: PEG was solubilised in dioxane anhydrous and NaH was added under stirring. The resulting mixture was stirred at r.t. for 3 h. The mixture was cooled down to 0° C. using ice bath and tert-butylbromo acetate was added drop by drop. The resulting mixture was stirred at r.t O/N. The precipitate was filtered off and the organic phase evaporated to dryness. The resulting oil was taken up with ethyl acetate, washed with water, dried over MgSO$_4$ and evaporated to dryness. The resulting oil was purified by column chromatography using a gradient of ethyl acetate from 50% to 100% v/v in heptane.

General method B: tert-butyl esters 1, 2, 3 or 12 were dissolved in a solution of 50% v/v trifluroacetic acid in DCM. The resulting solution was stirred for 1 h or until complete conversion of starting material. The solvent was removed under high vacuum. The resulting carboxylic acid was used as crude in the next step without any further purification. To a solution of carboxylic acid in 1 ml DMF were added HATU (1 eq.) and HOBT (1 eq.) and the solution was stirred at room temperature for 5 min. Amine 6, 31 or 32 was added and the pH of the reaction mixture was adjusted to >9 by addition of DIPEA (3 eq.). The mixture was stirred at room temperature until no presence of the starting materials was detected by LC-MS. Water was added and the mixture was extracted with ethyl acetate (×3). The combined organic phases were washed with brine (×2), dried over MgSO$_4$ and evaporated under reduced pressure to give the corresponding crude, which was purified by HPLC using a gradient of 20% to 95% v/v acetonitrile in 0.1% aqueous solution of ammonia to yield the desired compound.

General method C: A mixture of mesilate, compound 6, 31, 32, and K$_2$CO$_3$ (41.46 mg, 0.3 mmol, 6 eq.) in DMF was stirred O/N at 70° C. The reaction mixture was filtered off to afford the crude product, which was purified by HPLC using a gradient of 5% to 95% v/v acetonitrile in 0.1% aqueous solution of formic acid to yield the desired compounds.

(2S,4R)-4-hydroxy-N-(2-hydroxy-4-(4-methylthiazol-5-yl)benzyl)pyrrolidine-2-carboxamide hydrochloride (15)

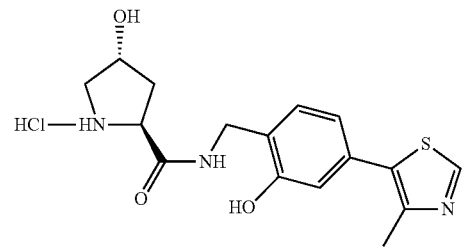 [SMILES: Cc1ncsc1-c1ccc(CNC(=O)[C@@H]2C[C@@H](O)CN2Cl)c(O)c1]

To a solution of trans-N-(tert-Butoxycarbonyl)-4-hydroxy-L-proline (890 mg, 3.84 mmol, 1 eq.) in DMF was added HATU (1.46 g, 3.84 mmol, 1 eq.) and HAOT (522 mg, 3.84 mmol, 1 eq.) and the solution was stirred at room temperature for 5 min. 14 (846 mg, 3.84 mmol, 1 eq.) was added and the pH of the reaction mixture was adjusted to >9 by addition of DIPEA (3 eq.) and the mixture was stirred at room temperature until no presence of the starting materials was detected by LC-MS. Water was added and the mixture was extracted with ethyl acetate (×3). The combined organic phases were washed with brine (×2), dried over MgSO$_4$ and evaporated under reduced pressure to give the corresponding crude, which was purified by flash column chromatography using a gradient of 0 to 80% v/v acetone in heptane to yield the titled compound. Yield: 1.298 g, 3 mmol (78%). Analytical data matched those previously reported[35]

The N-Boc-protected compound was dissolved in DCM. An equal volume of 4M HCl in dioxane was added and the reaction mixture stirred at room temperature for 2 h. The solvent was removed under a stream of nitrogen and dried under reduce pressure. The resulting crude was used for the next step without any further purification (quantitative yield). Analytical data matched those previously reported[35]

(2S,4R)-1-((S)-2-amino-3,3-dimethylbutanoyl)-4-hydroxy-N-(2-hydroxy-4-(4-methylthiazol-5-yl)benzyl)pyrrolidine-2-carboxamide hydrochloride (16)

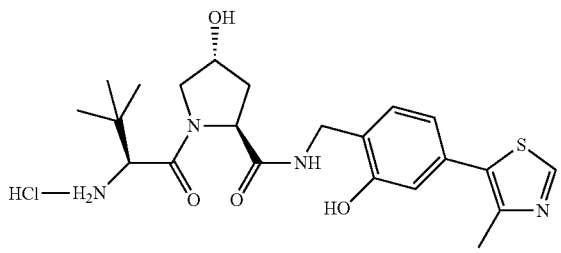 [SMILES: Cc1ncsc1-c1ccc(CNC(=O)[C@@H]2C[C@@H](O)CN2C(=O)[C@@H](NCl)C(C)(C)C)c(O)c1]

To a solution of trans-N-(tert-Butoxycarbonyl)-4-hydroxy-L-proline (890 mg, 3.84 mmol, 1 eq.) in DMF was added HATU (1.46 g, 3.84 mmol, 1 eq.) and HAOT (522 mg, 3.84 mmol, 1 eq.) and the solution was stirred at room temperature for 5 min. 14 (846 mg, 3.84 mmol, 1 eq.) was added and the pH of the reaction mixture was adjusted to >9 by addition of DIPEA (3 eq.) and the mixture was stirred at room temperature until no presence of the starting materials was detected by LC-MS. Water was added and the mixture was extracted with ethyl acetate (×3). The combined organic phases were washed with brine (×2), dried over MgSO$_4$ and evaporated under reduced pressure to give the corresponding crude, which was purified by flash column chromatography using a gradient of 0 to 80% v/v acetone in heptane to yield the titled compound. Yield: 1.915 g, 3.61 mmol (94%). Analytical data matched those previously reported[35].

The N-Boc-protected compound was dissolved in DCM. An equal volume of 4 M HCl in dioxane was added and the reaction mixture stirred at room temperature for 2 h. The solvent was removed under a stream of nitrogen and dried under reduced pressure. The resulting crude was used for the next step without any further purification (quantitative yield). Analytical data matched those previously reported[35].

(2S,4R)-1-((S)-2-(1-cyanocyclopropane-1-carboxamido)-3,3-dimethylbutanoyl)-4-hydroxy-N-(2-hydroxy-4-(4-methylthiazol-5-yl)benzyl)pyrrolidine-2-carboxamide (18)

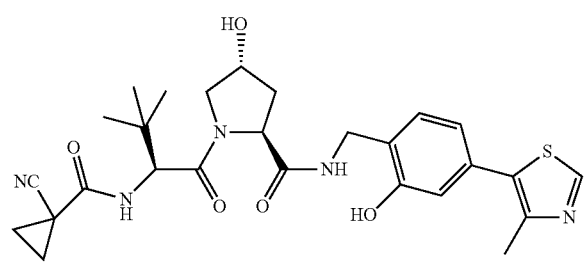 [SMILES: Cc1ncsc1-c1ccc(CNC(=O)[C@@H]2C[C@@H](O)CN2C(=O)[C@@H](NC(=O)C2(C#N)CC2)C(C)(C)C)c(O)c1]

1-cyanocyclopropanecarboxylic acid (69 mg, 0.62 mmol, 1 eq.) was solubilized in 3 ml of DMF. HATU (235 mg, 0.62 mmol, 1 eq.) and HOAT (84.4 mg, 0.62 mmol, 1 eq.) were added and the resulting mixture was stirred at r.t. for 5 min. The amine precursor of 16 (300 mg, 0.62 mmol, 1 eq.) was added and the pH was adjusted to pH>9 using DIPEA (400 mg, 0.5 ml, 3.1 mmol, 5 eq.). The resulting mixture was stirred at r.t. until complete conversion of the starting material. Water was added, and the mixture was extracted with ethyl acetate (×3). The combined organic phases were washed with brine (×1), dried over MgSO$_4$, and evaporated to afford the corresponding crude compound that was purified by flash column chromatography using a gradient of 10% to 70% acetone in heptane to yield the title compound as a white solid. Yield: 200 mg, 0.37 mmol (60%). HRMS (ESI) m/z: [M+H]$^+$ calculated for: C$_{27}$H$_{33}$N$_5$O$_5$S: 539.22; observed: 540.3.

$^1$H NMR (400 MHz, CDCl3) 9.29 (1H, s), 8.65 (1H, s), 8.02 (1H, t, J=6.4 Hz), 7.12 (1H, d, J=7.7 Hz), 6.99 (1H, d, J=8.0 Hz), 6.94 (1H, d, J=1.8 Hz), 6.86 (1H, dd, J=1.8, 7.7 Hz), 4.72 (1H, t, J=8.0 Hz), 4.54 (1H, s), 4.44-4.35 (2H, m), 4.19 (1H, dd, J=5.5, 14.6 Hz), 3.87 (1H, d, J=11.0 Hz), 3.62 (1H, dd, J=3.7, 11.0 Hz), 3.50 (1H, s), 2.49 (3H, s), 2.43-2.37 (1H, m), 2.13-2.06 (1H, m), 1.66-1.37 (4H, m), 0.89 (8H, s); $^{13}$C NMR (101 MHz, CDCl$_3$) δ 172.8, 170.8, 165.8, 155.8, 150.5, 148.3, 133.3, 131.6, 131.2, 123.9, 120.9, 119.6, 118.2, 70.1, 58.6, 58.3, 56.7, 55.7, 40.0, 35.7, 26.2, 18.6, 17.9, 17.8, 17.2, 16.1, 13.8.

(2S,4R)-1-((S)-2-acetamido-3,3-dimethylbutanoyl)-4-hydroxy-N-(2-hydroxy-4-(4-methylthiazol-5-yl)benzyl)pyrrolidine-2-carboxamide (17)

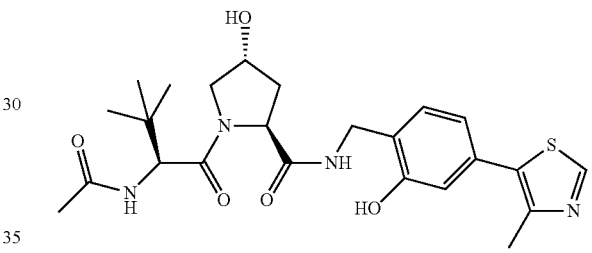

The amine precursor 16 (100.7 mg, 0.240 mmol, 1 eq.) was dissolved in 1 ml of DMF, acetylimidazole (31.7 mg, 0.288 mmol, 1.2 eq) and DIPEA (0.090 ml, 0.48 mmol, 2 eq.) were added to the solution. After stirring the mixture for 48 h at room temperature, the solvent was evaporated under reduced pressure to give the corresponding crude, which was purified by HPLC using a gradient of 5% to 95% v/v acetonitrile in 0.1% aqueous solution of formic acid to yield the titled compound. Yield: 91 mg, 0.187 mmol (78%). $^1$H NMR (400 MHz, CDCl$_3$) 9.25 (1H, s), 8.70 (1H, s), 7.97 (1H, t, J=6.5 Hz), 7.15 (1H, d, J=7.5 Hz), 6.83-6.80 (2H, m), 6.72 (1H, d, J=8.8 Hz), 4.92-4.88 (1H, m), 4.57 (1H, s), 4.52-4.42 (2H, m), 4.26-4.14 (2H, m), 3.59 (1H, dd, J=2.9, 11.1 Hz), 2.53-2.45 (4H, m), 2.24-2.17 (1H, m), 1.85 (3H, s), 0.83 (9H, s); $^{13}$C NMR (101 MHz, CDCl$_3$) δ 171.8, 171.2, 155.9, 150.7, 148.1, 132.8, 131.7, 131.0, 124.2, 120.6, 117.1, 70.3, 58.1, 57.7, 57.1, 39.8, 35.5, 34.8, 26.3, 22.6, 16.0. HRMS (ESI) m/z: [M+H]$^+$ calculated for: C$_{24}$H$_{32}$N$_4$O$_5$S: 488.21; observed: 484.3.

di-tert-butyl 3,6,9,12-tetraoxatetradecanedioate (1)

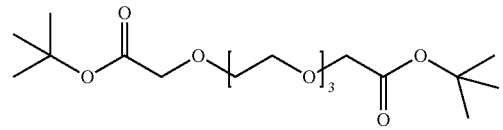

Following general method A, from triethylene glycol (1.125 g, 1 ml, 7.49 mmol, 1 eq.) in 10 ml of dioxane, NaH 60% in mineral oil (595.75 mg, 14.9 mmol, 2 eq.) and tert-Butyl bromoacetate (2.905 g, 2.19 ml, 14.9 mmol, 2 eq.), compound 1 was obtained as an oil after high vacuum. Yield: 538 mg, 1.42 mmol (19%).

$^1$H NMR (500 MHz, CDCl$_3$) δ 3.81 (4H, s), 3.51-3.46 (12H, m), 1.26 (18H, s). $^{13}$C NMR (126 MHz, CDCl$_3$) δ 169.1, 80.9, 70.1, 70.0, 68.5, 27.5. Analytical data matched those previously reported.39 di-tert-butyl 3,6,9,12,15-pentaoxaheptadecanedioate (2)

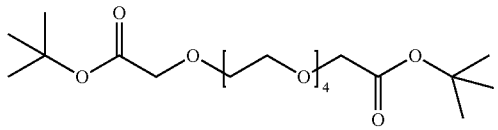

Following general method A, from tetrathylene glycol (1.125 g, 1 ml, 5.49 mmol, 1 eq.) in 10 ml of dioxane, NaH 60% in mineral oil (463 mg, 11.5 mmol, 2 eq.) and tert-Butyl bromoacetate (2.25 g, 1.7 ml, 11.5 mmol, 2 eq.), compound 2 was obtained as an oil after high vacuum. Yield: 500 mg, 1.18 mmol (10%).

$^1$H NMR (500 MHz, CDCl$_3$) δ 3.86 (4H, s), 3.55-3.49 (16H, m), 1.31 (9H, s). Analytical data matched those previously reported.$^{39}$ di-tert-butyl 3,6,9,12,15,18-hexaoxaicosanedioate (3)

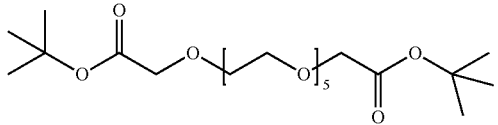

Following general method A, from pentaethylene glycol (1.126 g, 1 ml, 4.72 mmol, 1 eq.) in 10 ml of dioxane, NaH 60% in mineral oil (377 mg, 9.45 mmol, 2 eq.) and tert-Butyl bromoacetate (1.872 g, 1.7 ml, 11.5 mmol, 2 eq.), compound 3 was obtained as an oil after high vacuum. Yield: 300 mg, 0,641 mmol (14%).

$^1$H NMR (400 MHz, CDCl$_3$) δ 3.94 (4H, s), 3.66-3.56 (20H, m), 1.40 (18H, s). Analytical data matched those previously reported$^{39}$.

1-phenyl-2,5,8,11,14-pentaoxahexadecan-16-ol (9)

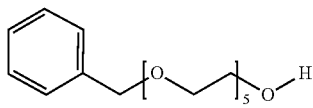

Pentaethylene glycol (9.53 g, 50 mmol, 5 eq.) was added dropwise to a suspension of NaH 60% in mineral oil (800 mg, 20 mmol, 2.5 eq.) in 20 ml of DMF at 0° C. The resulting mixture was stirred at r.t for 1 h. The reaction mixture was cooled to 0° C., benzyl chloride (1 ml, 1.1 g, 8.72 mmol, 1 eq.) was added. The resulting mixture was stirred O/N at r.t. The reaction was quenched with a saturated solution of NH$_4$Cl and the aqueous phase was extracted with ethyl acetate (×3). The combined organic phases were dried over MgSO$_4$ and evaporated to dryness. The resulting oil was purified by column chromatography (from 0 to 60% of ethyl acetate in heptane) to afford the title compound as an oil. Yield: 2.055 g, 6.25 mmol (71%).

$^1$H NMR (400 MHz, CDCl$_3$) δ 7.28-7.19 (5H, m), 4.50 (2H, s), 3.66-3.52 (20H, m), 2.50 (1H, s). $^{13}$C NMR (101 MHz, CDCl$_3$) 138.2, 128.3, 127.8, 127.6, 73.2, 72.7, 70.61, 70.58, 70.53, 70.51, 70.2, 69.4, 61.7 tert-butyl 1-phenyl-2,5,8,11,14,17-hexaoxanonadecan-19-oate (10)

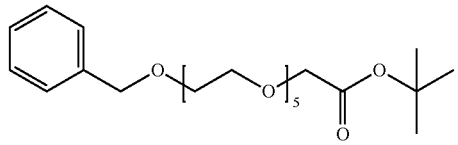

To a stirred solution of 9 (2.055 g, 6.25 mmol, 1 eq.) in 12.8 ml of DCM was added 37% solution of NaOH (12.8 ml), followed by tert-butylbromo acetate (4.882 g, 25 mmol, 4 eq.) and TBABr (2118 mg, 6.37 mmol, 1.02 eq.). The resulting solution was stirred O/N at r.t. The reaction mixture was extracted with ethyl acetate (×3). The organic phases were combined and washed with brine (×1), dried over MgSO$_4$ and concentrate in vacuo. The resulting brown oil was purified by column chromatography (from 0 to 30% of ethyl acetate in petroleum) to afford the titled compound as colourless oil. Yield: 2.216 g, 5 mmol (80%).

$^1$H NMR (500 MHz, CDCl$_3$) δ 7.28-7.20 (5H, m), 4.50 (2H, s), 3.95 (2H, s), 3.65-3.55 (20H, m), 1.40 (9H, s). $^{13}$C NMR (126 MHz, CDCl$_3$) δ169.7, 128.4, 127.7, 127.6, 81.5, 73.2, 70.7, 70.7, 70.6, 70.6, 69.4, 69.1, 28.1. HRMS (ESI) m/z: [M+H]$^+$ calculated for: C$_{23}$H$_{38}$O$_8$: 442.26; observed: 387.2.

19,19-dimethyl-17-oxo-3,6,9,12,15,18-hexaoxaicosanoic acid (11)

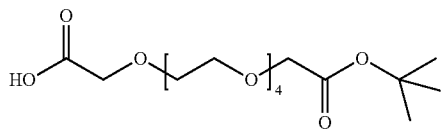

10 (2.216 g, 5 mmol, 1 eq.) was dissolved in 75 ml of ethanol, Pd/C (10 wt %) was added and the resulting mixture was place under hydrogen and stirred at r.t. until complete conversion of the starting material. The reaction mixture was filtered through celite, the celite pad was washed few times using ethanol. The filtrate was concentrated in vacuum to give an oil that was used for the next step without further purification. Yield: 1.764 g, 5 mmol (quantitative). BAIB (3.546 g, 11.01 mmol, 2.2 eq.) and TEMPO (171.87 mg, 1.10 mmol, 0.22 eq.) were added to a solution of ACN/H$_2$O 1:1 containing previous obtained oil (1.764 g, 5 mmol, 1 eq.). The resulting mixture was stirred at r.t until complete conversion of the starting material. The crude was purified using ISOLUTE® PE-AX anion exchange column. The column was equilibrate with methanol, the reaction mixture poured in the column and let it adsorbed in the pad. The column was washed with methanol (×3) to elute all the unbound material. Then, the titled product was eluted using a 50% solution of formic acid in methanol. The organic phase was evaporated to dryness to afford the title compound as oil. Yield: 1.200 g, 3.27 mmol (65%).

¹H NMR (400 MHz, CDCl₃) δ, ppm 4.12 (2H, s), 3.98 (2H, s), 3.72-3.60 (16H, m), 1.43 (9H, s). ¹³C NMR (101 MHz, CDCl₃) δ, ppm 172.6, 169.7, 81.6, 71.0, 70.59, 70.56, 70.54, 70.46, 70.38, 70.35, 70.30, 68.9, 68.8, 28.1.

3,6,9,12-tetraoxatetradecane-1,14-diyl dimethanesulfonate (19)

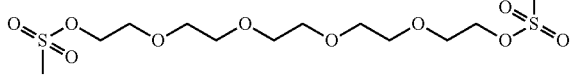

Pentaethylene glycol (476.56 mg, 0.423 ml, 2 mmol, 1 eq.) was dissolved in 4 ml of dry DCM. The temperature of the resulting mixture was cooled down to 0° C. and methanesulfonyl chloride (687.3 mg, 0.464 ml, 16 mmol, 3 eq.) was added followed by triethylamine (1011.9 g, 1.39 ml, 10 mmol, 5 eq.). The resulting mixture was stirred at 0° C. for 4 h. A 10% aqueous solution of NaHSO₄ was added till pH=3. The aqueous phase was extracted with DCM (×5). The organic phases were combined, dried over MgSO₄ and concentrated in vacuum to afford the title compound as an orange oil. Yield: 701 mg, 1.77 mmol (89%).

¹H NMR (400 MHz, CDCl₃) δ 4.33-4.30 (4H, m), 3.72-3.69 (4H, m), 3.62-3.56 (12H, m), 3.02 (6H, s). Analytical data matched those previously reported [Kimura et al. *J. Polym. Sci. Part A: Polym. Chem.* 54, (2016).]

tert-butyl 17-((methylsulfonyl)oxy)-3,6,9,12,15-pentaoxaheptadecanoate (20)

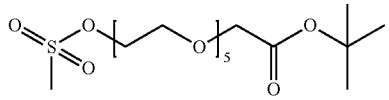

10 (251 mg, 0.712 mmol, 1 eq.) was dissolved in 1.4 ml of dry DCM. The temperature of the resulting mixture was cooled down to 0° C. and methanesulfonyl chloride (122.3 mg, 0.082 ml, 1.068 mmol, 1.5 eq.) was added followed by triethylamine (216.14 mg, 0.3 ml, 2.136 ml, 3 eq.). The resulting mixture was stirred at 0° C. for 4 h. A 10% aqueous solution of NaHSO₄ was added till pH=3. The aqueous phase was extracted with DCM (×5). The organic phases were combined, dried over MgSO₄ and concentrated in vacuum to afford the title compound as a orange oil. Yield: 276 mg, 0.641 mmol (90%).

¹H NMR (400 MHz, CDCl₃) δ 4.32-4.30 (2H, m), 3.95 (2H, s), 3.71-3.57 (18H, m), 3.02 (3H, s), 1.41 (9H, s). ¹³C NMR (101 MHz, CDCl₃) δ 169.7, 81.5, 70.72, 70.65, 70.61, 70.58, 70.5, 69.3, 69.0, 37.7, 28.1.

tert-butyl (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoate (12)

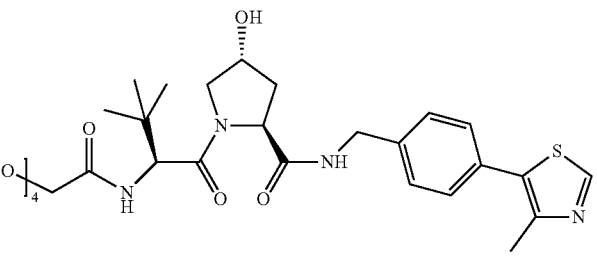

To a solution of PEG linker 11 (78.8 mg, 0.215 mmol, 1 eq.) in 1.5 ml DMF was added HATU (81.74 mg, 0.215 mmol, 1 eq.), HOAT (29.26 mg, 0.215 mmol, 1 eq.), DIPEA and the solution was stirred at room temperature for 5 min. Compound 7 (100 mg, 0.215 mmol, 1 eq.) was added and the pH of the reaction mixture was adjusted to >9 by addition of DIPEA (80.13 mg, 0.106 ml, 0.645 mmol, 3 eq.). The mixture was stirred at room temperature until no presence of the starting materials was detected by LC-MS. The solvent was evaporated under reduced pressure to give the corresponding crude, which was purified by HPLC using a gradient of 20% to 95% v/v acetonitrile in 0.1% aqueous solution of ammonia to yield the titled compound as white solid. Yield: 75.6 mg, 0.094 mmol (44%).

¹H NMR (400 MHz, CDCl₃): δ ppm 9.00 (1H, s), 7.45 (1H, t, J=5.9 Hz), 7.39-7.33 (4H, m), 7.29 (1H, d, J=8.9 Hz), 4.71 (1H, t, J=8.0 Hz), 4.59-4.48 (3H, m), 4.34 (1H, dd, J=5.2, 14.6 Hz), 4.08-3.92 (5H, m), 3.69-3.61 (18H, m), 2.52 (3H, s), 2.47-2.41 (1H, m), 2.19-2.11 (1H, m), 1.46 (9H, s), 0.97 (9H, s). ¹³C NMR (101 MHz, CDCl₃) δ 171.3, 171.1, 170.5, 170.0, 151.7, 139.1, 129.4, 128.3, 82.0, 71.1, 70.6, 70.4, 70.4, 70.3, 70.3, 70.2, 70.2, 68.9, 58.7, 57.3, 56.8, 43.1, 36.3, 35.1, 28.1, 26.4, 15.1. HRMS (ESI) m/z: [M+H]⁺ calculated for: $C_{38}H_{58}N_4O_{11}S_2$: 778.38; observed: 779.4.

$N^1$—((R)-1-((2R,4R)-4-hydroxy-2-((4-(4-methylthiazol-5-yl)benzyl)carbamoyl)pyrrolidin-1-yl)-3,3-dimethyl-1-oxobutan-2-yl)-$N^{17}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide (CMP99)

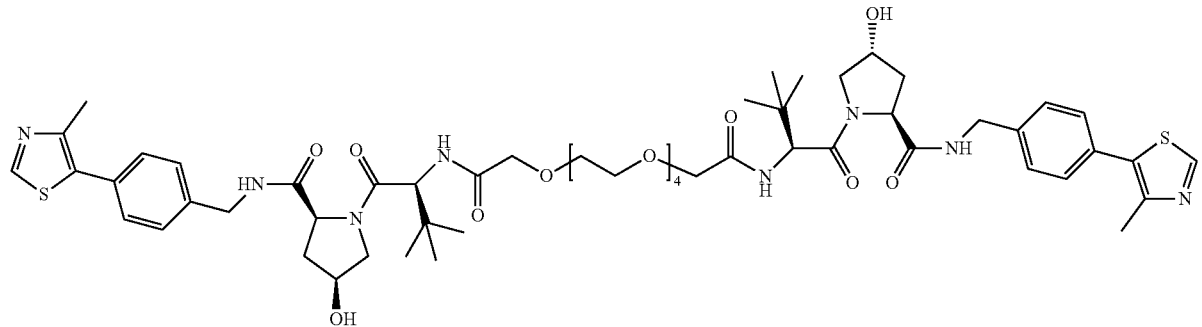

Following general method B, from compound 12 (75.6 mg, 0.094 mmol, 1 eq.) and trifluoroacetic acid (1 ml in 1 ml of DCM), the carboxylic acid derivative was obtained as oil. The crude was used for the next step without further purification. Yield: 70 mg, 0.094 mmol (quantitative). MS (ESI) m/z: [M+H]$^+$ calculated for: $C_{34}H_{50}N_4O_{11}S$: 722.32; observed: 723.3. Following general method B, from compound 13 (5.5 mg, 0.006 mmol, 1 eq.), compound 8 (2.77 mg, 0.006 mmol, 1 eq.), HATU (2.28 mg, 0.0.006 mmol, 1 eq.), HOAT (1 mg, 0.0.006 mmol, 1 eq.), DIPEA (2.23 mg, 0.002 ml, 0.018 mmol, 3 eq.), CMP99 was obtained as a white solid. Yield: 4.5 mg, 0.004 mmol (66%).

$^1$H NMR (400 MHz, CDCl$_3$): d, ppm 8.74 (2H, d, J=2.8 Hz), 7.37-7.34 (9H, m), 7.18 (1H, d, J=8.9 Hz), 4.76-4.64 (3H, m), 4.59-4.44 (5H, m), 4.37-4.26 (2H, m), 4.05-3.59 (27H, m), 2.52 (6H, s), 2.31-2.11 (4H, m), 0.96 (9H, s), 0.95 (9H, s). HRMS (ESI) m/z: [M+H]$^+$ calculated for: $C_{56}H_{78}N_8O_{13}S_2$: 1134.51; observed: 1135.58.

$N^1,N^{14}$-bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide (CM09)

Following general method B, from compound 1 (6.80 mg, 0.018 mmol, 1 eq.), compound 7 (20 mg, 0.045 mmol, 2.5 eq.), HATU (17 mg, 0.045 mmol, 2.5 eq), HOAT (6.12, 0.045 mmol, 2.5 mmol), DIPEA (6.98 mg, 0.054 mmol, 3 eq) compound CM09 was obtained as a white solid. Yield: 8 mg, 0.007 mmol (40%).

$^1$H NMR (400 MHz, CDCl$_3$) δ 8.61 (2H, s), 7.48-7.45 (2H, m), 7.31-7.27 (8H, m), 7.23 (2H, d, J=10.2 Hz), 4.64-4.59 (2H, m), 4.52-4.46 (4H, m), 4.41-4.38 (2H, m), 4.31-4.25 (2H, m), 4.01-3.94 (4H, m), 3.82 (2H, d, J=15.7 Hz), 3.62-3.52 (12H, m), 2.45 (6H, s), 2.42-2.34 (2H, m), 2.12-2.06 (2H, m), 1.19 (2H, s), 0.89 (18H, s); $^{13}$C NMR (101 MHz, CDCl$_3$) δ 170.2, 169.9, 169.6, 149.3, 147.5, 137.3, 130.6, 129.9, 128.4, 127.1, 69.9, 69.5, 69.3, 69.1, 57.6, 56.1, 55.9, 42.2, 35.5, 34.6, 25.4, 15.1. HRMS (ESI) m/z: [M+H]$^+$ calculated for: $C_{54}H_{74}N_3O_{12}S_2$: 1090.49; observed: 1091.4.

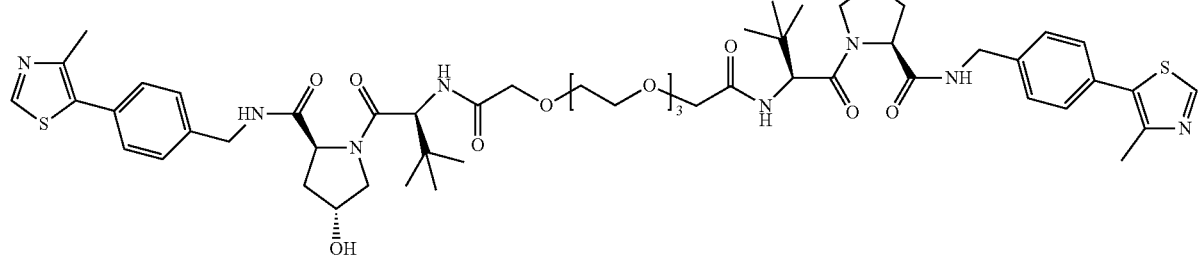

$N^1,N^{17}$-bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide (CM10)

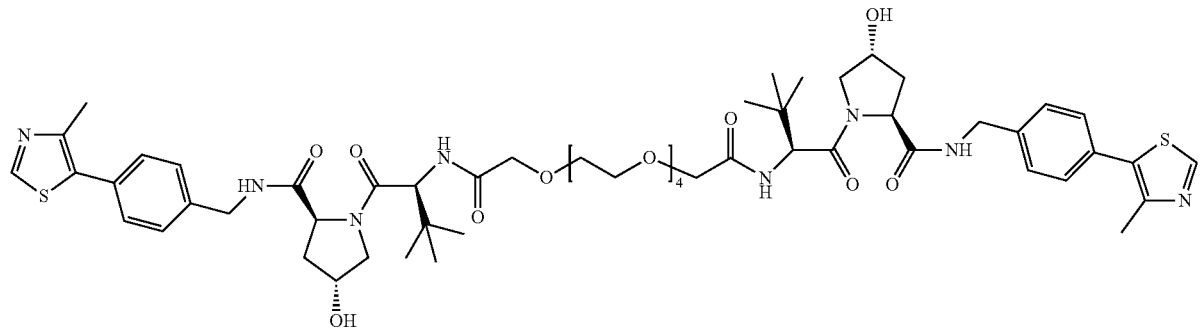

Following general method B, from compound 2 (7.60 mg, 0.018 mmol, 1 eq.), compound 7 (20 mg, 0.045 mmol, 2.5 eq.), HATU (17 mg, 0.045 mmol, 2.5 eq), HOAT (6.12, 0.045 mmol, 2.5 mmol), DIPEA (6.98 mg, 0.054 mmol, 3 eq) compound CM10 was obtained as a white solid. Yield: 6 mg, 0.005 mmol (30%).

$^1$H NMR (400 MHz, MeOD) δ 9.28 (2H, s), 7.43-7.36 (10H, m), 5.39 (2H, s), 4.77 (10H, s), 4.59 (2H, s), 4.50-4.43 (4H, m), 4.42-4.38 (2H, m), 4.26 (2H, d, J=17.2 Hz), 3.96-3.92 (4H, m), 3.77 (2H, d, J=11.1 Hz), 3.73-3.68 (2H, m), 3.56 (16H, m), 3.22-3.20 (10H, m), 2.43 (6H, s), 2.16-2.14 (2H, m), 2.13 (2H, m), 2.02-1.95 (2H, m); $^{13}$C NMR (101 MHz, CDCl$_3$) δ 173.1, 172.4, 170.7, 170.3, 153.3, 153.2, 144.5, 140.0, 134.0, 129.2, 129.0, 128.4, 128.3, 127.8, 70.9, 70.5, 70.2, 70.1, 69.7, 68.2, 67.7, 59.7, 59.4, 56.8, 56.7, 54.9, 42.9, 42.3, 39.9, 37.6, 36.3, 35.7, 34.7, 25.6, 25.5, 13.1. HRMS (ESI) m/z: [M+H]$^+$ calculated for: C$_{56}$H$_{78}$N$_8$O$_{13}$S$_2$: 1134.51; observed: 1135.55.

$N^1,N^{20}$-bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15,18-hexaoxaicosanediamide (CM11)

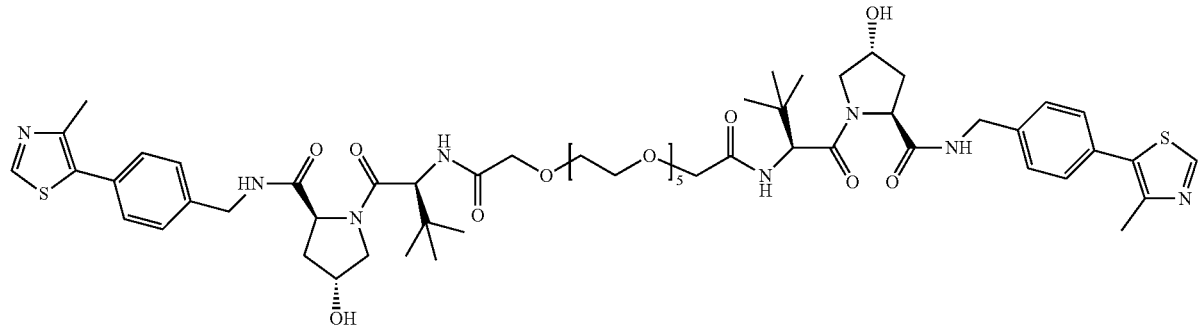

Following general method B, from compound 3 (8.39 mg, 0.018 mmol, 1 eq.), compound 7 (20 mg, 0.045 mmol, 2.5 eq.), HATU (17 mg, 0.045 mmol, 2.5 eq), HOAT (6.12, 0.045 mmol, 2.5 mmol), DIPEA (6.98 mg, 0.054 mmol, 3 eq) compound CM11 was obtained as a white solid. Yield: 11.74 mg, 0.0099 mmol (55%).

$^1$H NMR (400 MHz, CDCl$_3$) δ 8.61 (2H, s), 7.41-7.38 (2H, m), 7.29 (10H, t, J=7.6 Hz), 4.66-4.61 (2H, m), 4.49-4.41 (6H, m), 4.35-4.29 (2H, m), 3.98-3.91 (6H, m), 3.62-3.50 (24H, m), 2.45 (6H, s), 2.42-2.35 (2H, m), 2.11-2.06 (2H, m), 0.88 (18H, s); $^{13}$C NMR (101 MHz, CDCl$_3$) δ 171.2, 170.9, 170.4, 150.3, 148.5, 138.3, 131.6, 130.9, 129.5, 128.1, 71.2, 70.61, 70.59, 70.5, 70.4, 70.3, 58.6, 57.0, 43.2, 36.5, 35.6, 26.4, 16.1. HRMS (ESI) m/z: [M+H]$^+$ calculated for: C$_{58}$H$_{32}$N$_8$O$_{14}$S$_2$: 1178.54; observed: 1179.60.

N$^1$,N$^{20}$-bis((S)-1-((2S,4S)-4-hydroxy-2-((4-(4-methylthiazol-5-yl)benzyl)carbamoyl)pyrrolidin-1-yl)-3,3-dimethyl-1-oxobutan-2-yl)-3,6,9,12,15,18-hexaoxaicosanediamide (CMP98)

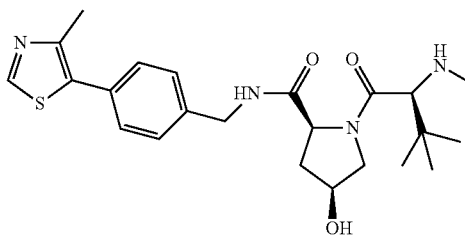
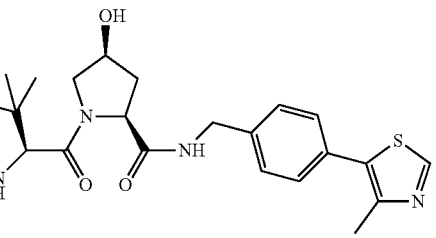

Following general method B, from compound 3 (7.12 mg, 0.028 mmol, 1 eq.), compound 8 (18.06, 0.040 mmol, 2.1 eq.), HATU (15.2 mg, 0.040 mmol, 2 eq.), HOAT (5.44 mg, 0.040 mmol, 2 eq.), DIPEA (7.45 mg, 0.0010 ml, 3 eq.), compound CMP98 was obtained as a white solid. Yield: 10.58 mg, 0.0089 mmol (45%).

$^1$H NMR (400 MHz, CDCl$_3$) δ 9.09 (2H, s), 8.02 (2H, s), 7.31 (4H, d, J=8.5 Hz), 7.22 (4H, d, J=8.0 Hz), 7.16 (2H, d, J=9.2 Hz), 4.75-4.64 (4H, m), 4.51 (2H, d, J=8.9 Hz), 4.41-4.37 (2H, m), 4.24-4.17 (2H, m), 3.94 (4H, d, J=3.2 Hz), 3.84-3.81 (4H, m), 3.62-3.54 (20H, m), 2.49-2.47 (2H, m), 2.44 (6H, s), 2.26-2.17 (4H, m), 0.93 (18H, s); $^{13}$C NMR (101 MHz, CDCl$_3$) δ 173.2, 171.5, 169.7, 151.8, 138.8, 132.9, 129.5, 129.2, 128.3, 71.2, 71.1, 70.6, 70.48, 70.45, 70.4, 70.3, 59.9, 58.5, 56.5, 43.2, 35.6, 35.2, 26.4, 15.0. HRMS (ESI) m/z: [M+H]$^+$ calculated for: C$_{58}$H$_{32}$N$_3$O$_{14}$S$_2$: 1178.54; observed: 1179.60.

(2S,2'S,4R,4'R)—N,N'-((((3,6,9,12-tetraoxatetradecane-1,14-diyl)bis(oxy))bis(4-(4-methylthiazol-5-yl)-2,1-phenylene))bis(methylene))bis(1-((S)-2-(1-cyanocyclopropane-1-carboxamido)-3,3-dimethylbutanoyl)-4-hydroxypyrrolidine-2-carboxamide) (CMP108)

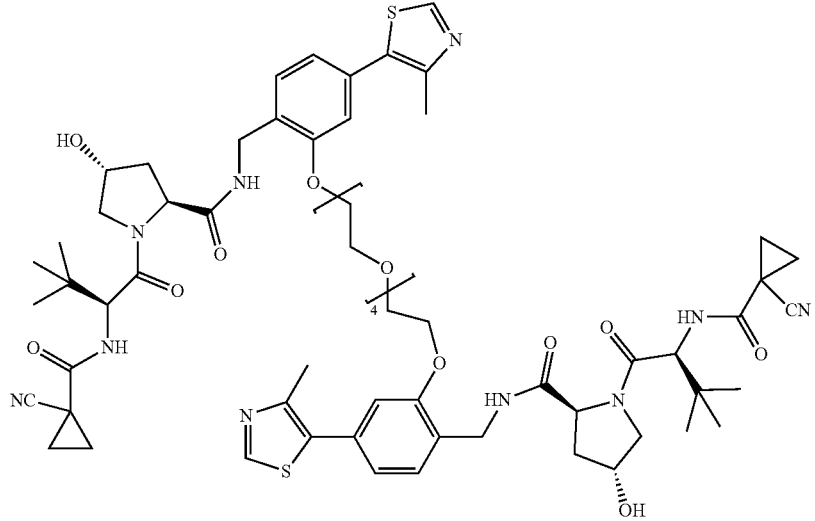

Following general method C, from 18 (27 mg, 0.05 mmol, 2 eq.), 19 (11.83 mg, 0.03 mmol, 1.2 eq.) and K₂CO₃ (41.46 mg, 0.3 mmol, 6 eq.), the titled compound was obtained as a white solid. Yield: 9.1 mg, 0.007 mmol (28%).

¹H NMR (400 MHz, CDCl₃) δ 8.61 (2H, s), 7.41-7.38 (2H, m), 7.26 (2H, d, J=8.1 Hz), 7.00 (2H, d, J=8.1 Hz), 6.91-6.88 (2H, m), 6.85-6.81 (2H, m), 4.57-4.52 (2H, m), 4.44-4.36 (8H, m), 4.19-4.08 (4H, m), 3.89-3.53 (22H, m), 2.45 (6H, s), 2.24-2.17 (2H, m), 2.08-2.02 (2H, m), 1.61-1.37 (8H, m), 0.88 (18H, s); ¹³C NMR (101 MHz, CDCl₃) δ 170.9, 170.0, 165.4, 156.9, 150.4, 148.5, 132.3, 131.7, 130.0, 126.9, 122.0, 119.6, 112.9, 70.7, 70.41, 70.38, 70.2, 69.6, 67.9, 58.9, 58.4, 56.6, 39.2, 37.0, 36.0, 26.3, 17.9, 17.7, 16.2, 13.7. HRMS (ESI) m/z: [M+H]⁺ calculated for: $C_{64}H_{84}N_{10}O_{14}S_2$: 1280.56; observed: 1281.66.

(2S,2'S,4R,4'R)—N,N'-((((3,6,9,12-tetraoxatetradecane-1,14-diyl)bis(oxy))bis(4-(4-methylthiazol-5-yl)-2,1-phenylene))bis(methylene))bis(1-((S)-2-acetamido-3,3-dimethylbutanoyl)-4-hydroxypyrrolidine-2-carboxamide) (CMP106)

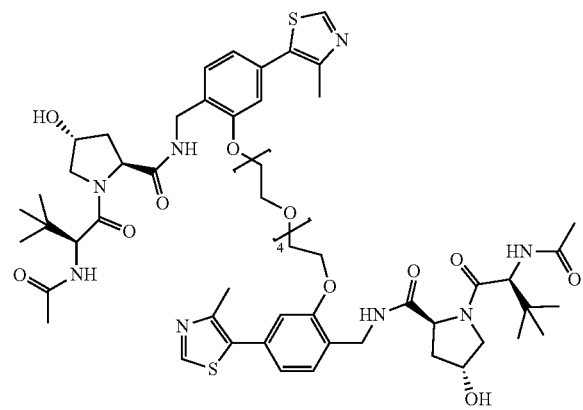

Following general method C, from 17 (24.3 mg, 0.05 mmol, 2 eq.), 19 (11.83 mg, 0.03 mmol, 1.2 eq.) and K₂CO₃ (41.46 mg, 0.3 mmol, 6 eq.), the title compound was obtained as a white solid. Yield: 7.8 mg, 0.006 mmol (26%).

¹H NMR (400 MHz, CDCl₃) δ 8.60 (2H, s), 7.39-7.35 (2H, m), 7.26 (2H, d, J=7.6 Hz), 6.91-6.88 (2H, m), 6.83-6.80 (2H, m), 6.36-6.13 (2H, m), 4.60-4.32 (10H, m), 4.18-4.05 (4H, m), 3.97-3.79 (6H, m), 3.71-3.54 (18H, m), 2.44 (6H, s), 2.17-1.86 (8H, m), 0.87 (18H, s); ¹³C NMR (101 MHz, CDCl₃) δ 171.3, 171.1, 171.0, 170.7, 170.5, 156.8, 156.8, 150.3, 148.5, 132.2, 131.7, 130.0, 129.8, 127.1, 126.9, 122.1, 122.0, 112.8, 112.8, 71.3, 70.7, 70.6, 70.5, 70.5, 70.5, 70.4, 70.2, 70.1, 69.7, 67.9, 58.9, 58.6, 57.6, 57.5, 56.9, 56.7, 42.7, 39.1, 39.0, 37.1, 36.4, 35.4, 35.1, 26.4, 26.4, 23.2, 23.1, 16.2. HRMS (ESI) m/z: [M+H]⁺ calculated for: $C_{58}H_{82}NO_{14}S_2$: 1178.54; observed: 1281.66.

tert-butyl(14-(2-(((2S,4R)-1-((S)-2-(1-cyanocyclopropane-1-carboxamido)-3,3-dimethylbutanoyl)-4-hydroxypyrrolidine-2-carboxamido)methyl)-5-(4-methylthiazol-5-yl)phenoxy)-3,6,9,12-tetraoxatetradecyl) carbonate (22)

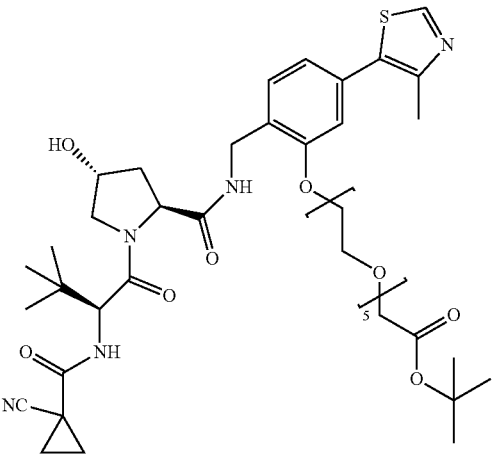

Following general method C, from 18 (27 mg, 0.05 mmol, 1 eq.), 20 (26 mg, 0.06 mmol, 1.2 eq.) and K₂CO₃ (20.73 mg, 0.15 mmol, 3 eq.), the title compound was obtained as a white solid. Yield: 17 mg, 0.02 mmol (33%).

¹H NMR (400 MHz, CDCl₃) δ 8.61 (1H, s), 7.33-7.25 (2H, m), 6.97 (1H, d, J=9.1 Hz), 6.92-6.89 (1H, m), 6.84 (1H, d, J=1.5 Hz), 4.59-4.55 (1H, m), 4.45-4.38 (4H, m), 4.22-4.10 (2H, m), 3.93-3.54 (24H, m), 2.46 (3H, s), 2.32-2.24 (1H, m), 2.10-2.04 (1H, m), 1.63-1.52 (2H, m), 1.45-1.39 (12H, m), 0.87 (9H, s); ¹³C NMR (101 MHz, CDCl₃) δ 170.6, 170.1, 169.7, 165.4, 156.9, 150.3, 148.5, 132.3, 131.7, 130.0, 126.9, 122.0, 119.7, 112.9, 81.7, 70.72, 70.66, 70.5, 70.4, 70.3, 69.6, 69.0, 68.0, 58.8, 58.4, 56.6, 39.3, 36.7, 35.8, 28.1, 26.3, 17.8, 16.2, 13.7. HRMS (ESI) m/z: [M+H]⁺ calculated for: $C_{43}H_{63}N_5O_{12}S$: 873.42; observed: 874.49.

tert-butyl 17-(2-(((2S,4R)-1-((S)-2-acetamido-3,3-dimethylbutanoyl)-4-hydroxypyrrolidine-2-carboxamido)methyl)-5-(4-methylthiazol-5-yl)phenoxy)-3,6,9,12,15-pentaoxaheptadecanoate (21)

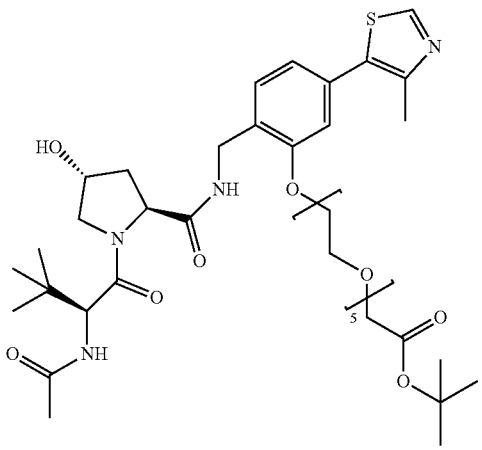

Following general method C, from 17 (24.3 mg, 0.05 mmol, 1 eq.), 20 (26 mg, 0.06 mmol, 1.2 eq.) and K$_2$CO$_3$ (20.73 mg, 0.15 mmol, 3 eq.), the title compound was obtained as a white solid. Yield: 17 mg, 0.021 mmol (33%).

$^1$H NMR (400 MHz, CDCl$_3$) δ, ppm 8.67 (1H, s), 7.32 (2H, d, J=7.8 Hz), 6.95 (1H, dd, J=1.6, 7.6 Hz), 6.88 (1H, d, J=1.8 Hz), 4.65-4.60 (1H, m), 4.53-4.43 (2H, m), 4.39-4.36 (1H, m), 4.24-4.13 (2H, m), 4.00 (2H, d, J=7.0 Hz), 3.92-3.87 (2H, m), 3.77-3.59 (20H, m), 3.08 (2H, s), 2.51 (3H, s), 2.38-2.31 (1H, m), 1.98 (3H, s). $^{13}$C NMR (101 MHz, CDCl$_3$) δ 171.2, 170.8, 170.4, 169.7, 156.8, 150.3, 148.5, 132.2, 131.7, 129.8, 126.9, 122.0, 112.8, 81.6, 70.8, 70.71, 70.69, 70.60, 70.57, 70.55, 70.52, 70.49, 70.47, 70.1, 69.6, 69.3, 69.02, 68.98, 67.9, 58.6, 57.5, 56.7, 39.0, 37.7, 36.5, 35.2, 28.1, 26.4, 23.2, 16.1. HRMS (ESI) m/z: [M+H]$^+$ calculated for: C$_{40}$H$_{62}$N$_4$O$_{12}$S: 822.41; observed: 823.5.

(2S,4R)-1-((S)-2-(tert-butyl)-20-(2-(((2S,4R)-1-((S)-2-(1-cyanocyclopropane-1-carboxamido)-3,3-dimethylbutanoyl)-4-hydroxypyrrolidine-2-carboxamido)methyl)-5-(4-methylthiazol-5-yl)phenoxy)-4-oxo-6,9,12,15,18-pentaoxa-3-azaicosanoyl)-4-hydroxy-N-(4-(4-methylthiazol-5-yl)benzyl)pyrrolidine-2-carboxamide (CMP113)

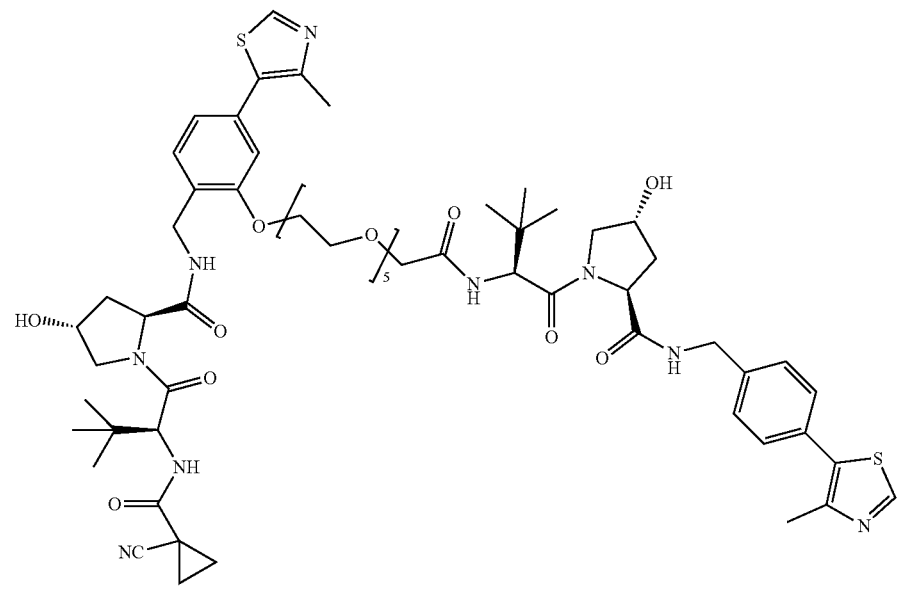

Following general method B, from compound 20 (17 mg, 0.02 mmol, 1 eq.) and trifluoroacetic acid (0.5 ml in 0.5 ml of DCM), the carboxylic acid derivative was obtained as an oil. Yield: 15.7 mg, 0.019 mmol (quantitative). HRMS (ESI) m/z: [M+H]$^+$ calculated for: C$_{39}$H$_{55}$N$_5$O$_{12}$S: 817.36; observed: 818.4.

From the obtained carboxylic acid (15.7 mg, 0.019 mmol, 1 eq.) in 0.5 ml DMF, HATU (7.22 mg, 0.019 mmol, 1 eq.), HOAT (2.58 mg, 0.019 mmol, 1 eq.), compound 7 (8.73 mg, 0.019 mmol, 1 eq.) and DIPEA (3 eq.), the final compound was isolated as white solid. Yield: 6.3 mg, 0.005 mmol (27%).

$^1$H NMR (400 MHz, CDCl$_3$) δ 8.61 (2H, s), 7.58-7.54 (1H, m), 7.31-7.25 (5H, m), 7.02 (1H, d, J=9.7 Hz), 6.88-6.85 (1H, m), 6.78 (1H, d, J=1.5 Hz), 4.59-4.56 (2H, m), 4.47-4.25 (6H, m), 4.13-3.52 (20H, m), 2.47-2.42 (6H, m), 2.34-2.27 (1H, m), 2.19-2.03 (5H, m), 1.63-1.52 (2H, m), 1.48-1.37 (2H, m), 0.90 (18H, s); $^{13}$C NMR (101 MHz, CDCl$_3$) δ 171.2, 171.1, 170.7, 170.3, 165.4, 156.6, 150.3, 148.4, 148.3, 138.3, 132.0, 131.8, 131.7, 130.7, 129.5, 129.4, 127.9, 126.9, 122.0, 119.7, 112.6, 71.0, 70.7, 70.5, 70.4, 70.32, 70.28, 70.25, 69.6, 67.9, 59.1, 58.8, 58.5, 57.3, 57.1, 56.7, 43.1, 39.0, 37.3, 36.8, 36.2, 35.4, 26.4, 26.3, 17.9, 17.7, 16.1, 16.0, 13.7. HRMS (ESI) m/z: [M+H]$^+$ calculated for: C$_{61}$H$_{83}$N$_9$O$_{14}$S$_2$: 1229.55; observed: 1230.66.

(2S,4R)-1-((S)-2-acetamido-3,3-dimethylbutanoyl)-4-hydroxy-N-(2-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)-4-(4-methylthiazol-5-yl)benzyl)pyrrolidine-2-carboxamide (CMP112)

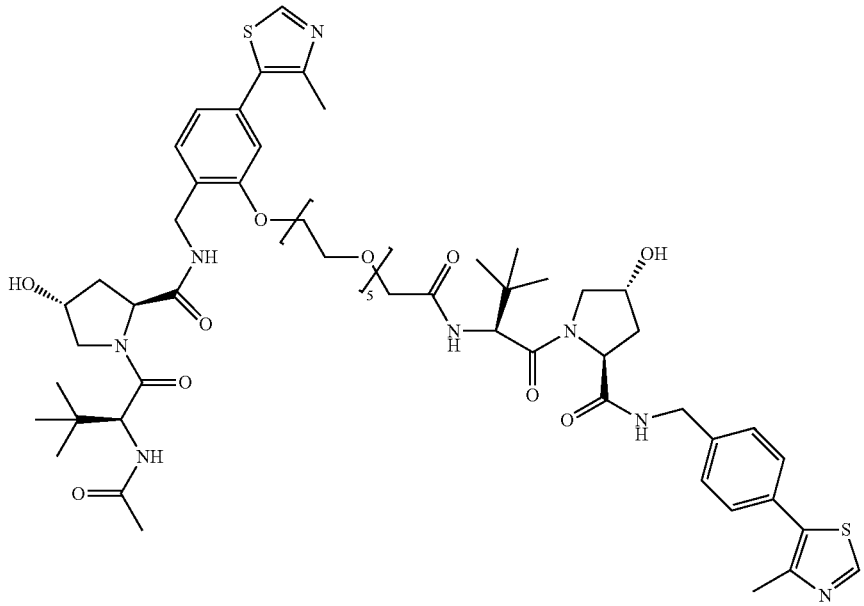

Following general method B, from compound 20 (17 mg, 0.021 mmol, 1 eq.) and trifluoroacetic acid (0.5 ml in 0.5 ml of DCM), the carboxylic acid derivative or 38 was obtained as an oil. Yield: 13 mg, 0.017 mmol (quantitative). HRMS (ESI) m/z: [M+H]$^+$ calculated for: $C_{36}H_{54}N_4O_{12}S$: 766.35; observed: 767.4.

From the carboxylic acid (13 mg, 0.017 mmol, 1 eq.) in 0.5 ml DMF, HATU (6.49 mg, 0.017 mmol, 1 eq.), HOAT (2.31 mg, 0.017 mmol, 1 eq.), compound 7 (7.90 mg, 0.017 mmol, 1 eq.) and DIPEA (3 eq.) the titled compound was obtained as a white solid. Yield: 6 mg, 0.005 mmol (30%).

$^1$H NMR (400 MHz, CDCl$_3$) δ 8.61 (2H, s), 7.49-7.45 (1H, m), 7.32-7.24 (6H, m), 6.90-6.87 (1H, m), 6.79 (1H, d, J=2.4 Hz), 6.24 (1H, d, J=8.9 Hz), 4.61-4.29 (10H, m), 4.11-3.52 (27H, m), 2.44 (6H, s), 2.30 (1H, t, J=13.3 Hz), 2.18-2.03 (3H, m), 0.87 (9H, s); $^{13}$C NMR (101 MHz, CDCl$_3$) δ 171.2, 171.1, 170.7, 170.4, 156.7, 150.3, 148.4, 138.3, 132.2, 130.9, 129.7, 129.4, 128.0, 127.0, 122.0, 112.8, 70.9, 70.6, 70.5, 70.4, 70.3, 70.2, 69.6, 67.9, 59.0, 58.8, 57.7, 57.1, 43.1, 39.0, 37.1, 36.8, 35.6, 35.5, 26.42, 26.38, 23.0, 16.13, 16.06. HRMS (ESI) m/z: [M+H]$^+$ calculated for: $C_{58}H_{82}N_8O_{14}S_2$: 1178.54; observed: 1179.6.

General Method D:

To a solution of the diol (1 eq.) in DCM, tert-butyl bromoacetate (8 eq.), TBABr (1.1 eq.) and 37% w/w aqueous NaOH were added. The reaction mixture was vigorously stirred at r.t. overnight. The organic phase was separated from the aqueous layer and then the aqueous phase was extracted with DCM (×3). Organic layers were collected, dried over MgSO$_4$ and evaporated under reduced pressure. The crude was purified by flash chromatography eluting with ethyl acetate from 10% to 50% v/v in heptane.

General Method E:

A solution of the benzylated starting material in absolute EtOH (0.05 M) was flown in an H-cube machine at a rate of 1 mL/min, H$_2$ 10 atm, 70° C. Solvent was evaporated under reduced pressure to yield the final compound.

General Method F:

To a solution of the dicarboxylic acid linker (1 eq.) in dry DMF, COMU (2 eq.) and DIPEA (5 eq.) were added. The solution was stirred for 10 min and then it was added to a suspension of the VHL-ligand amine 7 (2.1 eq.) and DIPEA (5 eq.) in dry DMF. The mixture was stirred at r.t. until no presence of the starting material was detected by LC-MS. Ice was added and the volatiles were evaporated under reduced pressure to give the crude which was purified by HPLC using a gradient of 20% to 70% v/v acetonitrile in 0.1% v/v aqueous solution of formic acid to yield the final compound.

4,4'-(Butane-1,4-diylbis(oxy))bis(butan-1-ol) (101)

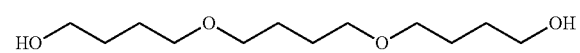 [SMILES: OCCCCOCCCCOCCCCO]

Compound 101 was prepared as reported[40] by Knuf et al. Analytical data matched those previously reported.

Di-tert-butyl 3,8,13,18-tetraoxaicosanedioate (102)

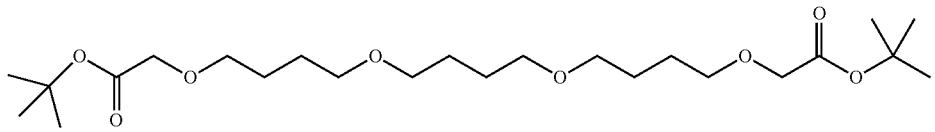 [SMILES: CC(C)(C)OC(=O)COCCCCOCCCCOCCCCOCC(=O)OC(C)(C)C]

Prepared following the general method D from compound 101 (198 mg, 0.8449 mmol) in 37% w/w aqueous NaOH (4 mL) and DCM (4 mL). Compound 102 was obtained as an oil (158 mg, yield: 40%).

$^1$H-NMR (400 MHz, CDCl$_3$) δ: 3.87 (4H, s), 3.45 (4H, t, J=6.1 Hz), 3.38-3.30 (8H, m), 1.67-1.51 (12H, m), 1.41 (18H, s).

3,8,13,18-Tetraoxaicosanedioic acid (103)

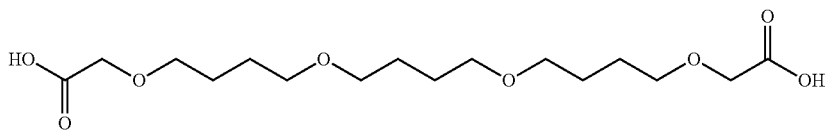 [SMILES: O=C(O)COCCCCOCCCCOCCCCOCC(=O)O]

Prepared following the general method B starting from compound 102 (158 mg, 0.3415 mmol) in TFA/DCM 1:1 (2 mL). Compound 103 was obtained as an oil (120 mg, yield: quantitative).

$^1$H-NMR (400 MHz, CDCl$_3$) δ: 8.26 (s, 2H), 4.09 (s, 4H), 3.58 (t, J=6.1 Hz, 4H), 3.48-3.41 (m, 8H), 1.75-1.60 (m, 12H). $^{13}$C-NMR (101 MHz, CDCl$_3$) δ: 173.1, 71.7, 70.6, 70.4, 67.9, 26.4, 26.3, 26.1.

5-(Benzyloxy)pentan-1-ol (104)

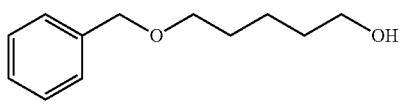 [SMILES: OCCCCCOCc1ccccc1]

1,5-Pentandiol (3.430 g, 3.45 mL, 0.033 mol, 4 eq.) was added dropwise to a suspension of NaH (670 mg, 0,016 mol, 2 eq) in DMF (14 mL) at 0° C. A catalytic amount of NaI was added, followed by benzylbromide (1.360 g, 0.95 mL, 0.008 mol, 1 eq.). The mixture was stirred at r.t. overnight.

The reaction was quenched with NH$_4$Cl aq. sat. and then extracted with ethyl acetate (×3). Organic layers were collected and evaporated under reduced pressure. The crude was purified by flash chromatography eluting from 40% to 90% of ethyl acetate in heptane to give the desired product (1.08 g, yield: 70%).

Analytical data matched those previously reported.[41]

2-(2-(2-(Benzyloxy)ethoxy)ethoxy)ethyl methanesulfonate (105)

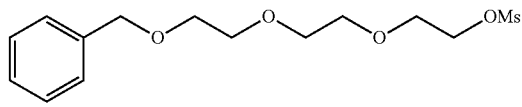 [SMILES: CS(=O)(=O)OCCOCCOCCOCc1ccccc1]

Compound 105 was obtained following the method previously reported[42] Analytical data matched those reported.

1,18-Diphenyl-2,5,8,11,17-pentaoxaoctadecane (106)

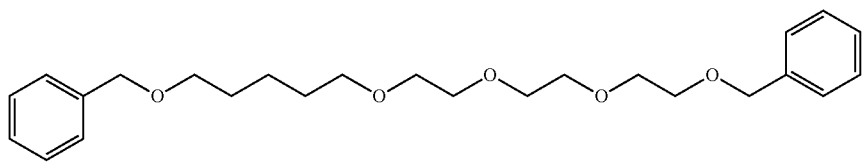 [SMILES: c1ccc(COCCCCCOCCOCCOCCOCc2ccccc2)cc1]

Compound 104 (228.58 mg, 1.177 mmol, 25 eq) was added to a solution of NaHMDS 1M in THF (107.95 mg, 0.588 mL, 0.588 mmol, 1.25 eq.) at 0° C. under $N_2$ atmosphere. Reaction mixture was stirred at r.t. for 1 h. After this time a solution of compound 105 (150.00 mg, 0.471 mmol, 1 eq.) in DMF was added and the mixture was irradiated with microwave at 130° C. for 2 h.

After this time the solvent was evaporated, the reaction quenched with 5% aqueous $NaHSO_4$ and extracted with DCM (x3). Organic layers were collected, dried over $MgSO_4$, filtered and evaporated under reduced pressure. The crude was purified by flash chromatography eluting from 0% to 50% v/v of ethyl acetate in heptane to yield the desired compound 106 as an oil (114 mg, yield: 58%).

$^1$H-NMR (500 MHz, $CDCl_3$) δ: 7.28-7.19 (m, 10H), 4.49 (s, 2H), 4.43 (s, 2H), 3.62-3.54 (m, 10H), 3.51-3.48 (m, 2H), 3.43-3.36 (m, 4H), 1.61-1.48 (m, 4H), 1.42-1.31 (m, 2H).

Di-tert-butyl 3,6,9,12,18-pentaoxaicosanedioate (107)

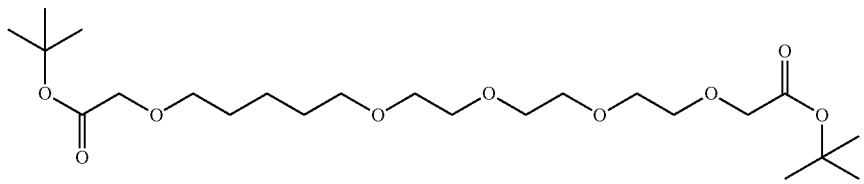 [SMILES: CC(C)(C)OC(=O)COCCCCCOCCOCCOCCOCC(=O)OC(C)(C)C]

Starting from compound 106 (265 mg, 0.610 mmol) and following the general method E the deprotected compound was obtained as an oil (131 mg) and used without any further purification for the next step.

Following the general method D from the deprotected compound (131 mg, 0.5544 mmol) in 37% w/w aqueous NaOH (2.2 mL) and DCM (2.2 mL) compound 107 was obtained as an oil (122 mg, yield: 47%).

$^1$H-NMR (500 MHz, $CDCl_3$) δ: 4.00 (s, 2H), 3.92 (s, 2H), 3.69-3.60 (m, 10H), 3.57-3.53 (m, 2H), 3.52-3.46 (m, 2H), 3.43 (t, J=7.1 Hz, 2H), 1.67-1.56 (m, 4H), 1.46 (d, J=0.6 Hz, 18H), 1.43-1.37 (m, 2H). $^{13}$C-NMR (101 MHz, $CDCl_3$) δ: 169.8, 81.5, 81.4, 71.6, 71.3, 70.7, 70.6, 70.1, 69.0, 68.8, 29.5, 29.4, 28.1, 22.6.

3,6,9,12,18-Pentaoxaicosanedioic acid (108)

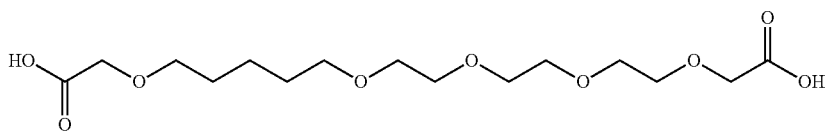 [SMILES: O=C(O)COCCCCCOCCOCCOCCOCC(=O)O]

Prepared following the general method B starting from compound 107 (90 mg, 0.1937 mmol) in 2 mL of TFA/DCM 1:1. Compound 108 was obtained as an oil (66 mg, yield: quantitative).

$^1$H-NMR (400 MHz, $CDCl_3$) δ: 8.15 (s, 2H), 4.11 (s, 2H), 4.02 (s, 2H), 3.71-3.40 (m, 16H), 1.65-1.52 (m, 4H), 1.43-1.34 (m, 2H)

1,5-Bis(allyloxy)pentane (109)

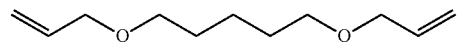

Compound 109 was obtained starting from 1,5-petandiol (500 mg, 4.8 mmol) and following the method reported.[43]

Analytical data matched those previously reported.

3,3'-(Pentane-1,5-diylbis(oxy))bis(propan-1-ol)(110)

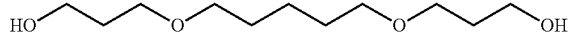 [SMILES: OCCCOCCCCCOCCCO]

A solution of compound 109 (500 mg, 2.71 mmol, 1 eq.) in dry THF (4.2 mL) was added dropwise to a solution 0.5 M of 9-Borabicyclo[3.3.1]nonane in THF (993 mg, 16.28 mL, 8.14 mmol, 3 eq.) at 0° C. and the resulting solution was stirred at r.t. overnight.

The reaction was quenched by MeOH (3.17 mL), 30% w/w aq. NaOH (6.35 mL), 30% v/v aq. $H_2O_2$ (6.35 mL) and the mixture was left to stir for 2 h. Then it was extracted with ethyl acetate (x3). Organic layers were collected, washed with brine, dried over $MgSO_4$ and evaporated under reduced pressure. The crude was purified by flash chromatography eluting from 0% to 100% ethyl acetate in heptane to yield the desired product as an oil (483 mg, yield: 81%). Analytical data matched those previously reported.[43]

Di-tert-butyl 3,7,13,17-tetraoxanonadecanedioate (111)

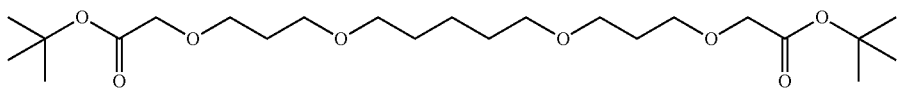 [SMILES: CC(C)(C)OC(=O)COCCCOCCCCCOCCCOCC(=O)OC(C)(C)C]

Compound 111 was obtained from compound 110 (214 mg, 0.9714 mmol) following the general method D, in 37% w/w aqueous NaOH (4 mL) and DCM (4 mL). The desired product was obtained as an oil (65 mg, yield: 15%).

$^1$H-NMR (400 MHz, CDCl$_3$) δ: 3.88 (s, 4H), 3.53 (t, J=6.5 Hz, 4H), 3.44 (t, J=6.4 Hz, 4H), 3.34 (t, J=6.9 Hz, 4H), 1.85-1.78 (m, 4H), 1.55-1.47 (m, 4H), 1.41 (s, 18H), 1.36-1.29 (m, 2H).

3,7,13,17-Tetraoxanonadecanedioic acid (112)

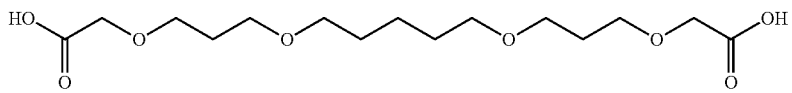 [SMILES: O=C(O)COCCCOCCCCCOCCCOCC(=O)O]

Prepared following the general method B starting from compound 111 (64 mg, 0.1427 mmol) in TFA/DCM 1:1 (2 mL). Compound 112 was obtained as an oil (47.5 mg, yield: quantitative).

$^1$H-NMR (400 MHz, CDCl$_3$) δ: 8.11 (s, 2H), 4.06 (s, 4H), 3.64 (t, J=5.9 Hz, 4H), 3.54 (t, J=5.9 Hz, 4H), 3.42 (t, J=6.4 Hz, 4H), 1.88-1.81 (m, 4H), 1.60-1.52 (m, 4H), 1.36 (dt, J=7.6, 11.9 Hz, 2H). $^{13}$C-NMR (101 MHz, CDCl$_3$) δ: 173.3, 71.1, 69.6, 68.2, 67.9, 29.4, 29.2, 22.7.

5-(Benzyloxy)pentyl 4-methylbenzenesulfonate (113)

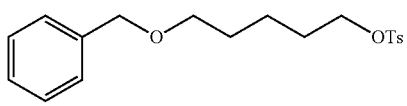 [SMILES: Cc1ccc(S(=O)(=O)OCCCCCOCc2ccccc2)cc1]

To a solution of compound 104 (1.910 g, 9.8387 mmol, 1 eq.) and triethylamine (1.65 mL, 11.8226 mmol, 1.2 eq.) in DCM (15 mL) a solution of p-TsCl (2.063 g, 10.8226 mmol, 1.1 eq.) in DCM (15 mL) was added at 0° C. The mixture was left to stir overnight. Then NaHCO$_3$ aq. sat. was added. The aqueous phase was separated from the organic layer and it was extracted with DCM (×2). Organic layers were collected and washed with 5% aqueous HCl solution. The crude was purified by flash chromatography eluting from 0% to 60% v/v ethyl acetate in heptane to yield the desired product (1.9 g, yield: 55%). Analytical data matched those previously reported.[44]

1,18-Diphenyl-2,8,11,17-tetraoxaoctadecane (114)

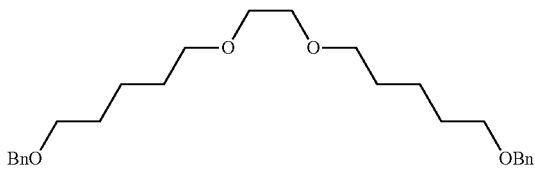

A mixture of compound 113 (1.9 g, 5.6863 mmol, 2.4 eq.), ethylenglycol (147 mg, 2.3696 mmol, 1 eq.) and TBA bisulphate (804 mg, 2.3693 mmol, 1 eq) was dissolved in toluene (8 mL) and NaOH aq. 50% (6 mL). The mixture was vigorously stirred overnight. The organic phase was separated from the aqueous layer and then it was extracted with ethyl acetate (×3). Organic layers were collected, dried over MgSO$_4$ and evaporated under reduced pressure. The crude was purified by flash chromatography eluting with a mixture v/v of ethyl acetate in heptane, from 100% heptane to 100% ethyl acetate. The desired compound was obtained as an oil (200 mg, yield: 8.5%).

$^1$H-NMR (500 MHz, CDCl$_3$) δ: 7.25-7.22 (m, 10H), 4.40 (s, 4H), 3.47 (s, 4H), 3.39-3.35 (m, 8H), 1.58-1.47 (m, 8H), 1.37-1.29 (m, 4H).

5,5'-(Ethane-1,2-diylbis(oxy))bis(pentan-1-ol) (115)

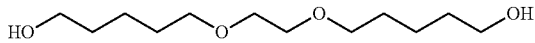 [SMILES: OCCCCCOCCOCCCCCO]

Starting from compound 114 (200 mg, 0.8535 mmol) and following the general method E compound 115 was obtained as an oil (35 mg, yield: 31%).

¹H-NMR (400 MHz, CDCl₃) δ: 3.53 (t, J=6.1 Hz, 4H), 3.49 (s, 4H), 3.49 (s, 4H), 3.40 (t, J=6.6 Hz, 4H), 2.93 (s, 2H), 1.58-1.45 (m, 8H), 1.37-1.29 (m, 4H).

1,2-Di(1,3-dioxan-2-y)ethane (118)

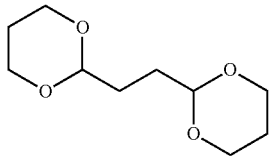 [SMILES: C1COC(CCC2OCCCO2)OC1]

Compound 118 was prepared in accordance with the published procedure,[45] starting from 2,5-dimethoxytetrahydrofuran (10.0 g, 75.6659 mmol). Analytical data matched those previously reported.

3,3'-(Butane-1,4-diylbis(oxy))bis(propan-1-ol) (119)

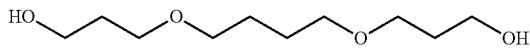 [SMILES: OCCCOCCCCOCCCO]

Compound 119 was prepared accordingly in accordance with the published procedure,[45] starting from compound 118. Analytical data matched those previously reported.

1-Phenyl-2,5,9,14-tetraoxaheptadecan-17-ol (120)

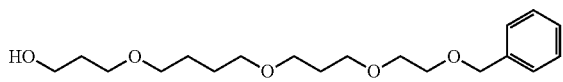 [SMILES: OCCCOCCCCOCCCOCCOCc1ccccc1]

Compound 120 (1.1 g, 5.3325 mmol, 3 eq.) was dissolved in toluene (10 mL) and NaOH aq. 50% w/w (5 mL). TBABr (590 mg, 1.7775 mmol, 1 eq.), a catalytic amount of TBAI and benzyl-2-bromoethyl ether (382 mg, 1.7775 mmol, 1 eq.) were added and the reaction mixture was vigorously stirred for 48 h. Organic layer was separated from the aqueous phase and the aqueous phase was extracted with DCM (×3). The crude was purified by flash chromatography eluting from 0% to 5% v/v MeOH in DCM to obtain the product as an oil (350 mg, 57%).

¹H-NMR (400 MHz, CDCl₃) δ: 7.33-7.22 (m, 5H), 4.55 (s, 2H), 3.74 (dd, J=5.7, 11.2 Hz, 2H), 3.59-3.55 (m, 6H), 3.53 (t, J=6.5 Hz, 2H), 3.47 (t, J=6.4 Hz, 2H), 3.44-3.37 (m, 4H), 2.44 (t, J=5.7 Hz, 1H), 1.87-1.76 (m, 4H), 1.61-1.57 (m, 4H).

3-(4-(3-(2-Hydroxyethoxy)propoxy)butoxy)propan-1-ol (121)

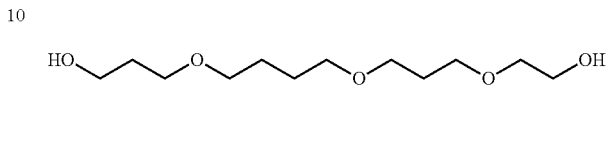

The product was obtained starting from compound 120 (350 mg, 1.028 mmol) and following the general method E. The conversion was not quantitative so the product 121 was separated from the starting material by a flash chromatography eluting from 100% DCM to 9:1 v/v DCM/MEOH (87 mg, yield: 34%).

¹H-NMR (400 MHz, CDCl₃) δ: 3.66-3.60 (m, 4H), 3.51-3.38 (m, 8H), 3.38-3.31 (m, 4H), 1.79-1.69 (m, 4H), 1.57-1.50 (m, 4H).

Di-tert-butyl 3,6,10,15,19-pentaoxahenicosanedioate (122)

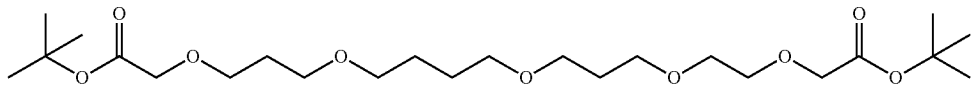 [SMILES: CC(C)(C)OC(=O)COCCCOCCCCOCCCOCCOCC(=O)OC(C)(C)C]

Compound 122 was obtained from compound 121 (87 mg, 0,3475 mmol) following the general method D, in 37% w/w aqueous NaOH (1.5 mL) and DCM (1.5 mL). The desired product was obtained as an oil (47 mg, yield: 28%).

¹H-NMR (400 MHz, CDCl₃) δ: 3.99 (s, 2H), 3.68-3.42 (m, 12H), 3.41-3.36 (m, 4H), 1.88-1.77 (m, 4H), 1.59-1.55 (m, 4H), 1.44 (s, 18H).

3,6,10,15,19-Pentaoxahenicosanedioic acid (123)

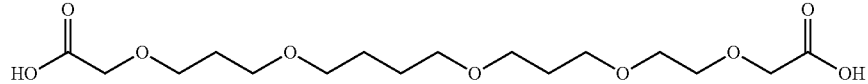 [SMILES: O=C(O)COCCCOCCCCOCCCOCCOCC(=O)O]

Prepared following the general method B starting from compound 122 (47 mg, 0.0983 mmol) in TFA/DCM 1:1 (1 mL). Compound 123 was obtained as an oil (35 mg, yield: quantitative).

¹H-NMR (500 MHz, CDCl3) δ: 4.14 (s, 2H), 4.07 (s, 2H), 3.73-3.69 (m, 2H), 3.65-3.59 (m, 4H), 3.59-3.53 (m, 4H), 3.49 (t, J=6.3 Hz, 2H), 3.47-3.40 (m, 4H), 1.89-1.81 (m, 4H), 1.62-1.57 (m, 4H).

13C-NMR (101 MHz, CDCl3) δ: 173.9, 173.7, 71.3, 71.0, 70.8, 70.0, 69.6, 68.7, 68.6, 68.1, 68.0, 67.6, 29.7, 29.5, 26.3, 26.2.

N1,N20-Bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,18-pentaoxaicosanediamide (124)

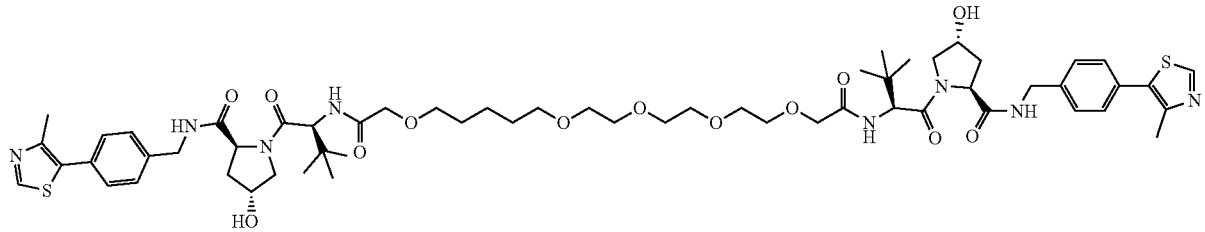 [SMILES: Cc1ncsc1-c1ccc(CNC(=O)[C@@H]2C[C@@H](O)CN2C(=O)[C@@H](NC(=O)COCCCCCOCCOCCOCCOCC(=O)N[C@H](C(=O)N2C[C@H](O)C[C@H]2C(=O)NCc2ccc(-c3scnc3C)cc2)C(C)(C)C)C(C)(C)C)cc1]

Compound 124 was prepared accordingly to general method F, starting from compound 7 (20 mg, 0.0428 mmol) and compound 108 (7.2 mg, 0.02038 mmol). 5 mg were obtained (yield: 21%).

$^1$H-NMR (500 MHz, MeOD) δ: 8.77 (s, 2H), 7.34 (dd, J=7.4, 23.2 Hz, 8H), 4.59 (dd, J=2.4, 9.4 Hz, 2H), 4.50-4.38 (m, 6H), 4.27 (t, J=4.3 Hz, 1H), 4.24 (t, J=4.3 Hz, 1H), 3.94 (dd, J=15.3, 22.3 Hz, 2H), 3.85 (dd, J=15.3, 24.4 Hz, 2H), 3.76 (d, J=10.7 Hz, 2H), 3.72-3.68 (m, 2H), 3.61-3.40 (m, 14H), 3.35 (dt, J=1.0, 6.5 Hz, 2H), 2.37 (s, 6H), 2.16-2.09 (m, 2H), 2.02-1.96 (m, 2H), 1.57-1.45 (m, 4H), 1.39-1.32 (m, 2H), 0.94 (s, 18H).

$^{13}$C-NMR (101 MHz, MeOD) δ: 174.4, 174.3, 172.1, 172.0, 171.7, 152.9, 149.0, 140.3, 133.4, 131.5, 130.5, 130.4, 129.5, 129.0, 72.9, 72.3, 72.2, 71.7, 71.6, 71.5, 71.2, 71.1, 70.7, 60.8, 58.1, 58.0, 43.7, 38.9, 37.2, 37.1, 30.5, 30.4, 27.0, 26.9, 23.8, 15.8.

HRMS: found 1177.6435 [M+H$^+$].

N1,N20-Bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,8,13,18-tetraoxaicosanediamide (125)

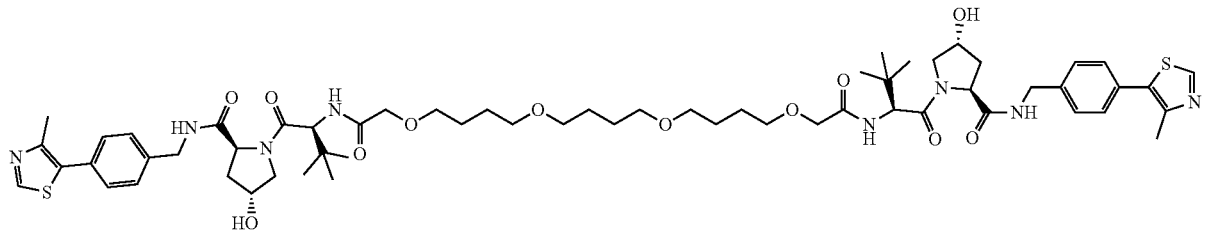 [SMILES: Cc1ncsc1-c1ccc(CNC(=O)[C@@H]2C[C@@H](O)CN2C(=O)[C@@H](NC(=O)COCCCCOCCCCOCCCCOCC(=O)N[C@H](C(=O)N2C[C@H](O)C[C@H]2C(=O)NCc2ccc(-c3scnc3C)cc2)C(C)(C)C)C(C)(C)C)cc1]

Compound 125 was prepared accordingly to general method F, starting from compound 7 (20 mg, 0.0428 mmol) and compound 103 (7.1 mg, 0.02038 mmol). 6.7 mg were obtained (yield: 28%).

$^1$H-NMR (500 MHz, MeOD) δ: 8.77 (s, 2H), 7.34 (dd, J=8.3, 23.6 Hz, 8H), 4.59 (d, J=12.0 Hz, 2H), 4.50-4.40 (m, 6H), 4.26 (dd, J=4.9, 15.9 Hz, 2H), 3.86 (dd, J=15.3, 23.4 Hz, 4H), 3.77 (d, J=11.4 Hz, 2H), 3.70 (dd, J=3.9, 11.1 Hz, 2H), 3.46 (t, J=6.0 Hz, 4H), 3.38-3.28 (m, 8H), 2.37 (s, 6H), 2.16-2.10 (m, 2H), 2.02-1.96 (m, 2H), 1.62-1.52 (m, 8H), 1.51-1.45 (m, 4H), 0.93 (s, 18H).

$^{13}$C-NMR (101 MHz, MeOD) δ: 174.3, 172.1, 172.0, 171.7, 152.8, 149.1, 140.3, 133.4, 131.5, 130.5, 130.4, 129.5, 129.0, 72.7, 71.7, 71.5, 71.1, 70.7, 60.8, 58.1, 58.0, 43.7, 39.0, 37.2, 27.6, 27.5, 27.4, 15.9.

HRMS: found 1175.6623 [M+H$^+$].

N1,N19-Bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,7,13,17-tetraoxanonadecanediamide (126)

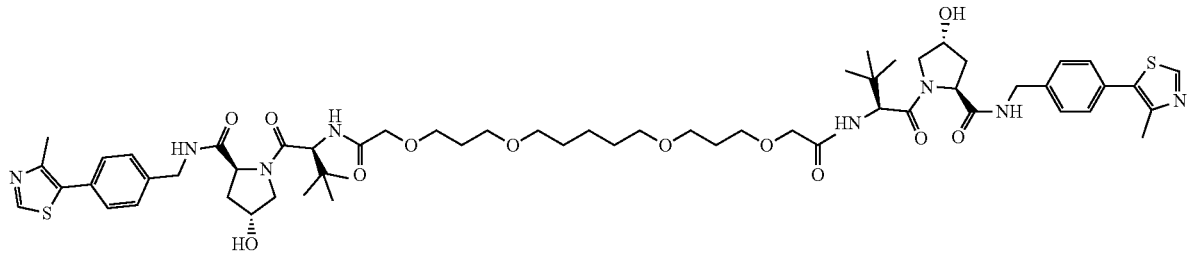 [SMILES: Cc1ncsc1-c1ccc(CNC(=O)[C@@H]2C[C@@H](O)CN2C(=O)[C@@H](NC(=O)COCCCOCCCCCOCCCOCC(=O)N[C@H](C(=O)N2C[C@H](O)C[C@H]2C(=O)NCc2ccc(-c3scnc3C)cc2)C(C)(C)C)C(C)(C)C)cc1]

Compound 126 was prepared accordingly to general method F, starting from compound 7 (20 mg, 0.0428 mmol) and compound 112 (6.8 mg, 0.0204 mmol). 6.6 mg were obtained as a white solid (yield: 28%).

$^1$H-NMR (500 MHz, MeOD) δ: 8.76 (s, 2H), 7.37-7.30 (m, 8H), 4.60 (d, J=9.4 Hz, 2H), 4.50-4.24 (m, 8H), 3.87 (d, J=6.5 Hz, 4H), 3.77 (d, J=11.2 Hz, 2H), 3.70 (dd, J=3.8, 11.5 Hz, 2H), 3.55-3.49 (m, 4H), 3.43 (dt, J=1.2, 6.2 Hz, 4H), 3.33-3.29 (m, 4H), 2.37 (s, 6H), 2.16-2.10 (m, 2H), 2.03-1.96 (m, 2H), 1.80-1.74 (m, 4H), 1.47-1.40 (m, 4H), 1.30-1.23 (m, 2H), 0.93 (s, 18H).

$^{13}$C-NMR (101 MHz, MeOD) δ: 174.3, 171.8, 171.6, 152.8, 149.0, 140.2, 133.4, 131.5, 130.5, 130.3, 129.5, 128.9, 71.9, 71.0, 70.8, 69.8, 68.3, 60.8, 58.1, 57.9, 43.7, 38.9, 37.2, 30.9, 30.5, 26.9, 23.9, 15.8.

HRMS: found 1161.6446 [M+H$^+$].

N1,N21-Bis((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,10,15,19-pentaoxahenicosanediamide (128)

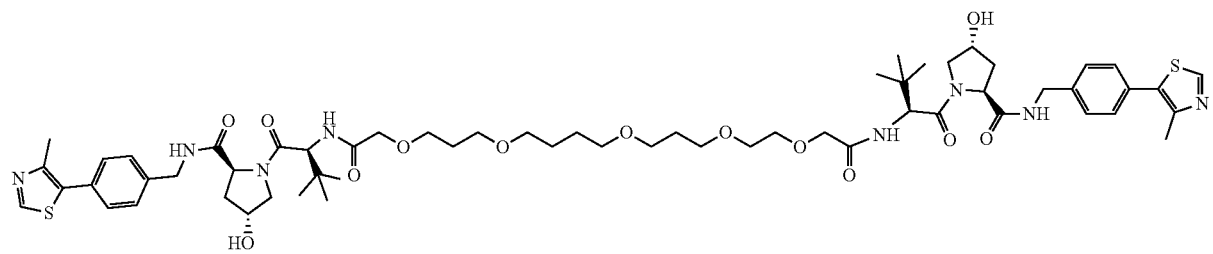 [SMILES: Cc1ncsc1-c1ccc(CNC(=O)[C@@H]2C[C@@H](O)CN2C(=O)[C@@H](NC(=O)COCCCOCCCCOCCCOCCOCC(=O)N[C@H](C(=O)N2C[C@H](O)C[C@H]2C(=O)NCc2ccc(-c3scnc3C)cc2)C(C)(C)C)C(C)(C)C)cc1]

Compound 128 was prepared accordingly to general method F, starting from compound 7 (20 mg, 0.0428 mmol) and compound 123 (7.5 mg, 0.02038 mmol). 6.5 mg were obtained as a white solid (yield: 27%).

$^1$H-NMR (500 MHz, MeOD) δ: 9.00 (d, J=1.1 Hz, 2H), 7.45 (dd, J=8.4, 23.1 Hz, 8H), 4.71-4.68 (m, 2H), 4.55 (tt, J=12.4, 11.9 Hz, 6H), 4.36 (d, J=15.5 Hz, 2H), 4.03 (d, J=3.6 Hz, 2H), 3.97 (d, J=5.9 Hz, 2H), 3.89-3.78 (m, 4H), 3.71-3.68 (m, 2H), 3.64-3.36 (m, 14H), 2.49 (s, 6H), 2.26-2.19 (m, 2H), 2.13-2.06 (m, 2H), 1.90-1.84 (m, 2H), 1.85-1.79 (m, 2H), 1.61-1.55 (m, 4H), 1.04 (d, J=3.4 Hz, 18H).

$^{13}$C-NMR (101 MHz, MeOD) δ: 174.4, 174.3, 172.1, 171.9, 171.8, 171.7, 153.3, 140.6, 131.8, 130.4, 129.0, 72.3, 71.8, 71.2, 71.1, 70.9, 69.9, 69.4, 68.7, 68.4, 60.8, 58.2, 58.1, 58.0, 43.7, 38.9, 37.2, 37.1, 31.1, 31.0, 27.5, 27.0, 15.4.

HRMS: found 1191.6137 [M+H$^+$].

(S)-1-((2R,3R,4S)-3-Fluoro-4-hydroxy-2-((4-(4-methylthiazol-5-yl)benzyl)carbamoyl)pyrrolidin-1-yl)-3,3-dimethyl-1-oxobutan-2-aminium chloride (129)

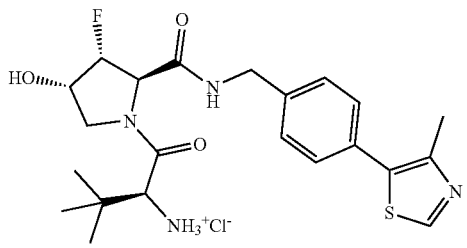

Compound 129 was prepared accordingly to PATENT WO 2018/051107 A1. Analytical data matched those previously reported.

N1,N20-Bis((S)-1-((2R,3R,4S)-3-fluoro-4-hydroxy-2-((4-(4-methylthiazol-5-yl)benzyl)carbamoyl)pyrrolidin-1-yl)-3,3-dimethyl-1-oxobutan-2-yl)-3,6,9,12,15,18-hexaoxaicosanediamide (130)

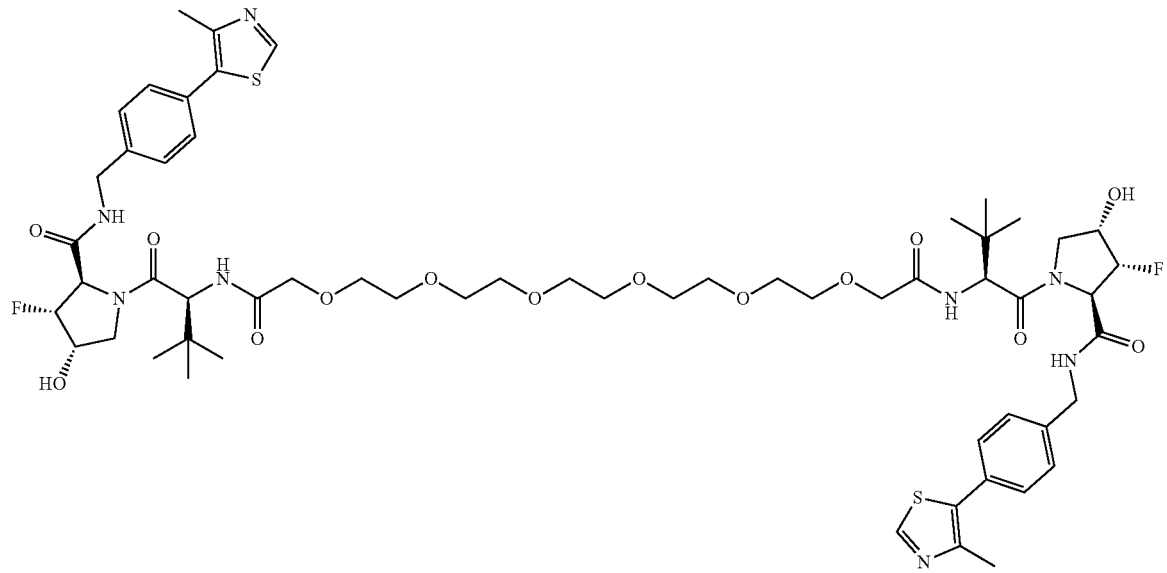 [SMILES: Cc1ncsc1-c1ccc(CNC(=O)[C@@H]2[C@@H](F)[C@@H](O)CN2C(=O)[C@@H](NC(=O)COCCOCCOCCOCCOCCOCC(=O)N[C@H](C(=O)N2C[C@H](O)[C@H](F)[C@H]2C(=O)NCc2ccc(-c3scnc3C)cc2)C(C)(C)C)C(C)(C)C)cc1]

Prepared accordingly to general method F, starting from compound 129 (16.9 mg, 0.0348 mmol) and 3,6,9,12,15,18-hexaoxaicosanedioic acid (6.17 mg, 0.0174 mmol). Obtained 7.5 mg (35% yield) as white solid.

$^1$H-NMR (400 MHz, MeOD) δ: 8.89 (s, 2), 7.46 (d, J=8.7 Hz, 8H), 4.99 (td, J=3.3, 52.9 Hz, 2H), 4.69 (s, 2H), 4.65 (dd, J=2.9, 21.3 Hz, 2H), 4.60-4.34 (m, 6H), 4.08-4.03 (m, 6H), 3.77-3.59 (m, 22H), 2.49 (s, 6H), 1.06 (s, 18H).

$^{19}$F-NMR (376.45 MHz, MeOD): −201.87, $^{13}$C-NMR (101 MHz, MeOD) δ: 170.9, 170.5, 169.2, 169.1, 151.5, 147.7, 138.6, 130.2, 129.0, 127.5, 94.0, 92.1, 70.9, 70.2, 70.1, 70.1, 69.6, 69.5, 64.4, 64.1, 56.1, 50.9, 42.4, 35.3, 25.5, 14.4. HRMS: found 1215.5214 [M+H$^+$].

Abbreviations

BAIB, bis-acetoxy iodobenzene;
CID, chemical inducer of dimerization;
CRL, Cullin RING ligase;
DC50, half-degrading concentration;
DCM, dichloromethane;
DIPEA, N,N-Diisopropyethylamine;
DMF, dimethylformamide;
DMSO, dimethylsulfoxide;
HATU, 1-[Bis(dimethylamino)methylene]-1H-1,2,3Ytriazolo[4,5-b]pyridinium 3-oxid hexafluorophosphate;
Hdy-HIF-1α, hydroxylated form of HIF-1α;
HIF-1α, hypoxia inducible factor alpha;
Hyp, hydroxyproline;
HOAT, 1-Hydroxy-7-azabenzotriazole;
IAPS, inhibitor of apoptosis proteins;
ITC, isothermal titration calorimetry;
LHS, left hand side;
PEG, polyethylene glycol;
PHD, prolyl hydroxylase domain-containing protein;
PPI, protein-protein interaction;
PROTACS, Proteoysis-Targeting Chimeras;
RHS, right end side;
SEC, size exclusion chromatography;
TEMPO, 2,2,6,6-Tetramethylpiperidin-1-yl)oxyl or (2,2,6,6-tetramethylpiperidin-1-yl)oxidanyl;
TFA, trifluoroacetic acid;
VHL, von Hippel-Lindau;
HRE, hypoxia response element.

REFERENCES (1) Buckley, D. L.; Van Molle, I.; Gareiss, P. C.; Tae, H. S.; Michel, J.; Noblin, D. J.; Jorgensen, W. L.; Ciulli, A.; Crews, C. M. *J Am Chem Soc* 2012, 134 (10), 4465-4468.

(2) Galdeano, C.; Gadd, M. S.; Soares, P.; Scaffidi, S.; Van Molle, I.; Birced, I.; Hewitt, S.; Dias, D. M.; Ciulli, A. *J Med Chem* 2014, 57 (20), 8657-8663.

(3) Frost, J.; Galdeano, C.; Soares, P.; Gadd, M. S.; Grzes, K. M.; Ellis, L.; Epemolu, O.; Shimamura, S.; Bantscheff, M.; Grandi, P.; Read, K. D.; Cantrell, D. A.; Rocha, S.; Ciulli, A. *Nat Commun* 2016, 7, 13312.
(4) Ito, T.; Ando, H.; Suzuki, T.; Ogura, T.; Hotta, K.; Imamura, Y; Yamaguchi, Y; Handa, H. *Science* 2010, 327 (5971), 1345-1350.
(5) Fischer, E. S.; Böhm, K.; Lydeard, J. R.; Yang, H.; Stadler, M. B.; Cavadini, S.; Nagel, J.; Serluca, F.; Acker, V.; Lingaraju, G. M.; Tichkule, R. B.; Schebesta, M.; Forrester, W. C.; Schirle, M.; Hassiepen, U.; Ottl, J.; Hild, M.; Beckwith, R. E. J.; Harper, J. W.; Jenkins, J. L.; Thomä, N. H. *Nature* 2014, 512 (7512), 49-53.
(6) Chamberlain, P. P.; Lopez-Girona, A.; Miller, K.; Carmel, G.; Pagarigan, B.; Chie-Leon, B.; Rychak, E.; Corral, L. G.; Ren, Y J.; Wang, M.; Riley, M.; Delker, S. L.; Ito, T.; Ando, H.; Mori, T.; Hirano, Y; Handa, H.; Hakoshima, T.; Daniel, T. O.; Cathers, B. E. *Nat Struct Mol Biol* 2014, 21 (9), 803-809.
(7) Lu, G.; Middleton, R. E.; Sun, H.; Naniong, M.; Ott, C. J.; Mitsiades, C. S.; Wong, K.-K.; Bradner, J. E.; Kaelin, W. G. *Science* 2014, 343 (6168), 305-309.
(8) Krönke, J.; Udeshi, N. D.; Narla, A.; Grauman, P.; Hurst, S. N.; McConkey, M.; Svinkina, T.; Heckl, D.; Comer, E.; Li, X.; Ciarlo, C.; Hartman, E.; Munshi, N.; Schenone, M.; Schreiber, S. L.; Carr, S. A.; Ebert, B. L. *Science* 2014, 343 (6168), 301-305.
(9) Petzold, G.; Fischer, E. S.; Thomä, N. H. *Nature* 2016, 532 (7597), 127-130.
(10) Matyskiela, M. E.; Lu, G.; Ito, T.; Pagarigan, B.; Lu, C.-C.; Miller, K.; Fang, W.; Wang, N.-Y; Nguyen, D.; Houston, J.; Carmel, G.; Tran, T.; Riley, M.; Nosaka, L.; Lander, G. C.; Gaidarova, S.; Xu, S.; Ruchelman, A. L.; Handa, H.; Carmichael, J.; Daniel, T. O.; Cathers, B. E.; Lopez-Girona, A.; Chamberlain, P. P. *Nature* 2016, 535 (7611), 252-257.
(11) Toure, M.; Crews, C. M. *Angew Chem Int Ed Engl* 2016, 55 (6), 1966-1973.
(12) Zengerle, M.; Chan, K.-H.; Ciulli, A. *ACS Chem Biol* 2015, 10 (8), 1770-1777.
(13) Bondeson, D. P.; Mares, A.; Smith, I. E. D.; Ko, E.; Campos, S.; Miah, A. H.; Mulholland, K. E.; Routly, N.; Buckley, D. L.; Gustafson, J. L.; Zinn, N.; Grandi, P.; Shimamura, S.; Bergamini, G.; Faelth-Savitski, M.; Bantscheff, M.; Cox, C.; Gordon, D. A.; Willard, R. R.; Flanagan, J. J.; Casillas, L. N.; Votta, B. J.; Besten, den, W.; Famm, K.; Kruidenier, L.; Carter, P. S.; Harling, J. D.; Churcher, I.; Crews, C. M. *Nat Chem Biol* 2015, 11 (8), 611-617.
(14) Raina, K.; Lu, J.; Qian, Y; Altieri, M.; Gordon, D.; Rossi, A. M. K.; Wang, J.; Chen, X.; Dong, H.; Siu, K.; Winkler, J. D.; Crew, A. P.; Crews, C. M.; Coleman, K. G. *P Natl Acad Sci Usa* 2016, 113 (26), 7124-7129.
(15) Gadd, M. S.; Testa, A.; Lucas, X.; Chan, K.-H.; Chen, W.; Lamont, D. J.; Zengerle, M.; Ciulli, A. *Nat Chem Biol* 2017, 7, 263.
(16) Winter, G. E.; Buckley, D. L.; Paulk, J.; Roberts, J. M.; Souza, A.; Dhe-Paganon, S.; Bradner, J. E. *Science* 2015, 348 (6241), 1376-1381.
(17) Lu, J.; Qian, Y; Altieri, M.; Dong, H.; Wang, J.; Raina, K.; Hines, J.; Winkler, J. D.; Crew, A. P.; Coleman, K.; Crews, C. M. *Chem Biol* 2015, 22 (6), 755-763.
(18) Lai, A. C.; Toure, M.; Hellerschmied, D.; Salami, J.; Jaime-Figueroa, S.; Ko, E.; Hines, J.; Crews, C. M. *Angew Chem Int Ed Engl* 2016, 55 (2), 807-810.
(19) Lebraud, H.; Wright, D. J.; Johnson, C. N.; Heightman, T. D. *ACS Cent Sci* 2016, 2 (12), 927-934.
(20) Erb, M. A.; Scott, T. G.; Li, B. E.; Xie, H.; Paulk, J.; Seo, H.-S.; Souza, A.; Roberts, J. M.; Dastjerdi, S.; Buckley, D. L.; Sanjana, N. E.; Shalem, O.; Nabet, B.; Zeid, R.; Offei-Addo, N. K.; Dhe-Paganon, S.; Zhang, F.; Orkin, S. H.; Winter, G. E.; Bradner, J. E. *Nature* 2017, 543 (7644), 270-274.
(21) Itoh, Y; Ishikawa, M.; Naito, M.; Hashimoto, Y *J Am Chem Soc* 2010.
(22) Ohoka, N.; Okuhira, K.; Ito, M.; Nagai, K.; Shibata, N.; Hattori, T.; Ujikawa, O.; Shimokawa, K.; Sano, O.; Koyama, R.; Fujita, H.; Teratani, M.; Matsumoto, H.; Imaeda, Y; Nara, H.; Cho, N.; Naito, M. *J. Biol. Chem.* 2017, 292 (11), 4556-4570.
(23) Provenzano, R. et al. *Clin. J. Am. Soc. Nephrol.* 2016, 11, 982-991.
(24) Macdougall, I. C. *Clin. J. Am. Soc. Nephrol,* 2008. 3, 200-207.
(25) Hill, P. et al. *J. Am. Soc. Nephrol.* 2008, 19, 39-46.
(26) Rey, S. et al. *Proc. Natl Acad. Sci. USA,* 2009, 106, 20399-20404.
(27) Karuppagounder, S. S. & Ratan, R. R. *J. Cereb. Blood Flow Metab.* 2012, 32, 1347-1361.
(28) Eckle, T. et al. *PLoS Biol.* 2013, 11, e1001665.
(29) Robinson, A. et al. *Gastroenterology* 2008, 134, 145-155.
(30) Botusan et al. *Proc Natl Acad Sci USA.* 2008 Dec. 9; 105(49): 19426-19431.
(31) Ruthenborg et al. *Mol Cells.* 2014 Sep. 30; 37(9): 637-643.
(32) Jain, I. H. et al. *Science* 2016, 352, 54-61.
(33) Ramsay & Cantrell *Front. Immunol.,* 2015, 6, 99
(34) Frost, J. et al. *Nat. Commun.* 2016, 7, 13312.
(35) Buckley, D. L.; Raina, K.; Darricarrere, N.; Hines, J.; Gustafson, J. L.; Smith, I. E.; Miah, A. H.; Harling, J. D.; Crews, C. M. *ACS Chem Biol* 2015, 10 (8), 1831-1837.
(36) Loenarz, C.; Mecinović, J.; Chowdhury, R.; McNeill, L. A.; Flashman, E.; Schofield, C. J. *Angew Chem Int Ed Engl* 2009, 48 (10), 1784-1787.
(37) Rapisarda, A.; Uranchimeg, B.; Scudiero, D. A.; Selby, M.; Sausville, E. A.; Shoemaker, R. H.; Melillo, G. *Cancer Res* 2002, 62 (15), 4316-4324.
(38) Arrowsmith, C. H.; Audia, J. E.; Austin, C.; Baell, J.; Bennett, J.; Blagg, J.; Bountra, C.; Brennan, P. E.; Brown, P. J.; Bunnage, M. E.; Buser-Doepner, C.; Campbell, R. M.; Carter, A. J.; Cohen, P.; Copeland, R. A.; Ben Cravatt; Dahlin, J. L.; Dhanak, D.; Edwards, A. M.; Frye, S. V.; Gray, N.; Grimshaw, C. E.; Hepworth, D.; Howe, T.; Huber, K. V. M.; Jin, J.; Knapp, S.; Kotz, J. D.; Kruger, R. G.; Lowe, D.; Mader, M. M.; Marsden, B.; Mueller-Fahrnow, A.; Müller, S.; O'Hagan, R. C.; Overington, J. P.; Owen, D. R.; Rosenberg, S. H.; Roth, B.; Ross, R.; Schapira, M.; Schreiber, S. L.; Shoichet, B.; Sundstrom, M.; Superti-Furga, G.; Taunton, J.; Toledo-Sherman, L.; Walpole, C.; Walters, M. A.; Willson, T. M.; Workman, P.; Young, R. N.; Zuercher, W. J. *Nat Chem Biol* 2015, 11 (8), 536-541.
(39) Wittmann, V., Takayama, S. & Gong, K. W. *J. Org. Chem.* 199863, 5137-5143.
(40) Knuf Erin C.; Jiang, Jian-Kang; Gin, Mary S.—*Journal of Organic Chemistry,* 2003, vol. 68 (23), p. 9166-9169).
(41) Young, Ian S.; Kerr, Michael A.—*Journal of the American Chemical Society,* 2007, vol. 129(5), p. 1465-1469.
(42) Bonnet, Nelly; O'Hagan, David; Haehner, Georg— *Chemical Communications,* 2007, 47, p. 5066-5068.
(43) Accurso, Adrian A.; Delaney, Mac; O'Brien, Jeff; Kim, Hyonny; Iovine, Peter M.; Diaz, David Diaz; Finn— *Chemistry—A European Journal,* 2014, vol. 20(34), p. 10710-10719.

(44) Bouzide, Abderrahim; LeBerre, Nicolas; Sauve, Gilles—*Tetrahedron Letters*, 2001, vol. 42(50), p. 8781-8783.
(45) Crew, Andrew P. et al—*Journal of Medicinal Chemistry*, 2018, vol. 61(2), p. 583-598

The invention claimed is:

1. A compound having the structure:

A-L-B wherein A and B are independently an E3 ubiquitin ligase protein binding ligand compound of formula 1A:

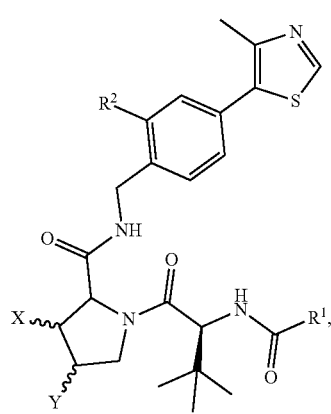

(1A)

wherein L is a linking group which is directly bonded to the compound of formula 1A at $R^1$ or $R^2$ wherein L is $-R^5-[O(CH_2)_m]_n-R^6-$, wherein m and n are independently 0 to 10, and $R^5$ and $R^6$ are independently selected from the group: covalent bond, C1-C10 alkylene, C1-C10 polyether, or —O—;
wherein $R^1$ is selected from either the group: (1) a covalent bond, or C1-C5 alkylene when L is bonded to the compound of formula 1A at $R^1$, or the group (2) H, $NH_2$, C1-C5 alkyl, or $C(CN)C_2H_4$ when L is bonded to the compound of formula 1A at $R^2$;

wherein $R^2$ is selected from the group: a covalent bond, H, $NH_2$, C1-C5 alkyl, $C(CN)C_2H_4$;
wherein X and Y are independently selected from the group: H, OH or halogen; and
wherein $R^7$ is C1-C5 alkylene, or a pharmaceutically acceptable salt, hydrate, solvate or polymorph thereof.

2. A compound according to claim 1, wherein X is H or halogen.

3. A compound according to claim 1, wherein Y is OH.

4. A compound according to claim 1 where either A or B is a compound according to formula 1A, wherein A has the formula 1C:

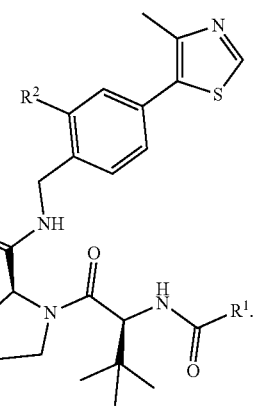

(1C)

5. A compound according to claim 1, wherein L is connected to A via $R^1$ of formula 1A.

6. A compound according to claim 1, wherein L is connected to B via $R^1$ of formula 1A.

7. A compound according to claim 1, wherein $R^5$ is a chemical bond, $R^6$ is a chemical bond, m is 2 and n is 3, 4 or 5.

8. A compound according to claim 7, wherein n is 5.

9. A compound according to claim 1, wherein the compound is of formulae 2, 3 or 4:

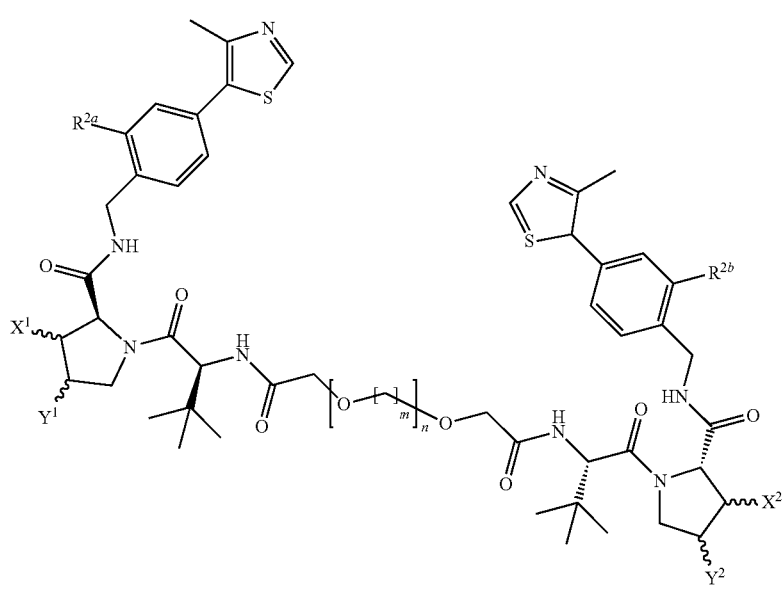

(2)

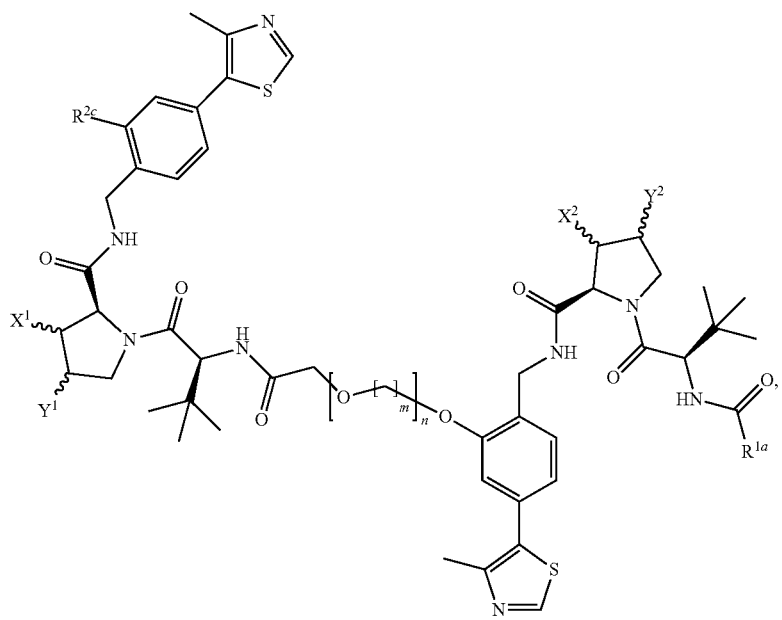

(3)

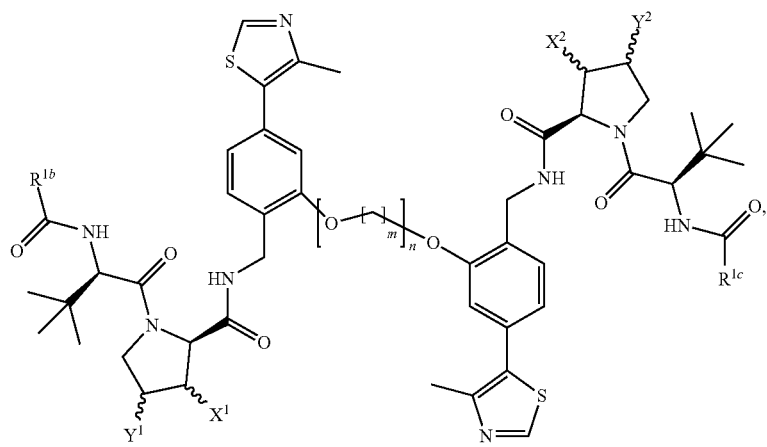

(4)

wherein $R^{2a}$, $R^{2b}$ and $R^{2c}$ are independently selected from H, $NH_2$, C1-C5 alkyl, and $C(CN)C_2H_4$;
$R^{1a}$, $R^{1b}$ and $R^{1c}$ are independently selected from H, $NH_2$, C1-C5 alkyl, and $C(CN)C_2H_4$;
$X^1$ and $X^2$ are independently selected from H, OH, halogen;
$Y^1$ and $Y^2$ are independently selected from H, OH, halogen; and
m and n are independently 0 to 10.

10. A compound according to claim 9, wherein n is 3-5.

11. A compound according to claim 9, wherein m is 1-4.

12. A compound according to claim 1, wherein the linker L is a linear chain of 12-20 atoms in length, optionally wherein the linker chain comprises carbon and/or oxygen atoms, further optionally wherein the linker chain comprises alkylene groups and/or ether groups and/or polyether groups.

13. A compound according to claim 1 selected from the following group:
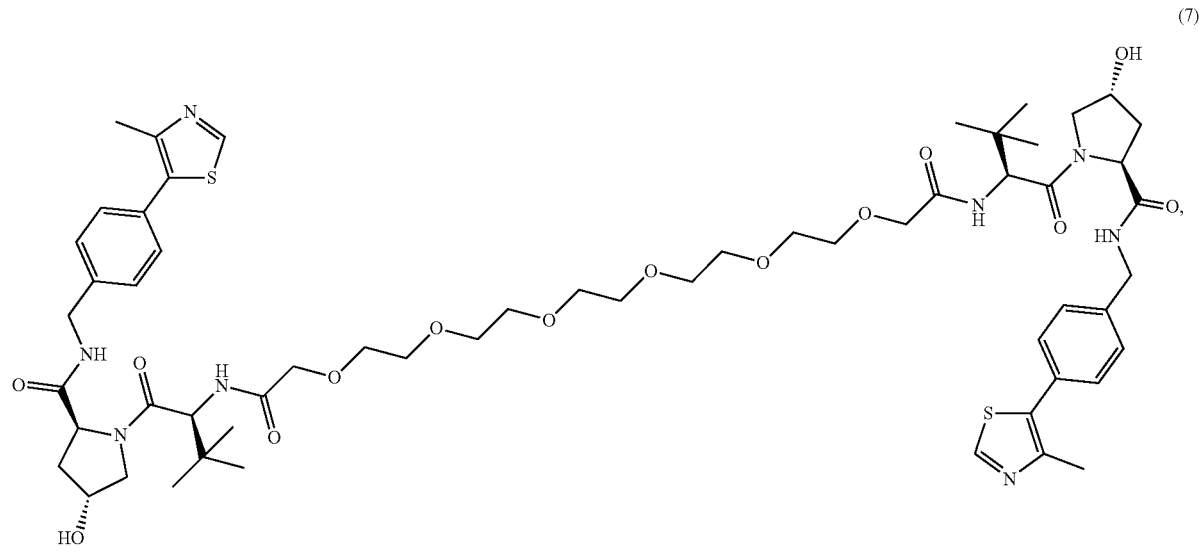 [SMILES: Cc1ncsc1-c1ccc(CNC(=O)[C@@H]2C[C@@H](O)CN2C(=O)[C@@H](NC(=O)COCCOCCOCCOCCOCCOCC(=O)N[C@H](C(=O)N2C[C@H](O)C[C@H]2C(=O)NCc2ccc(-c3scnc3C)cc2)C(C)(C)C)C(C)(C)C)cc1]
(7)
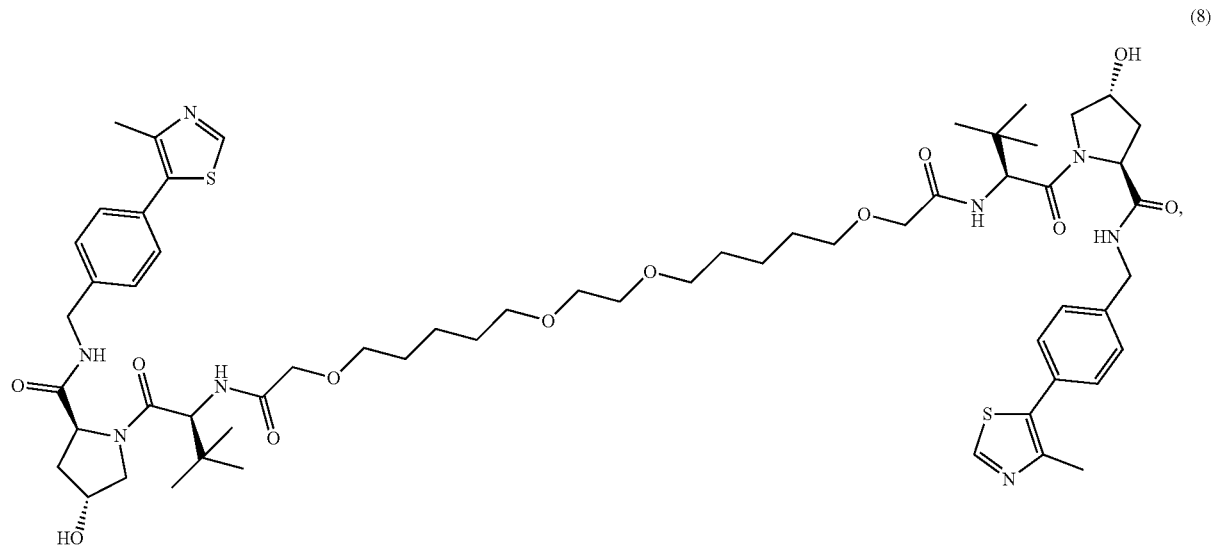
(8)
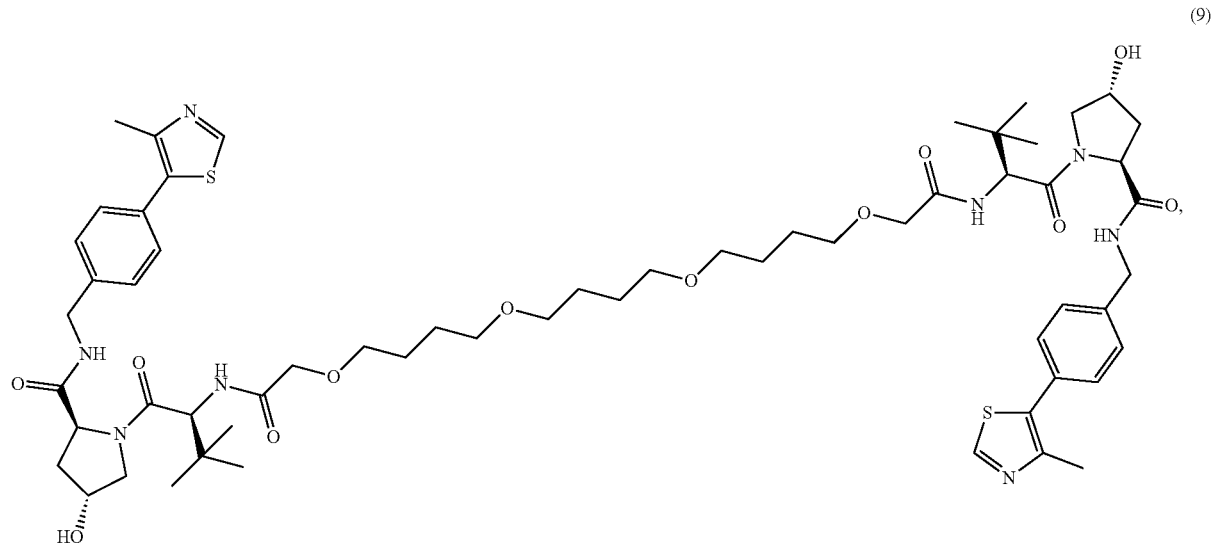
(9)

-continued
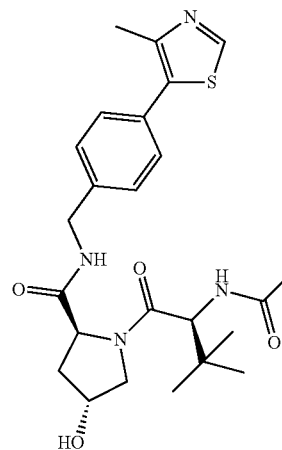
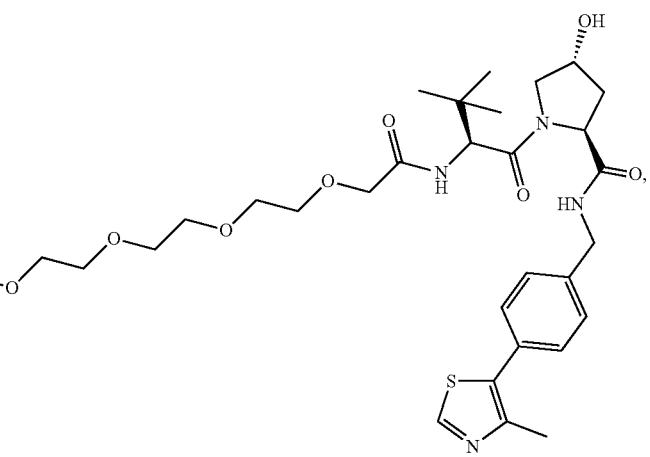
(10)
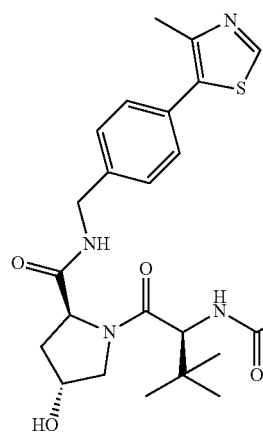
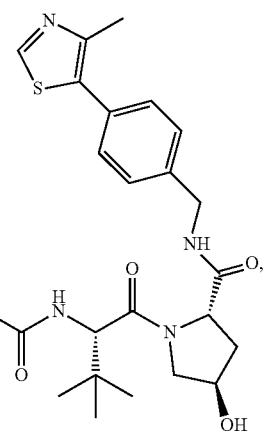
(11)
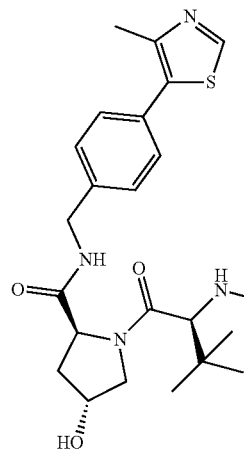
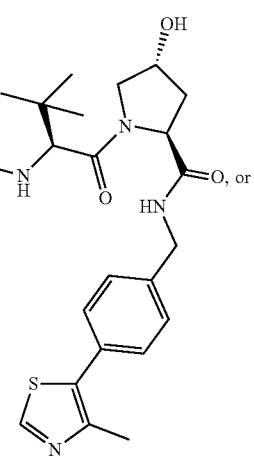
(12)

(13)

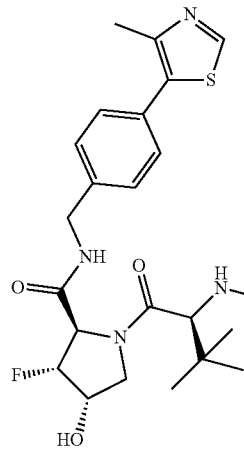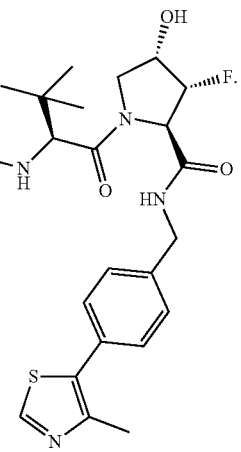

14. A compound according to claim 13, wherein the compound is compound (5) having a structure of:

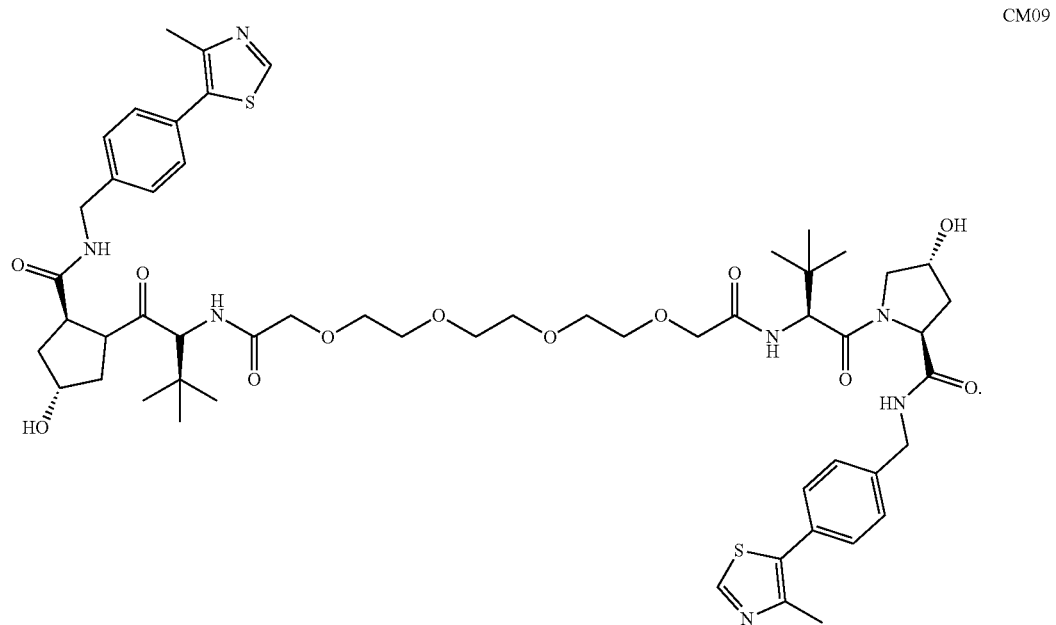

CM09

15. A pharmaceutical composition comprising one or more compounds according to claim 1 and a pharmaceutically acceptable vehicle or diluent therefor.

16. A method of treating at least one selected from the group of anaemia due to chronic kidney disease, anaemia due to cancer chemotherapy, ischemia, an ischemic reperfusion injury, myocardial infarction, stroke, an acute lung injury, intestinal inflammation, a wound, a post-transplantation complication, a mitochondrial respiratory chain dysfunction, and an oncological conditions treatable by enhancing T-cell responses in a subject, wherein the method comprises:

administering to the subject the compound of claim 1, thereby treating the at least one selected from the group of anaemia due to chronic kidney disease, anaemia due to cancer chemotherapy, ischemia, the ischemic reperfusion injury, myocardial infarction, stroke, the acute lung injury, intestinal inflammation, the wound, the post-transplantation complication, the mitochondrial respiratory chain dysfunction, and the oncological condition treatable by enhancing T-cell responses in the subject.

17. A method of regulating activity of a target protein in a subject comprising administering to said subject an effective amount of a compound according to claim 1, wherein the target protein is an E3 ubiquitin ligase protein.

* * * * *

UNITED STATES PATENT AND TRADEMARK OFFICE
CERTIFICATE OF CORRECTION

PATENT NO. : 11,261,179 B2
APPLICATION NO. : 16/604737
DATED : March 1, 2022
INVENTOR(S) : Ciulli et al.

It is certified that error appears in the above-identified patent and that said Letters Patent is hereby corrected as shown below:

In the Specification

Column 5, Line 55: Please correct "$R^1$" to read -- $R^{1a}$ --

Column 18, Line 43: Please correct "(10 μM), IOX2 (5 μM), IOX4 (5 μM)" to read -- (100 μM), IOX2 (50 μM), IOX4 (50 μM) --

Column 22, Line 2: Please correct "Hiss-VCB" to read -- $His_6$-VCB --

Column 24, Line 23: Please correct "ref. 3" to read -- ref. $^3$ --

Column 29, Line 13: Please correct "HIF-a" to read -- HIF-α --

Column 30, Line 23: Please correct "$COCl_2$" to read -- $CoCl_2$ --

Column 35, Line 10: Please correct "reported. 39" to read -- reported. $^{39}$ --

Column 44, Line 4: Please correct "$C_{58}H_{32}N_8O_{14}S_2$" to read -- $C_{58}H_{82}N_8O_{14}S_2$ --

Column 44, Line 39: Please correct "$C_{58}H_{32}N_3O_{14}S_2$" to read -- $C_{58}H_{82}N_3O_{14}S_2$ --

Column 45, Line 67: Please correct "$C_{58}H_{82}NO_{14}S_2$" to read -- $C_{58}H_{82}N_8O_{14}S_2$ --

Column 47, Line 5: Please correct "5, ppm" to read -- δ, ppm --

Signed and Sealed this
Second Day of April, 2024

Katherine Kelly Vidal
*Director of the United States Patent and Trademark Office*

CERTIFICATE OF CORRECTION (continued)
U.S. Pat. No. 11,261,179 B2

In the Claims

Column 67, Lines 14-30, Formula (1A), Claim 1: Please correct " 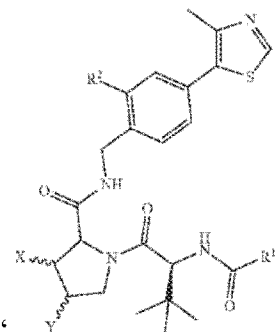 " to read

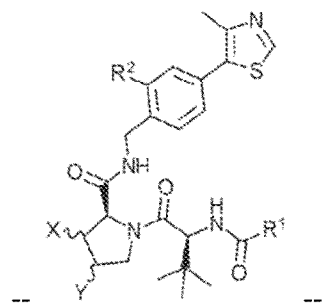 --

Column 67, Line 36, Claim 1: Please correct "alkylene, C1-C10" to read -- alkylene, —$OR^7$—, C1-C10 --

Column 75, Line 63, Claim 16: Please correct "conditions" to read -- condition --